US007138378B1

(12) United States Patent
Farrar et al.

(10) Patent No.: US 7,138,378 B1
(45) Date of Patent: Nov. 21, 2006

(54) GENETIC SUPPRESSION AND REPLACEMENT

(75) Inventors: Gwenyth Jane Farrar, County Dublin (IE); Peter Humphries, County Dublin (IE); Paul Francis Kenna, Dublin (IE)

(73) Assignee: Optigen Patents Limited, Dublin (IE)

( * ) Notice: Subject to any disclaimer, the term of this patent is extended or adjusted under 35 U.S.C. 154(b) by 0 days.

(21) Appl. No.: 09/155,708

(22) PCT Filed: Apr. 2, 1997

(86) PCT No.: PCT/GB97/00929

§ 371 (c)(1),
(2), (4) Date: Apr. 5, 1999

(87) PCT Pub. No.: WO97/37014

PCT Pub. Date: Oct. 9, 1997

(30) Foreign Application Priority Data

Apr. 2, 1996 (GB) .................................. 9606961

(51) Int. Cl.
*A01N 43/04* (2006.01)
*C12Q 1/68* (2006.01)
*C07H 21/04* (2006.01)

(52) U.S. Cl. .................. 514/44; 435/6; 435/91.31; 435/91.1; 435/320.1; 435/325; 435/375; 536/23.1; 536/23.2; 536/24.31; 536/24.5

(58) Field of Classification Search ................. 514/44; 435/6, 91.1, 325, 375, 91.31, 320.1; 536/23.1, 536/23.2, 24.5, 24.3, 24.33
See application file for complete search history.

(56) References Cited

U.S. PATENT DOCUMENTS

| 5,087,617 | A | 2/1992 | Smith ........................... 514/44 |
| 5,223,391 | A | 6/1993 | Coen et al. |
| 5,240,846 | A | 8/1993 | Collins et al. ............... 435/371 |
| 5,246,921 | A | 9/1993 | Reddy et al. .................. 514/44 |
| 5,399,346 | A | 3/1995 | Anderson et al. ......... 424/93.21 |
| 5,582,972 | A | 12/1996 | Lima et al. ..................... 435/6 |
| 5,814,500 | A | 9/1998 | Dietz |
| 5,834,440 | A | 11/1998 | Goldenberg et al. .......... 514/44 |
| 5,977,296 | A | 11/1999 | Nielsen et al. |
| 6,025,127 | A * | 2/2000 | Sidransky ....................... 435/6 |
| 6,077,705 | A | 6/2000 | Duan et al. ............. 435/320.01 |
| 6,326,174 | B1 * | 12/2001 | Joyce et al. ............. 435/91.31 |
| 6,482,803 | B1 * | 11/2002 | Roth et al. .................... 514/44 |

FOREIGN PATENT DOCUMENTS

| EP | 414134 B1 | 2/1991 |
| EP | 0475623 A1 | 3/1992 |
| WO | 92/12262 | 7/1992 |
| WO | 93/12257 | 6/1993 |
| WO | 93/21202 | 10/1993 |
| WO | 94/03596 | 2/1994 |
| WO | 94/11494 | 5/1994 |
| WO | 94/22487 | 10/1994 |
| WO | 94/26887 | 11/1994 |
| WO | 95/03335 | 2/1995 |
| WO | 95/34573 | 12/1995 |
| WO | 97/11169 | 3/1997 |
| WO | 97/32024 | 9/1997 |
| WO | 97/37014 | 10/1997 |

OTHER PUBLICATIONS

Hart et al. The introduction of two silent muations into a CFTR cDNA construct allows improved detection of exogenous mRNA in gene transfer experiments. Human Molecular Genetics, 1995, vol. 4, No. 0, pp. 1597-1602.*
Stanley Crooke, Antisense Research and Applications, Chapter 1, Basic Principles of Antisense Therapeutics, Springer-Verlag Press, Berlin, Heidelberg, New York, p. 3. Jul. 1998.*
Andrea D. Branch, A good antisense molecule is hard to find, TIBS, 47-48, Feb. 1998.*
Marshall et al. Science, vol. 269, pp. 1050-1055. May 1995.*
Gómez-Navarro et al. European Journal of Cancer, vol. 35, No. 6, pp. 867-885 (1999).*
Robinson-Benion et al. Gene transplantation: Combined antisense inhibition and gene replacement strategies. Apr. 1994, Leukemia, vol. 8, pp. s152-s155.*
Burke et al. Hairpin and Hammerhead ribozymes: how different are they? Biochemical Society Transcations (2002) vol. 30, part 6, pp. 1116-1118.*
Takagi et al. Mechanisim of action of hammerhead ribozymes and their applications in vivo:rapid identification of functional genes in the post-genome era by novel hybrid ribozyme libraries. (2002) Biochemical Society, vol. 30(6), pp. 1145-1149.*
Robinson-Benion et al., "Gene Transplantation: Combined Antisense Inhibition and Gene Replacement Strategies", Sep. 27, 1993, pp. S152-S155.
Hart et al., The introduction of two silent mutations into a CFTR cDNA construct . . . , Human Molecular Genetics, vol. 4, No. 9, 1995, pp. 1597-1602.
Herrmann, Cancer Gene Therapy: Principles, Problems, and Perspectives, *J. Mol. Med.* (1995) vol. 73: 157-163.
Crooke, "Basic Principles of Antisense Therapeutics," *Antisense Research and Application*, pp. 1-50.

(Continued)

Primary Examiner—Janet L. Epps-Ford
(74) Attorney, Agent, or Firm—Sullivan & Worcester LLP

(57) ABSTRACT

A strategy for suppressing specifically or partially specifically an endogenous gene and introducing a replacement gene, said strategy comprising the steps of:
1. providing suppressing nucleic acids or other suppression effectors able to bind to an endogenous gene, gene transcript or gene product to be suppressed and
2. providing genomic DNA or cDNA (complete or partial) encoding a replacement gene wherein the suppressing nucleic acids are unable to bind to equivalent regions in the genomic DNA or cDNA to prevent expression of the replacement gene.

Figure 1:
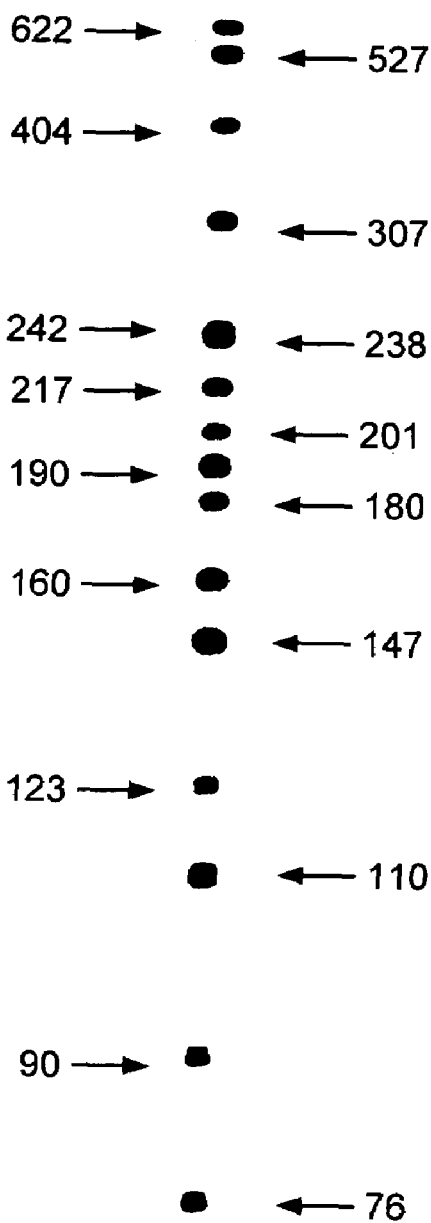

The replacement nucleic acids have modifications in one or more third base (wobble) positions such that replacement nucleic acids still code for the wild type or equivalent amino acids.

59 Claims, 30 Drawing Sheets

OTHER PUBLICATIONS

Branch, "A good antisense molecule is hard to find," *TIBS 23*, (1998), pp. 45-50.

Special News Report: "Gene Therapy's Growing Pains," *Science* (1995) vol. 269, pp. 1050-1055. Marshall.

Gomez-Navarro et al., "Gene Therapy for Cancer," *European Journal of Cancer* (1999) vol. 35, No. 6, pp. 867-885.

Denman et al., "Ribozyme mediated degradation of β-amyloid peptide precursor mRNA in COS-7 cells," *Nucleic Acids Research*, Oxford University Press, (1994) vol. 22, No. 12, pp. 2375-2382.

Lieber et al., "Adenovirus-Mediated Expression of Ribozymes in Mice," *Journal of Virology* (1996) vol. 70, No. 5, pp. 3153-3158.

Kashani-Sabet et al., "Suppression of Neoplastic Phenotype in Vivo by an Anti-ras Ribozyme," *Cancer Research* (1994), vol. 54, pp. 900-902.

Larsson et al., "Reduced β2-microglobulin mRNA levels in transgenic mice expressing a designed hammerhead ribozyme," *Nucleic Acids Research* (1994) vol. 22, No. 12, pp. 2242-2248.

Khillan et al., "Partial rescue of a lethal phenotype of fragile bones in transgenic mice with a chimeric antisense gene directed against a mutated collagen gene," *Proc. Natl. Acad. Sci. USA* (1994) vol. 91, pp. 6298-6302.

Ohkawa et al., "Ribozymes: From Mechanistic Studies to Applications in Vivo," *J. Biochem.* (1995) vol. 118, pp. 251-258.

Cotten et al. "Ribozyme mediated destruction of RNA in vivo," *The EMBO Journal* (1989) vol. 8, No. 12, pp. 3861-3866.

Kariko et al., "Lipofectin-aided cell delivery of ribozyme targeted to human urokinase receptor mRNA," *FEBS Letter* (1994) vol. 352, pp. 41-44.

Ohta et al., "Tissue-specific expression of an anti-ras ribozyme inhibits proliferation of human malignant melanoma cells," *Nucleic Acids Research* (1996) vol. 24, No. 5, pp. 938-942.

Chowrira et al., "In Vitro and in Vivo Comparison of Hammerhead, Hairpin, and Hepatitis Delta Virus Self-processing Ribozyme Cassettes," *The Journal of Biological Chemistry* (1994) vol. 269, No. 41, pp. 25856-25864.

Little et al., "Generation of a Mammalian Cell Line Deficient in Glucose-regulated Protein Stress Induction through Targeted Ribozyme Driven by a Stress-inducible Promoter," *The Journal of Biological Chemistry* (1995) vol. 270, No. 16, pp. 9526-9534.

Cameron et al., "Specific gene suppression by engineered ribozymes in monkey cells," *Proc. Natl. Acad. Sci. USA* (1989) vol. 86, pp. 9139-0143.

Kobayashi et al., "Specificity of Ribozyme Designed for Mutated DHFR mRNA," *Biochemical Pharmacology* (1994) vol. 47, No. 9, pp. 1607-1613.

Lieber et al., "Selection of Efficient Cleavage Sites in Target RNAs by Using a Ribozyme Expression Library," *Molecular and Cellular Biology* (1995) vol. 15, No. 1, pp. 540-551.

Blaese et al., "Strategies for Gene Therapy." *Pathol. Biol. (Paris)*, 1993, 41(8):672-6.

Bordignon et al., "Transfer of the ADA Gene into Bone Marrow Cells and Peripheral Blood Lymphocytes for the Treatment of Patients Affected by ADA-Deficient SCID." *Hum. Gene Ther.*, 1993, 4(4): 513-20.

Ch'ng et al., "Antisense RNA Complementary to 3' Coding and Noncoding Sequences of Creatine Kinase is a Potent Inhibitor of Translation in vivo." *Proc. Natl. Acad. Sci. USA*, 1989, 86: 10006-10010.

Chertkov et al., "The Hematopoietic Stromal Microenvironment Promotes Retrovirus-Mediated Gene Transfer into Hematopoietic Stem Cells." *Stem Cells*, 1993, 11(3): 218-27.

Cournoyer et al., "Gene Therapy of the Immune System." *Ann. Rev. Immunol.*, 1993, 11: 297-329.

Couture et al., "Retroviral Vectors Containing Chimeric Promoter/Enhancer Elements Exhibit Cell-Type-Specific Gene Expression." *Hum. Gene Ther.*, 1994, 5(6): 667-77.

Fairbanks et al., "Biochemical and Immunological Status Following Gene Therapy and PEG-ADA Therapy for Adenosine Deaminase (ADA) Deficiency." *Adv. Exp. Med. Biol.*, 1994, 370: 391-4.

Friedmann, "Overcoming the Obstacles to Gene Therapy." *Sci. Am.*, Jun. 1997, 96-101.

Grossman et al., "Successful ex vivo Gene Therapy Directed to Liver in a Patient with Familial Hypercholesterolaemia." *Nature Gen.*, 1994, 6: 335-341.

Hershfield, "PEG-ADA Replacement Therapy for Adenosine Deaminase Deficiency: An Update After 8.5 Years." *Clin. Immunol. Immunopathol.*, 1995, 76: S228-32.

Hughes et al., "Delivery of a Secretable Adenosine Deaminase Through Microcapsules- A Novel Approach to Somatic gene therapy." *Hum. Gene Ther.*, 1994, 5(12): 1445-55.

Kuo et al., "Efficient Gene Transfer into Primary Murine Lymphocytes Obviating the Need for Drug Selection." *Blood*, 1993, 82(3): 845-52.

Lyons et al., "An Improved Retroviral Vector Encoding the Herpes Simplex Virus Thymidine Kinase Gene Increases Anitumor Efficacy In Vivo." Genetic Therapy, Inc, Gaithersburg, Maryland 20878, USA. *Cancer Gene Ther.*, 1995, 2(4): 273-80.

Marini et al., "Antisense Oligonucleotides Selectively Suppress Production in Mutant Alpha2(I) Collagen in Osteogenesis Imperfecta Type IV Fibroblasts: An Approach to Gene Therapy for a Dominant Disorder of Matrix Structural Protein." *Pediatric Res.*, 1995, 37:150.

Mickisch et al., "From Laboratory Expertise to Clinical Practice: Multidrug-Resistance-Based Gene Therapy Becomes Available for Urologists." *World J. Urol.*, 1994, 12(2): 104-11.

Mitani et al., "Transduction of Human Bone Morrow by Adenoviral Vector." *Hum. Gene Ther.*, 1994, 5(8): 941-8.

Mitani et al., "Long-term Expression of Retroviral-Transduced Adenosine Deaminase in Human Primitive Hematopoietic Progenitors." *Hum. Gene Ther.*, 1993, 4(1) 9-16.

Moritz et al., "Human Cord Blood Cells as Targets for Gene Transfer: Potential Use in Genetic Therapies of Severe Combined Immunodeficiency Disease." *J. Exp. Med.*, 1993, 178(2): 529-36.

Nabel et al., "Direct Gene Transfer for Treatment of Human Cancer." Howard Hughes Medical Institute, Ann Arbor, Michigan, USA. *Ann. N. Y. Acad. Sci.*, 1995, 772: 227-31.

Nimgaonkar et al., "Long-term Expression of the Glucocerebrosidase Gene in Mouse and Human Hematopoietic Progenitors." Department of Medicine, University of Pittsburgh Medical Center, PA, USA. *Leukemia*, 1995, 9 Suppl 1: S38-42.

Orkin et al., "Report and Recommendations of the Panel to Assess the NIH Investment in Research on Gene Therapy." http://www.nih.gov/news/panelrep.html.

Postel et al., "Evidence that a Triplex-Forming Oligodeoxyribonucleotide Binds to the c-Myc Promoter in HeLa Cells, Thereby Reducing c-Myc mRNA Levels." *Proc. Natl. Acad. Sci. USA*, 1991, 88: 8227-8231.

Ramesh et al., "High-Level Expression from a Cytomegalovirus Promoter in Macrophage Cells." *Hum Gene Ther.*, 1995, 6(10): 1323-7.

Ramesh et al., "High-Level Human Adenosine Deaminase Expression in Dog Skin Fibroblasts is not Sustained Following Transplantation." *Hum. Gene Ther.*, 1993, 4(1): 3-7.

Ramsey et al., "Retrovirus Mediated Gene Transfer as Therapy for Adenosine Deaminase (ADA) deficiency." *Leukemia.*, 1995, 9 Suppl 1: S70.

Setoguchi et al., [Gene Transfer to Airway Epithelial Cells: Current Status and Future Direction] *Nihon Kyobu Shikkan Gakkai Zasshi*, 1994, 32 Suppl:8 6-95. Japanese; English abstract attached.

Sullenger et al., "Ribozyme-Mediated Repair of Defective mRNA by Targeted Trans-Splicing." *Nature*, 1994, 371: 619-622.

Takaku, [Recent Trends of Gene Therapy of Human Patients] *Nippon Rinsho*, 1993, 51(7): 1915-22. Japanese. English language summary.

Tolstoshev, "Gene Therapy, Concepts, Current Trials and Future Directions." *Ann. Rev. Pharmacol. Toxicol.*, 1993, 33: 573-96.

Vaulont et al., "Disruption of the adenosine deaminase (ADA) gene using a dicistronic promoterless construct: production of an ADA-deficient homozygote ES cell line." *Transgenic Res.*, 1995, 4(4):247-55.

Verma et al. "Gene Therapy-Promises, Problems, and Prospects." *Nature*, 1987, 389: 239-242.

Welsh et al., "Adenovirus-Mediated Gene Transfer for Cystic Fibrosis: Part A. Safety of Dose and Repeat Administration in the Nasal Epithelium. Part B. Clinical Efficacy in the Maxillary Sinus." *Hum. Gene Ther.*, 1995, 6(2): 205-18.

Welsh et al., "Cystic Fibrosis Gene Therapy Using an Adenovirus Vector: In Vivo Safety and Efficacy in Nasal Epithelium." *Hum. Gene Ther.*, 1994, 5(2): 209-19.

Yu et al., "Liposome-Mediated in vivo E1A Gene Transfer Suppressed Dissemination of Ovarian Cancer Cells that Overexpress HER-2/neu." Department of Tumor Biology, University of Texas MD Anderson Cancer Center, Houston 77030, USA. *Oncogene*, 1995, 11(7): 1383-8.

Zabner et al., "Adenovirus-Mediated Gene Transfer Transiently Corrects the Chloride Transport Defect in Nasal Epithelia of patients with cystic fibrosis." *Cell.*, 1993, 75(2): 207-16.

Zabner et al., "Safety and Efficacy of Repetitive Adenovirus-Mediated Transfer of CFTR cDNA to Airway Epithelia of Primates and Cotton Rats." *Nature Gen.*, 1994, 6: 75-83.

Zabner et al., "Correction of cAMP-Stimulated Fluid Secretion in Cystic Fibrosis Airway Epithelia: Efficiency of Adenovirus-Mediated Gene Transfer In vitro." *Hum. Gene Ther.*, 1994, 5(5): 585-93.

Zhao et al., "Generating Loss-of-Function Phenotypes of the Fushi Tarazu Gene with a Targeted Ribozyme in Drosophila." *Nature*, 1993, 365: 448-50.

Akhtar et al. (1997) In Vivo Studies with Antisense Oligonucleotides, Elsevier Science Ltd., vol. 18, pp. 12-18.

Holt, Jun. 1993, "Antisense Rescue Defines Specialized and Generalized Functional Domains For c-Fos Protein", Molecular and Cellular Biology, vol. 13, No. 6, pp. 3821-3830.

Holt et al., Jul. 1986, "Inducible Production of c-Fos Antisense RNA Inhibits 3T3 Cell Proliferation", Proc. Natl. Acad. Sci., vol. 83, pp. 4794-4798.

Millington-Ward et al., 1997, "Strategems In Vitro For Gene Therapies Directed To Dominant Mutations", Human Molecular Genetics, vol. 6, No. 9, pp. 1415-1426.

Mitani et al., 1993, "Gene Transfer Therapy For Heritable Disease: Cell And Expression Targeting", Phil. Trans. Soc. Land. B., vol. 339, pp. 217-224.

Stacey et al., Aug. 1987, "Rescue of Type I Collagen-Deficient Phenotype by Retroviral-Vector-Mediated Transfer of Human proα1(I) Collagen Gene Into Mov-13 Cells", Journal of Virology, vol. 61, No. 8, pp. 2549-2554.

International Search Report for International Patent Application No. PCT/GB96/02357, 4 pages. (1996).

Carter et al., "Antisense Technology for Cancer Therapy: Does it Make Sense?" *Cancer Res.*, 1993, 67:869-876.

Cazenave et al., "Comparative Inhibition of Rabbit Globin mRNA Translation by Modified Antisense Oligodeoxynucleotides." *Nuc. Acid Res.*, 1989, 17:4255-4273.

Connell et al., "Molecular Cloning, Primary Structure, and Orientation of the Vertebrate Photoreceptor Cell Protein Peripherin in the Rod Outer Segment Disk Membrane", 1990, 29:4691-4698.

D'Alessio et al, "Characterization of a COLIAI Splicing Defect in a Case of Ehlers-Danlos Syndrome Type VII: Further Evidence of Molecular Homogeneity." *The American Society of Human Genetics*, 1991, 49:400-406

Dalgleish et al., "Length polymorphism in the pro α2(I) collagen gene: an alternative explanation in a case of Marfan syndrome." *Human Genetics*, 1986, 73:91-92.

Dosaka-Akita et al., "Inhibition of Proliferation by L-myc Antisense DNA for the Translational Initiation Site in Human Small Cell Lung Cancer." *Cancer Res.* 1995, 55:1559-1564.

Dryja et al., "A point mutation of the rhodopsin gene in one form of retinitis pigmentosa." *Nature*, 1990, 343:364-366.

Duval-Valentin et al., "Specific inhibition of transcription by triple helix-forming oligonucleotides." *Proc. Natl. Acad. Sci. USA*, 1992, 89:504-508.

Ellis et al., "Design and specificity of hammerhead ribozymes against calretinin mRNA." *Nuc. Acid Res.*, 1993, 21:5171-5178.

Farrar et al., "Autosomal Dominant Retinitis Pigmentosa: Linkage to Rhodopsin and Evidence for Genetic Heterogeneity." *Genomics*, 1990, 8:35-40.

Farrar et al., "A three-base-pair deletion in the peripherin-RDS gene in one form of retinitis pigmentosa." *Nature*, 1991, 354:478-480.

Farrar et al., "Autosomal Dominant Retinitis Pigmentosa: A Novel Mutation at the Peripherin/RDS Locus in the Original 6p-Linked Pedigree." *Genomics*, 1991, 14:805-807.

Farrar et al., "Progress in Genetic Linkage for Retinitis Pigmentosa and Gene Delivery to Ocular Tissues." *Invest Ophthamol Vis. Sci. (ARVO)*, 1995, 36:(4).

Feng et al., "Neoplastic Reversion Accomplished by High Efficiency Adenoviral-mediated Delivery of an Anti-ras Ribozyme." *Can. Res.*, 1995, 55:2024-2028.

Filie et al., "A De Novo $G^{+1\rightarrow}A$ Mutation at the α2(I) Exon 16 Splice Donor Site Causes Skipping of Exon 16 in the cDNA of One Allele of an OI Type IV Proband." *Human Mutation*, 1993, 2:380-388.

Gaughan et al., "Ribozyme Mediated Cleavage of Acute Phase Serum Amyloid A (A-SAA) mRNA in vitro." *FEBS Letters*, 1995, 374:241-245.

Hanvey et al., "Antisense and Antigene Properties of Peptide Nucleic Acids." *Science*, 1992, 258:1481-1485.

Herschlag et al., "An RNA chaperone activity of non-specific RNA binding proteins in hammerhead ribozyme catalysis." *EMBO*, 1994, 13:(12):2913-2924.

Herskowitz, "Functional inactivation of genes by dominant negative mutations." *Nature*, 1987, 329:219-222.

Humphries et al., "On The Molecular Genetics Of Retinitis Pigmentosa." *Science* 1992, 1-5.

Jordan et al., "Localization of an autosomal dominant retinitis pigmentosa gene to chromosome 7q." *Nature Genetics*, 1993, 4:54-58.

Kajiwara et al., "Mutations in the human retinal degeneration slow gene in autosomal dominant retinitis pigmentosa." *Nature*, 1991, 354:480-483.

Lange et al., "In Vitro and In Vivo Effects of Synthetic Ribozymes Targeted Against BCR/ABL mRNA." *Leukemia*, 1993, 7:1786-1794.

Mansergh et al., "Evidence for genetic heterogeneity in Best's vitelliform macular dystrophy." *J. Med. Genet*, 1995, 32:855-858.

Mashhour et al., "In Vivo Adenovirus-Mediated Gene Transfer Into Ocular Tissues." *Gene Therapy*, 1994, 1:122-126.

McWilliam et al., "Autosomal Dominant Retinitis Pigmentosa (ADRP): Localization of an ADRP Gene to the Long Arm of Chromosome 3." *Genomics*, 1989, 5:619-622.

Mitani et al., "Gene transfer therapy for heritable disease: cell and expression targeting," *Philos Trans. R. Soc. Lond. B. Biol. Sci.* 1993, 339:217-224.

Nathans et al., "Isolation, Sequence Analysis, and Intro-Exon Arrangement of the Gene Encoding Bovine Rhodopsin", *Cell*, 1983, vol. 34, 807-814.

Ott et al., "Localizing multiple X chromosome-linked retinitis pigmentosa loci using multilocus homogeneity test." *Pro. Natl. Acad. Sci.*, 1990, 87:701-704.

Oyama et al., "N-ras Mutation of Thyroid Tumor with Special Reference to the Folicular Type." *Pathol Int.*, 1995, 45:45-50.

Phillips et al., "A Substitution at a Non-glycine Position in the Triple-Helical Domain of proα2(I) Collagen Chains Present in an Individual with a Variant of the Marfan Syndrome." *The American Society for Clinical Investigation, Inc.*, 1990, 86:1723-1728.

Quattrone et al., "Reversion of the Invasive Phenotype of Transformed Human Fibroblasts by Anti-Messenger Oligonucleotide Inhibition of Urokinase Receptor Gene Expression." *Can. Res.*, 1995, 55:90-95.

Reichenberger et al., "Genomic Organization and Full-Length cDNA Sequence of Human Collagen X", *FEBS*, 1992, vol. 311, 3:305-310.

Rimsky et al., "Trans-dominant inactivation of HTLV-1 and HIV-1 gene expression by mutation of the HTLV-1 Rex transactivator." *Nature*, 1989, 341:453-456.

Sun et al., "Sequence-specific intercalating agents: Intercalation at specific sequences on duplex DNA via major groove recognition by oligonucleotide-intercalator conjugations." *Proc. Natl. Acad. Sci USA*, 1989, 86:9198-9202.

Valera et al., "Expression of GLUT-2 Antisense RNA in β Cells of Transgenic Mice Leads to Diabetes." *J. Biol. Chem.*, 1994, 269:28543-28546.

Van Socst et al., "Assignment of a Gene for Autosomal Recessive Retinitis Pigmentosa (RP12) to Chromosome 1q31-q32.1 in an Inbred and Genetically Heterogeneous Disease Population." *Genomics*, 1994, 22:499-504.

Vasan et al., "A Mutation in the Proα2(I) Gene (COLIA2) for Type 1 Procollagen in Ehlers-Danlos Syndrome Type VII: Evidence Suggesting That Skipping of Exon 6 in RNA Splicing May Be a Common Cause of the Phenotype." *The American Society of Human Genetics*, 1991, 48:305-317.

Westerhausen et al., "A sequence polymorphism in the 3'-nontranslated region of the proα1 chain of type I procollagen." *Nucleic Acids Research*, 1990, 18:4968.

Willing et al., "Molecular Heterogeneity In Osteogenesis Imperfecta Type I." *American Journal of Medical Genetics*, 1993, 45:223-227.

* cited by examiner

SEQ ID NO: 1 Human Rhodosin

TCCCTTNTGNTAGATTGCANNNCCCAATAAANAAGGNCCCGCTTAAAGGCTTATCGAAA
TTAATACGACTCACTATANGGAGACCCAAGCTTAGAGTCATCCAGCTGGAGCCCTGAGTG
GCTGAGCTCAGGCCTTCGCAGCATTCTTGGGTGGGAGCACGGTCAGCCACAAGGG
CCACACAGCCATGAATGGCACAGAAGGCCCTAACTTCTACGTGCCCTTCTCCAATGCGACGG
GTGTGGTACGCAGCCCTTCGAGTACCCACAGTACTACCTGGCTGAGCCATGGCAGTTCT
CCATGCTGGCCGCCTACATGTTTCTGCTGATCGTGCTGGGCTTCCCATCAACTTCCTCA
CGCTCTACGTCACCGTCCAGCACAAGAAGCTGCGCACGCCTCTCAACTACATCCTGGCTC
AACCTAGCCGTGGCTGAACTCTTCATGGTCCTANGTGGCTTCCACCAGGACACCTCTACANCT
CTCTGCATGGGATACTCGTCTTCGGGCCCACAGGATGCAATTGGANGGCTCTTTGCACCTG
GNGGAAATTGCCTGTGGTCCTNGTGGTCNGGNCACCAACGTACTGGTNGTGTNTANCCC
AGAACAACTCCGCTCCC

FIG. 10

SEQ ID NO:2 mut447

GGNNNNTTGGGTCGCGGCATTNAAGAACTCANGGNCCCGCAGCATTCTTGGGTGGGAGCAGCTACGGGTCAGCCACAAGGG
CCACAGCCATGAATGGCACAGAANGCCCTAACTTCTACGTGCCCTTCTCCAATGGCGACGGGTGTGGTACGCAGCCCCTTC
GAGTACCCACAGTACTACCTGGCTGAGCCATGGCAGTTCTCCATGCTGGCCGCCTACATGTTTCTGCTGATCGTGCTGGG
CTTCCCCATCAACTTCCTCACGCTCTACGTGACCGTCCAGCACAAGAAGCTGCGACCCTCAACTACATCCTGCTCA
ACCTANCCGTGGNTGAACTCTTCATGGTCCTAGGTGGCTTCACCANCAACCTCTANACCTCTCTGCATGGANACTTCNTC
TTCCGGCCCACAGGATGCAATTTGGAAGGNTTCCTTTAACACCCGGGGGGGAAAATTGCTGTGCCTGGTCCTTGGTGTCCG
GNCANCNAACGTACTTGTGTNTTTAANCCATAAACAATTCCGCTTCGGGAAAAACATGCCANCNTGGGGTTTCCTTCA
CTNGGTTANGGGCNGGCTGCCCCACCCCAATCCCCNGGTNGTCAANTAATCCCAAGGGCNNANTGNCNTTTTAAACAAA

FIG. 11

SEQ ID NO:3 Pro23Leu

NNNTTAGGGNCGGATGTCNATATATAAGCAGANCTCTCTGGGCTAACTAANAAGAACCCACTGGCTTACTGGCTTATCGAAA
TTAATACGACTCACTATAGGGAGAGACCCAAGCTTCCGGAAAGCCTGAGCTCAGCCACAAGGGCCACAGCCCATGAATGGCAC
AGAAAGCCCTAACTTCTACGTGCCCTTCTCCAATGCGACGGGTGTGGTACGCAGCCTCTTCGAGTACCCACAGTACTACC
TGGCTGAGCCAGTTCTCCATGGCCGCCTACACATGTTTCTGCTGATCGTGCTGGGCTTCCCCATCAACTTCCTC
ACGCTCTACGTCACCGTCCAGCACAAGAAGCTGCGCACGCCCTCAACTACACATCCTGCTCAACCTANCCGTGGCTGAACT
CTTCATGGTCCCTANGTGGCTTCACCANCACACCCTCTACACCTCTCTGCATGGATACTTCGTCTTCCTGGCCACAGGATGCA
ATTTGGAAGGCTTCTTTGCANCCTGGGNCGGGAAAATTGCCTGTCCTGGTCCTGCCATCAACNGTACTTGTTGT
NTNTTACCCATNAACAATTCCGCTCCCGGAAAACATGCACATGGNTTGCCTCACTGGNTCTGGGGCNGGCNCCCCCACCC
CACCCCCGGTGGTCANTTATCCCANGGCGNAATGCCTTTNANNAAA

FIG. 12

SEQ ID NO:4 RIB10a

CNGCNCGTTGAAATATAAGCAGACCCCTCTGGNTAACTANAATAACCACTGCTTACTGGCTTATCGAAATTAATACGACTC
ACTATANGGAGACCAAGCTTGGTCGGTTCTGATGAGTCCGTGAGGACGAAACGTANANTCTANAGGGCCCTATTCTATAGT
GTCACCTAAATGCTAGANCTCGCTCAGNCTCGCTGATCAGCCTCGACTGTGCCTTCTAGTTGCCAGCCATCTGTTGTTTGCCCCTCCCCC
GTGCCTTCCTTGANCCTGGAAGGTGCCACTCCCACTGTCCTTTCCTAATAAAATGAGNAATTGCNTCTCATTGTCTGAGT
AGTGTCATCCAATCTGGGGGGTGGGGTGGGCAGNACACNAGGGAAGATGGGAAAACATACAGGCATGCTGGGANGCCGT
GGNTCTATGNCTCNGAGGCGAAAAAACACTGGGGNCTAGGGTACCCCACCCCTGTACGGCCATAACNCGNGGTTTGTG
GTACCCACTAACGTANNTGCACCCTACCCGNCTTCNTTCTCCTCTTNCCATTCCGGTTCCCTCACCNAACGGGCCTTNG
TCATATCTNGGNCCACCAAATANAGTAGTCTTTGCCCCAAAGTCCCTNATGACCTNTAAGACCTTCANNANCCCCCCTT
NTTNAAANANCNNNNNNNNNNNNNNNANNNNCCNGNAAAANAACAACTAATTTTGGGAACCCCCCCCNANAAACCCTTTCC
NTNTTCCCCCNATTTAATNTTNNNNTNCCCCCCCCCCCCNNTTTTTNNCNCCCCNNNANNNG

FIG. 13

SEQ ID NO:5

CNCCCCGCCCNTTNAAANAANCCNAGCCTCTGGCNAACTANANAACCACTGCTTACTGGCTTATCNAAATTAATACGAC
TCACTATAGGGAGACCCAAGCTTTACTCGAACTGATGAGTCCGTGAGGACGAAANGCTGCTCTANANGCCCTATTCTAT
ANTGTCACCTAAATGCTAGAGCTCGCTGATCAGCCTGACTGTGCCTTCTAATTGCCAGCCATCTGTTGCCCCTCC
CCCGTGCCTTCCTTGACCCTGGAAGGTGCCACTCCCACTGTCCTTCCTAATAAAATGAAGATNTTNCATCNCATTGTCT
GAGTAAGTGTCATTCTATTCTGGGGGTGGGGCACGACANCAACAACTGGGGCTCTANGGGTATCCCCCCCTGTAAC
TGGGGATNCCGTGGGCTTCTATNGCTTCTGAAGCGGAAAAAACAACTGGGGCTCTANGGGTATCCCCCCCTGTAAC
GNGCATTAAACNCGGGGTGTTGTGGTTACCCCAACTTAACGCTANCTTGCAACGCCCNACGCCCNCCTTTCCTTTCT
CCCTTCCTTCNCCCACTTTCCGGTTCCCNTCAACCCNAATCGGGGCCCCTTAGTCCAATTATGCTTCGGCCCCNCCCN
AAACTAATAGGTNGGTTCTTTNGCC

FIG. 14

SEQ ID NO:6 mouse rhodopsin

TCAGTGCCTGGAGTTGCGCTGTGGGAGCCCGTCAGTGGCTGAGCTCGCCAAGCAGCCTTGGTCTCTGTCTACGAA

FIG. 15

SEQ ID NO:7 m rho mut 1460

NNNNTCTTCCNCTTTCGTTTGTTGNANANTCANNAAANANAGGCGNCCCGGAAGGTGTCAGTGCCTGGAGTTGCGCTGTG
GGACCCGTCANTGGCTGAGCTCGCCAAGCAGCCTTGGTCTCTGTCTACGAAGAGCCCGTGGGGCAGCCTCGAGAGCCGCA
GCCATGAACGGCACAGAGGGCCCCAATTTCTATGTGCCCTTCTCCAACGTCACAGGCGTGGTGCGGAGCCCTTCGANCN
TCCGCAGTACTACCTGGCGGAACCATGGCAGTTCTCCATGCTGGCAGCGTACATGTTCCTGCTCATCGTGCTGGGCTTCC
CCATCAACTTCCTCACGCTCACGTACACGTACCGCACACAAGAAGCTGCGCACACCCCCTCAACTACATCCTGGCTCAACT
TGGGCCGNTGGGNTTGGAACCTCCTTCCCATTGGGTCNTTCCCGGAANGGANTNCACCAACCACCCCTCTAACACATCAA
CTCCCATGGGCTACTTCGTTCTTTTGGGGCCCNCAGGCTGTTAATCTCGAAGGGCTTCTTTGCCACACCTTGGAAGTGAA
ATCNCCCTGGTTCCCTGGTGGTCNTGGCCATTAACGCTACTTGTGGTCCTGCAACCCAATAACAATTC

FIG. 16

SEQ ID NO:8 RIB33

TCCCCTNNTTTTTGTAGCNCTGCCAANAAAAAAGGCCAGCTCACAGGANAANTANANAACCCACTGCTTACTGGCTTANC
NAAATTAATACGACTCACTATAGGGAGACCCAAGCTTGGCACATCTGATGAGTCCGTGAGGACGAAAAAATTGGTCTACA
GGGCCCTATTCTATAATGTCACCTANAGCTGCTGATCATCCTCNACTGTGCCTTCTACTTGCCAGCCNTCTN
TTGTTTGCCCCTCCCCCGTGCCTTCCTTGACCCTGGAAGGTGCCACTCCCACTGTCCTTCCTAATAAAATGAGGAAATT
GCATCGCATTGTCTGAGTAAGTGTCATTCTATTCTGGGGGTGGGGCAGGACNNCAAAGGGGAAGATTGGGAAAT
ACAATANCCAAGGAGNCNCTCCCCNCCCCTNTCCCCCNGGTAATTGCGATTNGGCTCTNTCGCTTCCTTAAGGCNGAANAAACAACTNGG
GCGCTNCGGGGTTCCCCCNCCCNGCCTAACGCCCCCCCCCCCGGGTGTTGTTACTCCCCACCTNAACG
CTACANTTGCCAGCGCCTAACGCGCCCCCCCCCCCCCGGCTTTCCCCGCTTTCCCCNCCAANCC
NAAATCNGG

SEQ ID NO:9 HUM RDS

NNTTGTTGGTNCAGTNGGATGTCTATATAAGCAGAGNCTCTGGCTAACTAGNAGAACCCACTGCTTACTGGCTTATCGAA
ATTAATACGACTCACTATAGGGAGACCCAAGCTTGGTACCGAGCTCNGATCCACTAGTAACGCCGCCAGTGTGCTGGAA
TTCTTCAGCGCCCACGACCAGTGACTATCCCCTGCTCAAGCTGTGATTCCGAGACCCCTGCCACCACTACTGCATTCACG
GGGGATCCCANGCTAATGGGACTCGACATGGGTTGCCCCCACGGCAANCTCCCTACANCTTGGGCCANCTNCACTTTTCCC
AAAGNCCTAAATCTCCGCCTCTCGGCTCNTTAANGTTNGGGGTGGGGANCTGTGCTGTGGGAAACAACCCAGAANANACT
TGGGCAGCATGGNGCTACTGAAAGTNCATTTTGAACAGAANAAACGGTCCANTTTGGCCAAGGNNCNNGNTCCTAAANT
GGTTCTCCNTNTTGGTNGNNTCCNCNCTTTCCNCNCTNGGAATGTTCCTGAAAAATTNAACNCCAAAAAGAACAAATTG
AAAATANTTCTNAAAACCCTTTGTTNCCCCCCCCNAAAAGGGAAGGGNNGGNNCCTTTTNTTCCCCCCGGGG
GGGGAAAATTTTNNNNNAANCCCCCCCCCCNTTTTTTNA

FIG. 18

SEQ ID NO:10 h per mut 257

TTATACNACACACTATANGGAGACCAAGCTTGGTACCGAGCTCGGATCCACTAGTAACGGCCGCCAGTGTGCTGGAATTC
TTCANCGGCCAGGACCAGGACTATCCCCTGCTCAAGCTGTGATTCCGAGACCCCTGCCACCACTACTGCATTCACGGGGG
ATCCCAGGCTAGTGGGACNCGACATGGGTATCCCCAGGGCAGCTCCCTACAGCTTGGGCCATCTGCACTTTTCCCAAGG
CCCTAAGTCTCCGCCTCTGGGCTCGTTAANGTNTGGGTGGGAGCTGTGTGTGGGAAACAACCCGGACTACACTTGGCA
AGCATGGCGCTGCTGAAAGTCAAGTTTGAACAGAAAAAANGGGTCAAGTTGGCCCAAGGGCTCTGGCTCAGGAAACTGG
GTTNCCCNCCNNGTTTNGGTTTGGNTGCATCANCTNCCAAAAANANNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNN

FIG. 19

SEQ ID NO:13 h per mut (359)

TTTTTNTGGNTNTCNAATTAATACGACTCACTATAGGGAGACCCAAGCTTGGTACCGAGCTCGGATCCACTAGTAACGGC
CGCCAGTGTGCTGGAATTCTTCANCGCCCAGGACCAGGACTATCCCCTGCTCAAGCTGTGATTCCGAGACCCCTGCCACC
ACTACTGCATTCACGGGGATCCCAGGCTAGTGGGACTCGACATGGGTAGCCCCCAGGCAGCTCCCTACAGCTTGGGCCA
TCTGCACTTTTCCCAAGGCCCCTAAGTCTCCGCCTCTGGGCTCGTTAAGGTTTGGGGTGGGGAGCTGTGCTGTGGGAAGCAA
CCCGGACTACACTTGGCAAGCATGGCGCTACTGAAAGTCAAGTTTGACCAGAAAAAANCGGGTCAAGTTGGGCCCAAGGGC
TCTGGGCTCNATGNAAACCTNGGTTTCCCCCCCTNTTTGGGCTGGGCATCATCTTTCAGCCTGGGANTGTTCCTG
AANATTGAACTCCCAAAGAGANCGATGTGATGAATAATTCTGAAANCCATTTGTGCCCCACTCATTGANAAGGANGGGG
TGNATCCTGTTTCTTCACTCCCTGNTGGAAAATGCTACAANCCCTGAACC

FIG. 20

SEQ ID NO:14 rib30

CNTTGGTGGTNCTGTGTCGGNTGTCTATATAAGCAGAGCTCTCTGGCTAACTAGAGAAGAACCCACTGCTTACTGGCTTATCGA
AATTAATACGACTCACTATAGGGAGACCCAAGCTTACTTTCAGCTGATGAGTCCGTGANGGACGAAAGCGCCATCTAGAG
GGCCCTATTCTATAGTGTCACCTAAATGCTAGAGCTCGTAGAGCTCGATCAGCCTGCTGATCAGCCTCGACTGTGCCTTCTAGTTGCCAGCCATCTGT
TGTTTGCCCCTCCCCCGTGCCTTCCTTGACCCTGCCTTCCTTGACCCTGCCACTCCCACTGTCCTTCCTAATAAAATGATGAAATTG
CATCGCATTGTCTGAGTAGGTGTCATTCTATTCTGGGGGTGGGTGGGGCANGACANCAAGGGGAAGATTGGGAAAACA
ATNCCCGCCTGCTGGGGATGCGGTGGGCTTCTATGGCTTCTGAGGCGAAANAACNNCTGGGTCTNGGGGGTCTNCCCNCCCC
CCTGTNNCGGCCTTNANNCGGGGGTTTTGTGNTCCCCCNCTTANCNNTNNTTNNNNNCCNNCCCCCNNCCCNCNNT
NNTCCNNNNNTNCNCNNNTNNNNNGNNTCCNNNNNNTCCNNNNNGGGCNCNNNNNGNTCCNNTNNNNCCNCNNNNNC
NNNCNNNNNNNNTNTGNNGGCCCNNNNNCNNNNNNCNCN

FIG. 21

SEQ ID NO:15rib31

NNTTTNTCCTACGNCCGTTTAAANANANAACCAGACCCCTCTGGANAATTANATNNCCACTGCTTACTGGCTTATCGAAATC
AATACGACTCACTATANGGAGAGACCCCAAGCTTACAGTCCCTGATGAGTCCGTGAGGACGAAAGGCTGAATCTANAGGCCC
TATTCTATAGTGTCACCTAAATGCTAGAGCTCGCTGATCAGCTCGACTGTGCCTTCTAATTGCCAGCCATCTGTTGTTT
GCCCCTCCCCCGTGCCTTCCTTGACCCTGGAAGGTGCCACTCCCACTGTCCTNTCCTAATAAAATGATGANNTTGCATCG
CATTGTCTGAGTAAGTGTCANTCTATTCTGGGGGGTGGGCANGACANCAAGGGGAAGATTGGGAAAAACATTN
CACGCATGCCGGGGATGCGGTGGGCTCTNTTNGCNTCNGAAGGCNGAAAAAACNACTGGGCCCTANGGGTNNCCCNN
TCCCCCNTGTAACNGNCCTNAACNGGGGGTTTGGTTNNCCNANCTTANCNCTNAACTTCCNNCCCCNNNCCCCCNC
TCTTCCCTTTTCCTCCATCTCCNCNTTNCCCGNTCTCCCGNTNCACTNAAATGGGGCCCCTACNGGNCTNTNTNTCT
CTTNNNNCCNCCNCCCNANANATATNCTNGNTNNTTCNCCTCTCGGCCCCT

FIG. 22

SEQ ID NO:16 PCR3 polcolla2

NTCNCGNCATTTAANCAGGCCAGGNCTACCGCNNGGTCCANGTAGGCCGGAGCAACGCCGGGAAGGCCAGCAG
CACCCTTGGCACCAGTAAGGCCGTTTGCTCCAGGATTACCANGAGGTCCAACGGGCCGGAGAGCCTGGAANACCACTT
CACCACGGGGAACCGGCGGGTCCAGTAGGACCAGCGTTACCAACAGTCCAATTTCACCCTTGGGCCAGGGCACCTGG
GAAGCCTGGANGGCCAGCAGACCAATGGGACCAGGACCACCAGAGCTCCATCACTGCTTTNGCNCAGCTGGGC
AAGGGCACAACACTTCTCTCACANGAACCCACGGCTCCTGTTTNACTGAATTCCATTTCACAGGGCACAGTTCACCTT
CACACAAGAACACGGNTGTCCTTCATCATCAGACATGTTTCCTAATGCTTGAGCAGANTCAGATTCAGGAAACACACAC
CTTTGTCCACATCTCTNCACAGTCTCGGTTTCAGGTACACTCCACCTGCAGAGGCACTGACCAACCTGAGACATTGACA
TTNCAGNCCACAGTCTGAACTGAGCGGGCACGCCATGGCNAGTCCGTCAGNATCATCTTCTTANCATTCCCAA
NGGGCAGAATGAAAGCTGACTCCCCAATGTCTTATTTTTAANNANGGTTTNAAANAANNNNNNNNNNNNNNC
CCCCCCCTTTNGGGTTTATTATCTATNCNNCCCNTNGGATATCTTTNCCCCCTNAAANTTTNTTNTTTT
TNNNN

FIG. 23

SEQ ID NO:17 tot polcolla2

CCCTTTAAAACANGGCCAGGAATACCGCGGGGTCCAGGAGGCCGGGGACCCCANCAACGCCGGGAANGCCCAGCAGCACC
CTTGGCACCAGTAANGCCGTTTGCTCTCCAGGATTACCAGGAGGTCCAACGGGCCGGAGANGCCTGGAAGACCACTTCACC
ACGGGGAACGGCGGGACCAGCANGACCAGCGTTACCAACAGCTCCAATTCACCCTGGGGCCAGGGGCACCTGGGAAGC
CTGGANGGCCAGCAGACCAATGGGANCAGCAGGACCACGGACCACACTTCCATCNCTGCCNCTGCCACCAGCTGGGCAA
GGGCACAACACTTCTCTCTCACNAAGAACCCACGGNTCCTGTTTAACTCCATTTCACAGGGCACAGTTCACCTTC
ANACAGAACACGGGTGTCCTTCATCATCAAACATNTTTCCTATNCCTTGAGCAGAATCAGGAACACACACTTTG
TCACATCTCCTCACAGTCTCGGTTTCAGGTAACACTCNCACCTGCAGAGGCACTGACNAANCTCAGANATTTANATTCCN
CTCCNCAGTTTGAACTTAGGCGGGCCCTNNCATTTGGNTTGTCCTAACCTNTNGGGGGTTTTNCTTNNNNNNNNTTT
NACNANTCCCAANGGGGANAANANAGNTGACTCCTATGTCTTNTNAAAAGGTTTTTNAAAAATTAACCCCCCCTN
TTGGGTTATTTATTTTTTTTNNCCCCCCTTTTGNGAANCNTNNCCCCNTTTTCCCNNNAAANTTTTTTTNTTTTTTT

FIG. 24

SEQ ID NO:18 RIB908

NCTTTCNNTCTNATNCATANAAGCAGGCCCTCTNNAAAAACTANANTTTCCACTGCTTACTGGCTTATCGAAANCAATAC
GACTCACTATAGGGAGACCCAAGCTTCGGCGGCTTCGGCGGCTGATGAGTCCGTGAGGACGAAACCAGCATCTAGAGGCCCTATTCTA
TAGTGTCACCTAAATGCTAGAGCTCGCTGATCAGCCTCGACTGTGCCTTCTAGTTGCCTCATCTGTTGCCCCTC
CCCCGTGCCTTCCTTGACCCTGGAAGGTGCCACTCCCACTGTCCTTTCCTAATAAAATGAGAAATTGCATGCATTGTC
TGAGTANGTGTCATTCTATTCTGGGGGTGGGCANGACANCAAGGGGAAGATTGGGAANACAATAACAGGCAT
GCTGGGGATGCGGTGGGCTTCTATGGCTCTGAGGCGGAAAGAACCAACTGGGGCTCTANGGGTATCCCCACNCCCCTGT
TACCGGGCATTAANCGGGGGTGTGTGGTTACCCNCAACTTAACGCTACACTTGCCACGCCTAACGCCCCTCCTTTC
GCTTCTTCCTTCCTCCCACTTCCCCGNTTTCCCTTCAACTCTAATCGGGCNCCTTAGGTCCAATTAATCTTACGGN
CNCACCCAAAACTNATAGGTAAGTCCCTTNTGGCCCCCCAAAAAGGTTCCCCTAAATG

FIG. 25

GENETIC SUPPRESSION AND REPLACEMENT

REFERENCE TO RELATED APPLICATIONS

This application was filed under 35 U.S.C. §371 for, and claims priority to, PCT/GB97/00929, filed Apr. 2, 1997, which claims priority to GB9606961.2, filed Apr. 2, 1996, the disclosures of which are incorporated by reference herein.

FIELD OF THE INVENTION

The present invention relates to a strategy for suppressing a gene. In particular the invention relates to suppression of a mutated gene that gives rise to a dominant or deleterious effect, either monogenically or polygenically.

BACKGROUND OF THE INVENTION

Studies of degenerative hereditary ocular conditions, including Retinitis Pigmentosa (RP) and various macular dystrophies, have resulted in a substantial elucidation of the molecular basis of these debilitating human retinal degenerations. Applying the approach of genetic linkage, x-linked RP (xlRP) genes have been localised to the short arm of the X chromosome (Ott et al. 1990). Subsequently, the gene involved in one form of xlRP was identified. Various genes involved in autosomal dominant forms of RP (adRP) have been localised. The first of these mapped to 3q, close to the gene encoding the rod photoreceptor protein rhodopsin (McWilliam et al. 1989; Dryja et al. 1990). Similarly, an adRP gene was placed on 6p close to the gene encoding the photoreceptor protein peripherin (Farrar et al. 1991a,b; Kajiwara et al. 1991). Other adRP genes have been mapped to discrete chromosomal locations; however the disease genes as yet remain uncharacterised. As in xlRP and adRP, various genes involved in autosomal recessive RP (arRP) have been localised and in some cases molecular defects characterised (Humphries et al. 1992; Farrar et al. 1993; Van Soest et al. 1994). Similarly, a number of genes involved in macular dystrophies have been mapped (Mansergh et al. 1995). Genetic linkage, together with techniques for mutational screening of candidate genes, enabled identification of causative dominant mutations in the genes encoding rhodopsin and peripherin. Globally, about 100 rhodopsin mutations have been found in patients with RP or congenital stationary night blindness. Similarly, approximately 40 mutations have been characterised in the peripherin gene in patients with RP or macular dystrophies. Knowledge of the molecular aetiology of these retinopathies has stimulated the generation of animal models and the exploration of methods of therapeutic intervention (Farrar et al. 1995; Humphries et al. 1997).

Similar to RP, osteogenesis imperfecta (OI) is an autosomal dominantly inherited human disorder whose molecular pathogenesis is extremely genetically heterogeneous. OI is often referred to as 'brittle bone disease', although additional symptoms including hearing loss, growth deficiency, bruising, loose joints, blue sclerae and dentinogenesis imperfecta are frequently observed (McKusick, 1972). Mutations in the genes encoding the two type I collagen chains (collagen 1A1 and 1A2) comprising the type I collagen heterodimer have been implicated in OI. Indeed hundreds of dominantly acting mutations have been identified in OI patients in these two genes, many of which are single point mutations, although a number of insertion and deletion mutations have been found (Willing et al. 1993; Zhuang et al. 1996). Similarly mutations in these genes have also been implicated in Ehlers-Danlos and Marfan syndromes (Dalgleish et al. 1986; Phillips et al. 1990; D'Alessio et al. 1991; Vasan NS et al. 1991).

Generally, gene therapies utilising viral and non-viral delivery systems have been used to treat inherited disorders, cancers and infectious diseases. However, many studies have focused on recessively inherited disorders, the rationale being that introduction and expression of the wild type gene may be sufficient to prevent/ameliorate the disease phenotype. In contrast gene therapy for dominant disorders requires suppression of the dominant disease allele. Notably many of the characterised mutations causing inherited diseases such as RP or OI are inherited in an autosomal dominant fashion. Indeed there are over 1,000 autosomal dominantly inherited disorders in man. In addition, there are many polygenic disorders due to co-inheritance of a number of genetic components which together give rise to the disease state. Effective gene therapies for dominant or polygenic diseases may be targeted to the primary defect and in this case may require suppression of the disease allele while in many cases still maintaining the function of the normal allele. This is particularly relevant where disease pathology is due to a gain of function mutation rather than due to reduced levels of wild type protein. Alternatively, suppression therapies may be targeted to secondary effects associated with the disease pathology, for example, programmed cell death (apoptosis), which has been observed in many inherited disorders.

Strategies to differentiate between normal and disease alleles and to selectively switch off the disease allele using suppression effectors such as antisense DNA/RNA, PNAs, ribozymes, or triple helix forming DNA, targeted towards the disease mutation may be difficult in many cases—frequently disease and normal alleles differ by only a single nucleotide. A further difficulty inhibiting development of gene therapies is the heterogeneous nature of some dominant disorders—many different mutations in the same gene give rise to a similar disease phenotype. Development of specific gene therapies for each of these may be prohibitive in terms of cost.

Suppression effectors have been used previously to achieve specific suppression of gene expression. Antisense DNA and RNA has been used to inhibit gene expression in many instances. Modifications, such as phosphorothioates, have been made to oligonucleotides to increase resistance to nuclease degradation, binding affinity and uptake (Cazenave et al. 1989; Sun et al. 1989; McKay et al. 1996; Wei et al. 1996). In some instances, using antisense and ribozyme suppression strategies has led to reversal of a tumor phenotype by reducing expression of a gene product or by cleaving a mutant transcript at the site of the mutation (Carter and Lemoine 1993; Lange et al. 1993; Valera et al. 1994; Dosaka-Akita et al. 1995; Feng et al. 1995; Quattrone et al. 1995; Ohta et al. 1996). For example, neoplastic reversion was obtained using a ribozyme targeted to an H-ras mutation in bladder carcinoma cells (Feng et al. 1995). Ribozymes have also been proposed as a means of both inhibiting gene expression of a mutant gene and of correcting the mutant by targeted trans-splicing (Sullenger and Cech 1994; Jones et al. 1996). Ribozymes can be designed to elicit autocatalytic cleavage of RNA targets; however, the inhibitory effect of some ribozymes may be due in part to an antisense effect due to the antisense sequences flanking the catalytic core that specify the target site (Ellis and Rodgers 1993; Jankowsky and Schwenzer 1996). Ribozyme activity may be augmented by the use of, for example, non-specific nucleic acid binding proteins or facilitator oligonucleotides (Herschlag et al. 1994; Jankowsky and Schwenzer 1996). Multitarget ribozymes (connected or shotgun) have been suggested as a means of improving efficiency of ribozymes for gene suppression (Ohkawa et al. 1993). Triple helix approaches have also been investigated for sequence-specific gene suppression—triplex forming oligonucleotides have been found in some cases to bind in a sequence-specific manner (Postel et al. 1991; Duval-Valentin et al. 1992; Hardenbol and Van Dyke 1996; Porumb et al. 1996). Similarly, peptide nucleic acids have been shown to inhibit gene expression (Hanvey et al. 1992; Knudson and Nielsen 1996; Taylor et al. 1997). Minor groove binding polyamides can bind in a sequence-specific manner to DNA targets and hence may represent useful small molecules for future suppression at the DNA level (Trauger et al. 1996). In addition, suppression has been achieved by interference at the protein level using dominant negative mutant peptides and antibodies (Herskowitz 1987; Rimsky et al. 1989; Wright et al. 1989). In some cases suppression strategies have lead to a reduction in RNA levels without a concomitant reduction in proteins, whereas in others, reductions in RNA have been mirrored by reductions in protein.

SUMMARY OF THE INVENTION

To circumvent difficulties associated with specifically targeting a disease mutation and with the genetic heterogeneity present in inherited disorders, a novel strategy for gene suppression and gene replacement exploiting the degeneracy of the genetic code is described. The invention allows flexibility in choice of target sequence for suppression and provides a means of gene suppression that is independent of the disease mutation.

In summary, the invention involves gene suppression of disease and normal alleles targeting coding sequences in a gene and, when necessary, gene replacement such that the replacement gene cannot be suppressed. Replacement genes are modified at third base positions (wobble positions) so that they code for the correct amino acids but are protected completely or partially from suppression. The same suppression and replacement steps can be used for many disease mutations in a given gene. Suppression and replacement can be undertaken in conjunction with each other or separately.

The invention relates to a strategy for suppressing a gene or disease allele using methods that do not target the disease allele specifically but instead can be targeted towards a broad range of sequences in a particular gene. A particular embodiment of the invention is the use of suppression strategies to target either the disease or normal alleles alone or to target both disease and normal alleles. A further embodiment of the invention is the use of the wobble hypothesis to enable continued expression of a replacement normal or beneficial gene (a gene modified from the wild type such that it provides an additional beneficial effect(s)). The replacement gene will have nucleotide changes from the endogenous wild type gene but will code for identical amino acids as the wild type gene. The strategy circumvents the need for a specific therapy for every mutation within a given gene. In addition, the invention allows greater flexibility in choice of target sequence for suppression of a disease allele.

The invention also relates to a medicament or medicaments for use in suppressing a deleterious allele that is present in a genome of one or more individuals or animals.

Generally, the present invention will be useful where the gene, which is naturally present in the genome of a patient, contributes to a disease state. Generally, one allele of the gene in question will be mutated, that is, will possess alterations in its nucleotide sequence that affects the function or level of the gene product. For example, the alteration may result in an altered protein product from the wild type gene or altered control of transcription and processing. Inheritance or somatic acquisition of such a mutation can give rise to a disease phenotype or can predispose an individual to a disease phenotype. However the gene of interest could also be of wild type phenotype, but contribute to a disease state in another way such that the suppression of the gene would alleviate or improve the disease state or improve the effectiveness of an administered therapeutic compound.

Generally, suppression effectors such as nucleic acids—antisense or sense, ribozymes, peptide nucleic acids (PNAs), triple helix forming oligonucleotides, peptides and/or antibodies directed to sequences in a gene, in transcripts or in protein, can be employed in the invention to achieve gene suppression.

DETAILED DESCRIPTION OF THE INVENTION

The invention addresses shortcomings of the prior art by providing a novel approach to the design of suppression effectors directed to target alleles of a gene carrying a deleterious mutation. Suppression of every mutation giving rise to a disease phenotype may be costly and problematic. Disease mutations are often single nucleotide changes. As a result differentiating between the disease and normal alleles may be difficult. Some suppression effectors require specific sequence targets, for example, hammerhead ribozymes cleave at NUX sites and hence may not be able to target many mutations. Notably, the wide spectrum of mutations observed in many diseases adds additional complexity to the development of therapeutic strategies for such disorders—some mutations may occur only once in a single patient. A further problem associated with suppression is the high level of homology present in coding sequences between members of some gene families. This can limit the range of target sites for suppression that will enable specific suppression of a single member of such a gene family.

The present invention circumvents shortcomings in the prior art by utilising the degeneracy of the genetic code. In the invention suppression effectors are designed specifically to sequences in coding regions of genes or in gene products. Typically, one allele of the gene contains a mutation with a deleterious effect. Suppression targeted to coding sequences provides greater flexibility in choice of target sequence for suppression in contrast to suppression directed towards single disease mutations. Additionally, the invention provides for the introduction of a replacement gene with modified sequences such that the replacement gene is protected from suppression. The replacement gene is modified at third base wobble positions and hence provides the wild type gene product. Notably, the invention has the advantage that the same suppression strategy could be used to suppress, in principle, many mutations in a gene. This is particularly relevant when large numbers of mutations within a single gene cause disease pathology. The replacement gene provides (when necessary) expression of the normal protein product when required to ameliorate pathology associated with reduced levels of wild type protein. The same replacement gene could in principle be used in conjunction with the suppression of many different disease mutations within a given gene. Target sequences may be found in any part of the coding sequence. Suppression in coding sequence holds the advantage that such sequences are present in both precursor and mature RNAs, thereby enabling suppressors to target all forms of RNA.

There is now an armament with which to obtain gene suppression. This, in conjunction with a better understanding of the molecular aetiology of disease, results in an ever increasing number of disease targets for therapies based on suppression. In many cases, complete suppression of gene expression has been difficult to achieve. Possibly a combined approach using a number of suppression effectors may aid in this. For some disorders it may be necessary to block expression of a disease allele completely to prevent disease symptoms whereas for others low levels of mutant protein may be tolerated. In parallel with an increased knowledge of the molecular defects causing disease has been the realisation that many disorders are genetically heterogeneous. Examples in which multiple genes and/or multiple mutations within a gene can give rise to a similar disease phenotype include osteogenesis imperfecta, familial hypercholesterolemia, retinitis pigmentosa, and many others. The utility of the degeneracy of the genetic code (wobble hypothesis) to enable suppression of one or both alleles of a gene and the introduction of a replacement gene such that it escapes suppression has been exploited in the invention. According to the present invention there is provided a strategy for suppressing expression of an endogenous gene with a deleterious mutation, wherein said strategy comprises providing suppression effectors such as antisense nucleic acids able to bind to sequences of a gene to be suppressed, to prevent the functional expression thereof.

Generally the term suppression effectors means nucleic acids, peptide nucleic acids (PNAs), peptides, antibodies or modified forms of these used to silence or reduce gene expression in a sequence specific manner.

Suppression effectors, such as antisense nucleic acids can be DNA or RNA, can typically be directed to coding sequence; however suppression effectors can be targeted to coding sequence and can also be targeted to 5' and/or 3' untranslated regions and/or introns and/or control regions and/or sequences adjacent to a gene or to any combination of such regions of a gene. Antisense nucleic acids including both coding and non-coding sequence can be used if required to help to optimise suppression. Binding of the suppression effector(s) prevents or lowers functional expression of the endogenous gene.

Generally the term 'functional expression' means the expression of a gene product able to function in a manner equivalent to, or better than, a wild type product. In the case of a mutant gene or predisposing gene 'functional expression' means the expression of a gene product whose presence gives rise to a deleterious effect or predisposes to a deleterious effect. By deleterious effect is meant giving rise to or predisposing to disease pathology or altering the effect(s) and/or efficiency of an administered compound.

In a particular embodiment of the invention the strategy further employs ribozymes that can be designed to elicit cleavage of target RNAs. The strategy further employs nucleotides that form triple helix DNA. The strategy can employ peptide nucleic acids for suppression. Nucleic acids for antisense, ribozymes, triple helix forming DNA and peptide nucleic acids may be modified to increase stability, binding efficiencies and uptake. Nucleic acids can be incorporated into a vector. Vectors include naked DNA, DNA plasmid vectors, RNA or DNA virus vectors, lipids, polymers or other derivatives and compounds to aid gene delivery and expression.

The invention further provides the use of antisense nucleotides, ribozymes, PNAs, triple helix nucleotides, or other suppression effectors alone or in a vector or vectors, wherein the nucleic acids are able to bind specifically or partially specifically to coding sequences of a gene to prevent or reduce the functional expression thereof, in the preparation of a medicament for the treatment of an autosomal dominant or polygenic disease or to increase the utility and/or action of an administered compound.

In a further embodiment of the invention, target sequences for suppression can include non-coding sequences of the gene.

According to the present invention there is provided a strategy for suppressing specifically or partially specifically an endogenous gene and (if required) introducing a replacement gene, said strategy comprising the steps of:
1. providing nucleic acids or other suppression effectors able to bind to an endogenous gene, gene transcript or gene product to be suppressed and
2. providing genomic DNA or cDNA (complete or partial) encoding a replacement gene wherein the nucleic acids are unable to bind to equivalent regions in the genomic DNA or cDNA to prevent expression of the replacement gene. The replacement nucleic acids will not be recognised by suppression nucleic acids or will be recognised less effectively than the endogenous gene. The coding sequence of replacement nucleic acids can be altered to prevent or reduce efficiency of suppression. Replacement nucleic acids have modifications in one or more third base (wobble) positions such that replacement nucleic acids still code for the wild type or equivalent amino acids.

In a particular embodiment of the invention there is provided a strategy for gene suppression targeted to coding sequences of the gene to be suppressed.

Suppression will be specific or partially specific to one allele, for example, to the allele carrying a deleterious mutation. Suppressors are targeted to coding regions of a gene or to a combination of coding and non-coding regions of a gene. Suppressors can be targeted to a characteristic of one allele of a gene such that suppression is specific or partially specific to one allele of a gene (PCT/GB97/00574). The invention further provides for use of replacement nucleic acids with altered coding sequences such that replacement nucleic acids will not be recognised (or will be recognised less effectively) by suppression nucleic acids that are targeted specifically or partially specifically to one allele of the gene to be suppressed. Replacement nucleic acids provide the wild type gene product, an equivalent gene product or an improved gene product but are protected completely or partially from suppression effectors targeted to coding sequences.

In a further embodiment of the invention, replacement nucleic acids are provided such that replacement nucleic acids will not be recognised by naturally occurring suppressors found to inhibit or reduce gene expression in one or more individuals, animals or plants. The invention provides for use of replacement nucleic acids that have altered sequences targeted by suppressors of the gene such that suppression by naturally occurring suppressors is completely or partially prevented.

In an additional embodiment of the invention, there is provided replacement nucleic acids with altered nucleotide sequence in coding regions such that replacement nucleic acids code for a product with one or more altered amino acids. Replacement nucleic acids provide a gene product that is equivalent to or improved compared with the naturally occurring endogenous wild type gene product.

In an additional embodiment of the invention there is provided a strategy to suppress a gene where the gene transcript or gene product interferes with the action of an administered compound.

The invention further provides the use of a vector or vectors containing suppression effectors in the form of nucleic acids, said nucleic acids being directed towards coding sequences or combinations of coding and non-coding sequences of the target gene and vector(s) containing genomic DNA or cDNA encoding a replacement gene sequence to which nucleic acids for suppression are unable to bind (or bind less efficiently), in the preparation of a combined medicament for the treatment of an autosomal dominant or polygenic disease. Nucleic acids for suppression or replacement gene nucleic acids may be provided in the same vector or in separate vectors. Nucleic acids for suppression or replacement gene nucleic acids may be provided as a combination of nucleic acids alone or in vectors.

The invention further provides a method of treatment for a disease caused by an endogenous mutant gene, said method comprising sequential or concomitant introduction of
(a) nucleic acids to the coding regions of a gene to be suppressed and/or nucleic acids to coding regions and any combination of 5' and/or 3' untranslated regions, intronic regions, control regions or regions adjacent to a gene to be suppressed
(b) replacement nucleic acids with sequences that allow the replacement gene to be expressed.

The nucleic acid for gene suppression can be administered before, after or at the same time as the replacement gene is administered.

The invention further provides a kit for use in the treatment of a disease caused by a deleterious mutation in a gene, the kit comprising nucleic acids for suppression able to bind to the gene to be suppressed and if required a replacement nucleic acid to replace the mutant gene having sequence that allows it to be expressed and completely or partially escape suppression.

Nucleotides can be administered as naked DNA or RNA. Nucleotides can be delivered in vectors. Naked nucleic acids or nucleic acids in vectors can be delivered with lipids or other derivatives which aid gene delivery. Nucleotides may be modified to render them more stable, for example, resistant to cellular nucleases while still supporting RNase H mediated degradation of RNA or with increased binding efficiencies. Antibodies or peptides can be generated to target the protein product from the gene to be suppressed.

The strategy described herein has applications for alleviating autosomal dominant diseases. Complete silencing of a disease allele may be difficult to achieve using antisense, PNA, ribozyme and triple helix approaches or any combination of gene silencing approaches. However small quantities of mutant product may be tolerated in some autosomal dominant disorders. In others a significant reduction in the proportion of mutant to normal product may result in an amelioration of disease symptoms. Hence, this invention may be applied to any autosomal dominantly or polygenically inherited disease in man where the molecular basis of the disease has been established or is partially understood. This strategy enables the same therapy to be used to treat a range of different disease mutations within the same gene. The development of such approaches is important to future therapies for autosomal dominant and polygenic diseases, the key to a general strategy being that it circumvents the need for a specific therapy for every mutation causing or predisposing to a disease. This is particularly relevant in some disorders, for example, rhodopsin linked autosomal dominant RP, in which to date about one hundred different mutations in the rhodopsin gene have been observed in adRP patients. Likewise, hundreds of mutations have been identified in the human type I Collagen 1A1 and 1A2 genes in autosomal dominant osteogenesis imperfecta. Costs of developing therapies for each mutation are prohibitive at present. Inventions such as this using a general approach for therapy will be required. General approaches may be targeted to the primary defect, as is the case with this invention, or to secondary effects such as apoptosis.

This invention may be applied in gene therapy approaches for biologically important polygenic disorders affecting large proportions of the world's populations such as age related macular degeneration, glaucoma, manic depression, cancers having a familial component and indeed many others. Polygenic diseases require inheritance of more than one mutation (component) to give rise to the disease state. Notably an amelioration in disease symptoms may require reduction in the presence of only one of these components, that is, suppression of one genotype which, together with others leads to the disease phenotype, may be sufficient to prevent or ameliorate symptoms of the disease. In some cases suppression of more than one component may be required to improve disease symptoms. This invention may be applied in possible future interventive therapies for common polygenic diseases to suppress a particular genotype(s) using suppression and, when necessary, replacement steps.

The present invention is exemplified using four genes: human rhodopsin, mouse rhodopsin, human peripherin and human collagen 1A2. The first of these genes are retinal specific. In contrast, collagen 1A2 is expressed in a range of tissues including skin and bone. While these four genes have been used as examples there is no reason why the invention could not be deployed in the suppression of many other genes in which mutations cause or predispose to a deleterious effect. Many examples of mutant genes that give rise to disease phenotypes are available from the prior art—these genes all represent targets for the invention. The present invention is exemplified using hammerhead ribozymes with antisense arms to elicit RNA cleavage. There is no reason why other suppression effectors directed towards genes, gene transcripts or gene products could not be used to achieve gene suppression. Many examples from the prior art detailing use of suppression effectors such as, inter alia, antisense RNA/DNA, triple helix forming DNA, PNAs and peptides to achieve suppression of gene expression are reported. The present invention is exemplified using hammerhead ribozymes with antisense arms to elicit sequence specific cleavage of transcripts from genes implicated in dominant disorders and non-cleavage of transcripts from replacement genes containing sequence modifications in wobble positions such that the replacement gene still codes for wild type protein. The present invention is exemplified using suppression effectors targeting sites in coding regions of the human and mouse rhodopsin, human peripherin and human collagen 1A2 genes. Target sites, which include sequences from transcribed but untranslated regions of genes, introns, regions involved in the control of gene expression, regions adjacent to the gene or any combination of these, could be used to achieve gene suppression. Multiple suppression effectors, for example, shotgun ribozymes could be used to optimise efficiency of suppression when necessary. Additionally, when required, expression of a modified replacement gene such that the replacement gene product is altered from the wild type product such that it provides a beneficial effect may be used to provide gene product.

Materials and Methods

Cloning Vectors cDNA templates and ribozymes were cloned into commercial expression vectors (pCDNA3, pZeoSV or pBluescript) that enable expression in a test tube from T7, T3 or SP6 promoters or expression in mammalian cells from CMV or SV40 promoters. DNA inserts were cloned into the multiple cloning site (MCS) of these vectors typically at or near the terminal ends of the MCS to delete most of the MCS and thereby prevent any possible problems with efficiency of expression subsequent to cloning.

Sequencing Protocols

Clones containing template cDNAs and ribozymes were sequenced by ABI automated sequencing machinery using standard protocols.

Expression of RNAs

RNA was obtained from clones by in vitro transcription using a commercially available Ribomax expression system (Promega) and standard protocols. RNA purifications were undertaken using the Bio-101 RNA purification kit or a solution of 0.3M sodium acetate and 0.2% SDS after isolation from polyacrylamide gels. Cleavage reactions were performed using standard protocols with varying $MgCl_2$ concentrations (0–15 mM) at 37° C., typically for 3 hours. Time points were performed at the predetermined optimal $MgCl_2$ concentrations for up to 5 hours. Radioactively labelled RNA products were obtained by incorporating $\alpha$-$P^{32}$ rUTP (Amersham) in the expression reactions (Gaughan et al. 1995). Labelled RNA products were run on polyacrylamide gels before cleavage reactions were undertaken for the purpose of RNA purification and subsequent to cleavage reactions to establish if RNA cleavage had been achieved. Cleavage reactions were undertaken with 5 mM Tris-HCl pH8.0 and varying concentrations of $MgCl_2$ at 37° C.

RNA Secondary Structures

Predictions of the secondary structures of human and mouse rhodopsin, human peripherin and human collagen 1A2 mRNAs were obtained using the RNAPlotFold program. Ribozymes and antisense were designed to target areas of the RNA that were predicted to be accessible to suppression effectors, for example open loop structures. The integrity of open loop structures was evaluated from the 10 most probable RNA structures. Additionally, predicted RNA structures for truncated RNA products were generated and the integrity of open loops between full length and truncated RNAs compared.

Templates and Ribozymes

Human Rhodopsin

Template cDNA

The human rhodopsin cDNA (SEQ ID NO:1) was cloned into the HindIII and EcoRI sites of the MCS of pCDNA3 in a 5' to 3' orientation allowing subsequent expression of RNA from the T7 or CMV promoter in the vector. The full length 5'UTR sequence was inserted into this clone using primer driven PCR mutagenesis and a HindIII (in pCDNA3) to BstEII (in the coding sequence of the human rhodopsin cDNA) DNA fragment.

cDNA with Altered Sequence at a Wobble Position

The human rhodopsin hybrid cDNA with a single base alteration (SEQ ID NO:2), a C-->G change (at nucleotide 271 of SEQ ID NO:2) was introduced into human rhodopsin cDNA, using a HindIII to BstEII PCR cassette, by primer directed PCR mutagenesis. This sequence change occurs at a silent position—it does not give rise to an amino acid substitution—however it eliminates the ribozyme cleavage site (GUX-->GUG). The hybrid rhodopsin was cloned into pCDNA3 in a 5' to 3' orientation allowing subsequent expression of RNA from the T7 or CMV promoter in the vector.

Rhodopsin cDNA Carrying a Pro23Leu adRP Mutation

A human rhodopsin adRP mutation, a C-->T change (at codon 23; nucleotide 217 of SEQ ID NO:3) was introduced into human rhodopsin cDNA, using a HindIII to BstEII PCR cassette by primer directed PCR mutagenesis. This sequence change results in the substitution of a Proline for a Leucine residue. Additionally the nucleotide change creates a ribozyme cleavage site (CCC-->CTC) (nucleotide 216–218 of SEQ ID NO:3). The mutated rhodopsin nucleic acid sequence was cloned into the HindIII and EcoRI sites of pCDNA3 in a 5' to 3' orientation allowing subsequent expression of RNA from the T7 or CMV promoter in the vector (SEQ ID NO:3).

Ribozyme Constructs

A hammerhead ribozyme (termed Rz10 (SEQ ID NO:29) designed to target a large conserved open loop structure in the RNA from the coding regions of the gene was cloned subsequent to synthesis and annealing into the HindIII and XbaI sites of pCDNA3 again allowing expression of RNA from the T7 or CMV promoter in the vector (SEQ ID NO:4). The target site was GUC (the GUX rule) at position 475–477 (nucleotides 369–371 of SEQ ID NO:1) of the human rhodopsin sequence. Note there is a one base mismatch in one antisense arm of Rz10. A hammerhead ribozyme (termed Rz20 (SEQ ID NO:30) designed to target an open loop structure in RNA from the coding region of a mutant rhodopsin gene with a Pro23Leu mutation was cloned subsequent to synthesis and annealing into the HindIII and XbaI sites of pCDNA3 again allowing expression of RNA from the T7 or CMV promoter in the vector (SEQ ID NO:5). The target site was CTC (the NUX rule) at codon 23 (nucleotides 216–218 of SEQ ID NO:3) of the human rhodopsin sequence (Accession number: K02281). Antisense flanks are underlined.

```
Rz10: GGTCGGTCTGATGAGTCCGTGAGGACGAAACGTAGAG (SEQ ID NO:29;
       nucleotides 101-137 of SEQ ID NO:4)
Rz20: TACTCGAACTGATGAGTCCGTGAGGACGAAAGGCTGC (SEQ ID NO:30;
       nucleotides 104-140 of SEQ ID NO:5)
```

Mouse Rhodopsin

Template cDNA

The full length mouse rhodopsin cDNA was cloned into the EcoRI sites of the MCS of pCDNA3 in a 5' to 3' orientation allowing subsequent expression of RNA from the T7 or CMV promoter in the vector (SEQ ID NO:6).

cDNA with Altered Sequence at a Wobble Position

The mouse rhodopsin hybrid cDNA with a single base alteration, a T-->C change (at position 1460) (nucleotide 190 of SEQ ID NO:7) was introduced into mouse rhodopsin cDNA, using a HindIII to Eco47III PCR cassette, by primer directed PCR mutagenesis. This sequence change occurs at a silent position—it does not give rise to an amino acid substitution—however it eliminates the ribozyme cleavage site (TTT-->TCT) (nucleotides 189–191 of SEQ ID NO:7). The hybrid rhodopsin was cloned into pCDNA3 in a 5' to 3' orientation allowing subsequent expression of RNA from the T7 or CMV promoter in the vector (SEQ ID NO:7).

Ribozyme Constructs

A hammerhead ribozyme (termed Rz33) (SEQ ID NO:31) designed to target a large robust open loop structure in the RNA from the coding regions of the gene was cloned subsequent to synthesis and annealing into the HindIII and XbaI sites of pCDNA3 again allowing expression of RNA from the T7 or CMV promoter in the vector (SEQ ID NO:8). The target site was TTT (the NUX rule) at position 1459–1461 (nucleotides 405–407 of SEQ ID NO:6) of the mouse rhodopsin sequence. (Accession number: M55171). Antisense flanks are underlined.

Rz33: GGCACATCTGATGAGTCCGTGAGGAC-GAAAAAATTGG (SEQ ID NO:31; nucleotides 118–154 of SEQ ID NO:8).

Human Peripherin

Template cDNA

The full length human peripherin cDNA was cloned into the EcoRI sites of the MCS of pCDNA3 in a 5' to 3' orientation allowing subsequent expression of RNA from the T7 or CMV promoter in the vector (SEQ ID NO:9).

DNAs with Altered Sequence at a Wobble Position

A human peripherin hybrid DNA with a single base alteration, a A-->G change (at position 257) (nucleotide 332 of SEQ ID NO:10) was introduced into human peripherin DNA by primer directed PCR mutagenesis (forward 257 mutation primer—5'CATGGCGCTGCTGAAAGTCA3' (SEQ ID NO:11)—the reverse 257 primer was complementary to the forward primer). This sequence change occurs at a silent position—it does not give rise to an amino acid substitution—however it eliminates the ribozyme cleavage site (CTA-->CTG)(nucleotide 330–332 of SEQ ID NO:10). A second human peripherin hybrid DNA with a single base alteration, a A-->G change (at position 359) (nucleotide 468 of SEQ ID NO:13) was introduced into human peripherin DNA, again by primer directed PCR mutagenesis (forward 359 mutation primer—5'CATCTTCAGCCTGGGACTGT3' (SEQ ID NO:12)—the reverse 359 primer was complementary to the forward primer) (SEQ ID NO:12). Similarly this sequence change occurs at a silent position—it does not give rise to an amino acid substitution—however again it eliminates the ribozyme cleavage site (CTA-->CTG) (nucleotides 466–468 of SEQ ID NO:13). The ribozyme cleavage sites at 255–257 (nucleotides 330–332 of SEQ ID NO:10) and 357–359 (nucleotides 466–468 of SEQ ID NO:13) occur at different open loop structures as predicted by the RNAPlotFold program. Hybrid peripherin DNAs included the T7 promoter sequence allowing subsequent expression of RNA.

Ribozyme Constructs

Hammerhead ribozymes (termed Rz30 and Rz31)(SEQ ID NOs: 32 and 33, respectively), designed to target robust open loop structures in the RNA from the coding regions of the gene, were cloned subsequent to synthesis and annealing into the HindIII and XbaI sites of pCDNA3 again allowing expression of RNA from the T7 or CMV promoter in the vector (SEQ ID NOS:14 and 15, respectively). The target sites were both CTA (the NUX rule) at positions 255–257 and 357–359 respectively of the human peripherin sequence. (Accession number: M73531). Antisense flanks are underlined.

```
Rz30: ACTTTCAGCTGATGAGTCCGTGAGGACGAAAGCGCCA (SEQ ID NO:32;
nucleotides 116-153 of SEQ ID NO:14)
Rz31: ACAGTCCCTGATGAGTCCGTGAGGACGAAAGGCTGAA (SEQ ID NO:33;
nucleotides 112-148 of SEQ ID NO:15)
```

Human Type I Collagen—COL1A2

Template cDNA

A human type I collagen 1A2 cDNA was obtained from the ATCC (Accession No: Y00724). A naturally occurring polymorphism has previously been found in collagen 1A2 at positions 907 of the gene involving a T-->A nucleotide change (Filie et al. 1993). The polymorphism occurs in a predicted open loop structure of human collagen 1A2 RNA. Polymorphic variants of human collagen 1A2 were generated by PCR directed mutagenesis, using a HindIII to XbaI PCR cassette. Resulting clones contained the following polymorphism: collagen 1A2 (A) has a T nucleotide at position 907 (A nucleotide 176 of SEQ ID NO:17, reverse strand). In contrast human collagen 1A2 (B) has an A nucleotide at position 907 (T nucleotide 181 of SEQ ID NO:16, reverse strand). In collagen 1A2 (A) there is a ribozyme target site, that is a GTC site (906–908) (nucleotides 175–177 of SEQ ID NO:17, reverse strand), however this cleavage site is lost in collagen 1A2 (B) as the sequence is altered to GAC (906–908) (nucleotides 180–182 of SEQ ID NO:16, reverse strand), thereby disrupting the ribozyme target site.

Ribozyme Constructs

A hammerhead ribozyme (termed Rz907) (SEQ ID NO:34) was designed to target a predicted open loop structure in the RNA from the coding region of the polymorphic variant of the human collagen 1A2 gene. Rz907 oligonucleotide primers were synthesised, annealed and cloned into the HindIII and XbaI sites of pCDNA3 again allowing subsequent expression of RNA from the T7 or CMV promoter in the vector (SEQ ID NO:18). The target site was a GUX site at position 906–908 of the human type I collagen 1A2 sequence (Accession number: Y00724). Antisense flanks are underlined.

Rz907: <u>CGGCGG</u>CTGATGAGTCCGTGAGGACGAA<u>ACCAGCA</u> (SEQ ID NO:34; nucleotide 107–141 of SEQ ID NO:18).

FIGURE LEGENDS

FIG. 1:

pBR322 was cut with MspI, radioactively labelled and run on a polyacrylamide gel to enable separation of the resulting DNA fragments. The sizes of these fragments are given in FIG. 1. This DNA ladder was then used on subsequent polyacrylamide gels (4–8%) to provide an estimate of the size of the RNA products run on the gels. However there is a significant difference in mobility between DNA and RNA depending on the percentage of polyacrylamide and the gel running conditions—hence the marker provides an estimate of size of transcripts.

FIG. 2:

A: Human rhodopsin cDNA (SEQ ID NO:1) was expressed from the T7 promoter to the BstEII site in the coding sequence. Resulting RNA was mixed with Rz10RNA in 15 mM magnesium chloride and incubated at 37° C. for varying times. Lanes 1–4: Human rhodopsin RNA and Rz10RNA after incubation at 37° C. with 15 mM magnesium chloride for 0, 1 2 and 3 hours respectively. Sizes of the expressed RNAs and cleavage products are as expected (Table 1). Complete cleavage of human rhodopsin RNA was obtained with a small residual amount of intact RNA present at 1 hour. Lane 6 is intact unadapted human rhodopsin RNA (BstEII) alone. Lane 5 is unadapted human rhodopsin RNA (FspI) alone and refers to FIG. 2B. From top to bottom, human rhodopsin RNA and the two cleavage products from this RNA are highlighted with arrows.

B: The unadapted human rhodopsin cDNA was expressed from the T7 promoter to the FspI site in the coding sequence. The adapted human rhodopsin cDNA was expressed from the T7 promoter to the BstEII site in the coding sequence. Lanes 1–4: Resulting RNAs were mixed together with Rz10 and 15 mM magnesium chloride and incubated at 37° C. for varying times (0, 1, 2 and 3 hours respectively). The smaller unadapted rhodopsin transcripts were cleaved by Rz10 while the larger adapted transcripts were protected from cleavage by Rz10. Cleavage of adapted protected transcripts would have resulted in products of 564 bases and 287 bases—the 564 bases product clearly is not present—the 287 bp product is also generated by cleavage of the unadapted human rhodopsin transcripts and hence is present (FspI). After 3 hours the majority of the unadapted rhodopsin transcripts has been cleaved by Rz10. Lane 5 contains the intact adapted human rhodopsin RNA (BstEII) alone. From top to bottom adapted uncleaved human rhodopsin transcripts, residual unadapted uncleaved human rhodopsin transcripts and the larger of the cleavage products from unadapted human rhodopsin transcripts are highlighted by arrows. The smaller 22 bases cleavage product from the unadapted human rhodopsin transcripts has run off the gel.

FIG. 3:

A: Unadapted (SEQ ID NO:1) and adapted (SEQ ID NO:2) human rhodopsin cDNAs were expressed from the T7 promoter to the AcyI after the coding sequence and the BstEII site in the coding sequence respectively. Sizes of expressed RNAs and cleavage products were as predicted (Table 1). Resulting RNAs were mixed together with Rz10 RNA at varying magnesium chloride concentrations and incubated at 37° C. for 3 hours. Lane 1: Intact unadapted human rhodopsin RNA (AcyI) alone. Lanes 2–5: Unadapted and adapted human rhodopsin RNAs and Rz10 RNA after incubation at 37° C. with 0, 5, 10 and 15 mM MgCl$_2$ respectively. Almost complete cleavage of the larger unadapted human rhodopsin RNA was obtained with a small residual amount of intact RNA present at 5 mM MgCl$_2$. In contrast the adapted human rhodopsin RNA remained intact. From top to bottom, the unadapted and adapted rhodopsin RNAs, and two cleavage products from the unadapted human rhodopsin RNA are highlighted by arrows. Lane 6 is intact adapted human rhodopsin RNA (BstEII) alone.

B: The adapted human rhodopsin cDNA was expressed from the T7 promoter to the BstEII site in the coding sequence. Lanes 1–4: Resulting RNA was mixed together with Rz10 and 0, 5, 10 and 15 mM magnesium chloride and incubated at 37° C. for 3 hours respectively. The adapted rhodopsin transcripts were not cleaved by Rz10. Cleavage of adapted transcripts would have resulted in cleavage products of 564 bases and 287 bases which clearly are not present. Lane 5: intact adapted human rhodopsin RNA (BstEII) alone. Lane 4: RNA is absent—due to a loading error or degradation. The adapted uncleaved human rhodopsin RNA is highlighted by an arrow.

C: Unadapted (SEQ ID NO:1) and adapted (SEQ ID NO:2) human rhodopsin cDNAs were expressed from the T7 promoter to the AcyI after the coding sequence and the BstEII site in the coding sequence respectively. Sizes of expressed RNAs and cleavage products were as predicted (Table 1). Resulting RNAs were mixed together with Rz10 RNA at varying magnesium chloride concentrations and incubated at 37° C. for 3 hours. Lane 1: DNA ladder as in FIG. 1. Lanes 2–5: Unadapted and adapted human rhodopsin RNAs and Rz10 RNA after incubation at 37° C. with 0, 5, 10 and 15 mM MgCl$_2$ respectively. Almost complete cleavage of the larger unadapted human rhodopsin RNA was obtained with a small residual amount of intact RNA present at 5 and 10 mM MgCl$_2$. In contrast the adapted human rhodopsin RNA remained intact. Lane 6: Adapted human rhodopsin RNA (BstEII) alone. Lane 7: Unadapted human rhodopsin RNA (AcyI) alone. Lane 8: DNA ladder as in FIG. 1. From top to bottom, the unadapted and adapted rhodopsin RNAs, and two cleavage products from the unadapted human rhodopsin RNA are highlighted by arrows. Separation of the adapted human rhodopsin RNA (851 bases) and the larger of the cleavage products from the unadapted RNA (896 bases) is incomplete in this gel (further running of the gel would be required to achieve separation)—however the separation of these two RNAs is demonstrated in FIG. 3A.

FIG. 4:

The mutant (Pro23Leu) (SEQ ID NO:3) human rhodopsin cDNA was expressed from the T7 promoter to the BstEII in the coding sequence. Likewise the Rz20 clone was expressed to the XbaI site. Resulting RNAs were mixed together with 10 mM magnesium chloride concentrations at 37° C. for varying times. Sizes of expressed RNAs and cleavage products were as predicted (Table 1). Lane 1: DNA ladder as in FIG. 1. Lanes 2: Pro23Leu human rhodopsin RNA alone. Lanes 3–7 Pro23Leu human rhodopsin RNA and Rz20 RNA after incubation at 37° C. with 10 mM MgCl$_2$ for 0 mins, 30 mins, 1 hr, 2 hrs and 5 hrs respectively. Almost complete cleavage of mutant rhodopsin transcripts was obtained with a residual amount of intact RNA left even after 5 hours. Lane 8: DNA ladder as in FIG. 1. From top to bottom, intact mutant rhodopsin RNA and the two cleavage products from the mutant human rhodopsin RNA are highlighted by arrows.

FIG. 5:

The mutant (Pro23Leu) (SEQ ID NO:3) human rhodopsin cDNA was expressed from the T7 promoter to the BstEII in the coding sequence. Likewise the Rz10 clone (SEQ ID NO:4) was expressed to the XbaI site. Resulting RNAs were mixed together with 10 mM magnesium chloride concentrations at 37° C. for varying times. Sizes of expressed RNAs and cleavage products were as predicted (Table 1). Lane 1: DNA ladder as in FIG. 1. Lanes 2: Pro23Leu human rhodopsin RNA alone. Lanes 3–7 Pro23Leu human rhodopsin RNA and Rz10 RNA after incubation at 37° C. with 10 mM $MgCl_2$ for 0 mins, 30 mins, 1 hr, 2 hrs and 5 hrs respectively. Almost complete cleavage of mutant human rhodopsin RNA was obtained with a residual amount of intact RNA remaining even after 5 hours (Lane 7). Lane 8: DNA ladder as in FIG. 1. From top to bottom, intact mutant rhodopsin RNA and the two cleavage products from the mutant human rhodopsin RNA are highlighted by arrows.

FIG. 6:

The mouse rhodopsin cDNA clone was expressed in vitro from the T7 promoter to the Eco47III site in the coding sequence. Likewise the Rz33 clone was expressed to the XbaI site. A: Resulting RNAs were mixed together with 10 mM magnesium chloride at 37° C. for varying times. Sizes of expressed RNAs and cleavage products were as predicted (Table 1). DNA ladder as in FIG. 1. Lane 1: mouse rhodopsin RNA alone. Lanes 2–5 Mouse rhodopsin RNA and Rz33 RNA after incubation at 37° C. with 10 mM $MgCl_2$ at 0, 5, 7.5 and 10 mM $MgCl_2$ respectively for 3 hours. Cleavage of mouse rhodopsin RNA was obtained after addition of divalent ions (Lane 3). Residual uncleaved mouse rhodopsin RNA and the two cleavage products from the mouse rhodopsin RNA are highlighted by arrows. B: The adapted mouse rhodopsin cDNA clone with a base change at position 1460 (nucleotide 190 of SEQ ID NO:7) was expressed in vitro from the T7 promoter to the Eco471II site in the coding sequence. Likewise the Rz33 clone was expressed to the XbaI site. Resulting RNAs were mixed together with various magnesium chloride concentrations at 37° C. for 3 hours. Sizes of the expressed RNAs and cleavage products were as predicted (Table 1). Lane 1: DNA ladder as in FIG. 1. Lane 2: Adapted mouse rhodopsin RNA alone. Lanes 3–6: Adapted mouse rhodopsin RNA and Rz33 RNA after incubation at 37° C. with 0, 5, 7.5 and 10 mM $MgCl_2$ for 3 hours at 37° C. No cleavage of the adapted mouse rhodopsin RNA was observed. The intact adapted mouse rhodopsin RNA is highlighted by an arrow.

FIG. 7:

The human peripherin cDNA clone was expressed in vitro from the T7 promoter to the BglII site in the coding sequence. Likewise Rz30 (targeting a cleavage site at 255–257) was expressed to the XbaI site. A: Resulting RNAs were mixed together with 10 mM magnesium chloride at 37° C. for varying times. Lane 1: DNA ladder as in FIG. 1. Lane 2: Intact human peripherin RNA alone. Lanes 3–7: Human peripherin RNA and Rz30 RNA after incubation at 37° C. with 10 mM $MgCl_2$ for 3 hrs, 2 hrs, 1 hr, 30 mins and 0 mins respectively. Lane 8: DNA ladder as in FIG. 1. From top to bottom, intact human peripherin RNA and the two cleavage products from the human peripherin RNA are highlighted by arrows. B: Resulting RNAs were mixed with Rz30 RNA at varying magnesium chloride concentrations and incubated at 37° C. for 3 hrs. Lane 1: DNA ladder as in FIG. 1. Lanes 2–5: Human peripherin RNA and Rz30 after incubation at 37° C. with 10, 7.5, 5 and 0 mM magnesium chloride respectively for 3 hrs. Lane 6: Intact human peripherin RNA alone. Sizes of the expressed RNAs and cleavage products are as expected (Table 1). Significant cleavage of human peripherin RNA was obtained with a residual amount of intact RNA present at each $MgCl_2$ concentration. From top to bottom, human peripherin RNA and the two cleavage products from this RNA are highlighted with arrows. C: The adapted human peripherin DNA with a single base change at position 257 was expressed from the T7 promoter to the AvrII site in the coding sequence. Resulting RNA was mixed with Rz30 at various magnesium chloride concentrations and incubated at 37° C. for 3 hrs. Lane 1: DNA ladder as in FIG. 1. Lane 2: Intact adapted human peripherin RNA alone. Lanes 3–6: Adapted human peripherin RNA and Rz30 after incubation at 37° C. with 0, 5, 7.5 and 10 mM magnesium chloride respectively for 3 hrs. Lane 7: DNA ladder as in FIG. 1. D: The unadapted human peripherin cDNA and the adapted human peripherin DNA fragment with a single base change at position 257 were expressed from the T7 promoter to the BglII and AvrII sites respectively in the coding sequence. Resulting RNAs were mixed with Rz30 at various magnesium chloride concentrations and incubated at 37° C. for 3 hrs. Lane 1: DNA ladder as in FIG. 1. Lane 2: Intact unadapted human peripherin RNA alone. Lane 3: Intact adapted human peripherin RNA alone. Lanes 4–7: Unadapted and adapted human peripherin RNAs and Rz3 after incubation at 37° C. with 0, 5, 7.5 and 10 mM magnesium chloride respectively for 3 hrs at 37° C. No cleavage of the adapted human peripherin RNA was observed even after 3 hours whereas a significant reduction in the unadapted RNA was observed over the same time frame. Lane 8: DNA ladder as in FIG. 1. From top to bottom, residual unadapted human peripherin RNA, adapted human peripherin RNA and the two cleavage products are highlighted by arrows.

FIG. 8:

Human peripherin cDNA clone was expressed in vitro from the T7 promoter to the BglII site in the coding sequence. Likewise the Rz31 (targeting a cleavage site at 357–359) (nucleotides 466–468 of SEQ ID NO:13) was expressed to the XbaI site. A: Resulting RNAs were mixed together with 10 mM magnesium chloride at 37° C. for varying times. Lane 1: DNA ladder as in FIG. 1. Lanes 2–6: Human peripherin RNA and Rz31 RNA after incubation at 37° C. with 10 mM $MgCl_2$ for 3 hrs, 2 hrs, 1 hr, 30 mins and 0 mins respectively. Increased cleavage of mouse rhodopsin RNA was obtained over time—however significant residual intact RNA remained even after 3 hours (Lane 2). Lane 7: Intact human peripherin RNA alone. Lane 8: DNA ladder as in FIG. 1. From top to bottom, intact human peripherin RNA and the two cleavage products from the human peripherin RNA are highlighted by arrows. B: Resulting RNAs were mixed with Rz31 RNA at varying magnesium chloride concentrations and incubated at 37° C. for 3 hrs. Lane 1: DNA ladder as in FIG. 1. Lanes 2–5: Human peripherin RNA and Rz31 after incubation at 37° C. with 10, 7.5, 5 and 0 mM magnesium chloride respectively for 3 hrs. Sizes of the expressed RNAs and cleavage products are as expected (Table 1). Significant cleavage of human peripherin RNA was obtained with a residual amount of intact RNA present at each $MgCl_2$ concentration (Lanes 2–4). Lane 6: Intact human peripherin RNA alone. Lane 7: DNA ladder as in FIG. 1. From top to bottom, human peripherin RNA and the two cleavage products from this RNA are highlighted with arrows. C: The adapted human peripherin DNA with a single base change at position 359 (nucleotide 468 of SEQ ID NO:13) was expressed from the T7 promoter to the BglII site in the coding sequence. Resulting RNA was mixed with Rz31 at various magnesium chloride concentrations and incubated at 37° C. for 3 hrs. Lane 1: DNA ladder as in FIG. 1. Lane 2: Intact adapted human peripherin RNA alone. Lanes 3–6: Adapted human peripherin RNA and RZ31 after incubation at 37° C. with 0, 5, 7.5 and 10 mM magnesium chloride respectively for 3 hrs. No cleavage of the adapted human peripherin RNA was observed even after 3 hours. Lane 7: DNA ladder as in FIG. 1.

FIG. 9:

A: The human collagen 1A2 cDNA clones containing the A and T alleles of the polymorphism at position 907 were expressed from the T7 promoter to the MvnI and XbaI sites in the insert and vector respectively. Resulting RNAs were mixed together with Rz907 and various MgCl$_2$ concentrations and incubated at 37° C. for 3 hours. Lane 1: intact RNA from the human collagen 1A2 (A) containing the A allele of the 907 polymorphism. Lane 2: intact RNA from the human collagen 1A2 (B) containing the T allele of the 907 polymorphism. Lanes 3–5: Human collagen 1A2 (A) and (B) representing the A and T allele RNAs and Rz907 incubated with 0, 5, and 10 mM MgCl$_2$ at 37° C. for 3 hours. RNA transcripts from the T allele containing the 906–908 target site are cleaved by Rz907 upon addition of divalent ions—almost complete cleavage is obtained with a residual amount of transcript from the T allele remaining (Lane 5). In contrast transcripts expressed from the A allele (which are smaller in size to distinguish between the A (MvnI) and T (XbaI) alleles) were not cleaved by Rz907—no cleavage products were observed. From top to bottom, RNA from the T allele, the A allele and the two cleavage products from the T allele are highlighted by arrows. Lane 6: DNA ladder as in FIG. 1.

B: The human collagen 1A2 cDNA (A)+(B) clones containing the A and T alleles of the polymorphism at 907 were expressed from the T7 promoter to the MvnI and XbaI sites in the insert and vector respectively. Resulting RNAs were mixed together with Rz907 and 10 mM magnesium chloride and incubated at 37° C. for varying times. Lane 1: DNA ladder as in FIG. 1. Lane 2: intact RNA from the human collagen 1A2 (A) with the A allele of the 907 polymorphism. Lane 3: intact RNA from the human collagen 1A2 (B) with the T allele of the 907 polymorphism. Lanes 4–9: Human collagen 1A2 A and T allele RNA and Rz907 incubated with 10 mM MgCl$_2$ at 37° C. for 0, 30 mins, 1 hour, 2 hours, 3 hours and 5 hours respectively. RNA transcripts from the T allele containing the 906–908 target site are cleaved by Rz907—almost complete cleavage is obtained after 5 hours. In contrast transcripts expressed from the A allele (which are smaller in size to distinguish between the A (MvnI) and T (XbaI) alleles) were not cleaved by Rz907—no cleavage products were observed. From top to bottom, RNA from the T allele, the A allele and the two cleavage products from the T allele are highlighted by arrows.

FIG. 10:
The human rhodopsin cDNA in pCDNA3. (SEQ ID NO: 1).

FIG. 11:
The human rhodopsin cDNA in pCDNA3 (SEQ ID NO:2) with a base change at a silent site (477) (nucleotide 271 of SEQ ID NO:2).

FIG. 12:
Mutant (Pro23Leu) (nucleotides 216—218 of SEQ ID NO:3) human rhodopsin cDNA in pCDNA3 (SEQ ID NO:3).

FIG. 13:
Rz10 cloned into pCDNA3 (SEQ ID NO:4). Note there is a one base mismatch in one antisense arm of Rz10.

FIG. 14:
Rz20 cloned into pCDNA3 (SEQ ID NO:5).

FIG. 15:
The mouse rhodopsin cDNA in pCDNA3 (SEQ ID NO:6).

FIG. 16:
The mouse rhodopsin cDNA in pCDNA3 (SEQ ID NO:7) with a base change at a silent site (1460) (nucleotide 190 of SEQ ID NO:7).

FIG. 17:
Rz33 cloned into pCDNA3 (SEQ ID NO:8)

FIG. 18:
The human peripherin cDNA in pCDNA3 (SEQ ID NO:9).

FIG. 19:
The human peripherin DNA fragment (SEQ ID NO:10) with a base change at a silent site (257) (nucleotide 332 of SEQ ID NO:10).

FIG. 20:
The human peripherin DNA fragment (SEQ ID NO:13) with a base change at a silent site (359) (nucleotide 468 of SEQ ID NO:13). The sequence quality was not good in the region of the human peripherin 359 silent change (nucleotide 468 of SEQ ID NO:13)—the sequencing primer was too far from the target site to achieve good quality sequence.

FIG. 21:
Rz30 cloned into pCDNA3 (SEQ ID NO:14)

FIG. 22:
Rz31 cloned into pCDNA3 (SEQ ID NO:15)

FIG. 23:
Collagen 1A2 (A) sequence containing the A polymorphism at position 907. (SEQ ID NO:16) (Note there is an additional polymorphic site at position 902).

FIG. 24:
Collagen 1A2 (B) sequence containing the T polymorphism at position 907. (SEQ ID NO:17) (Note there is an additional polymorphic site at position 902).

FIG. 25:
Rz907 cloned into pCDNA3 (SEQ ID NO:18).

Results

Human and mouse rhodopsin, human peripherin and human collagen 1A2 cDNA clones were expressed in vitro. Ribozymes targeting specific sites in the human and mouse rhodopsin, human peripherin and human collagen 1A2 cDNAs were also expressed in vitro. cDNA clones were cut with various restriction enzymes resulting in the production of differently sized transcripts after expression. This aided in differentiating between RNAs expressed from unadapted and adapted cDNAs. Restriction enzymes used to cut each clone, sizes of resulting transcripts and predicted sizes of products after cleavage by target ribozymes are given below in Table 1. Exact sizes of expression products may vary by a few bases from that estimated as there may be some ambiguity concerning inter alia the specific base at which transcription starts.

EXAMPLE 1

A: Human Rhodopsin

The unadapted human rhodopsin cDNA (SEQ ID NO:1) and the human rhodopsin cDNA with a single nucleotide substitution in the coding sequence (SEQ ID NO:2) were cut with BstEII and expressed in vitro. The single base change occurs at the third base position or wobble position of the codon (at position 477) (nucleotide 271 of SEQ ID NO:2) and therefore does not alter the amino acid coded by this triplet. The Rz10 clone was cut with XbaI and expressed in vitro. Resulting ribozyme and human rhodopsin RNAs were mixed with varying concentrations of MgCl$_2$ to optimise cleavage of template RNA by Rz10. A profile of human rhodopsin RNA cleavage by Rz10 over time is given in FIG.

Figures 2A, 2B:
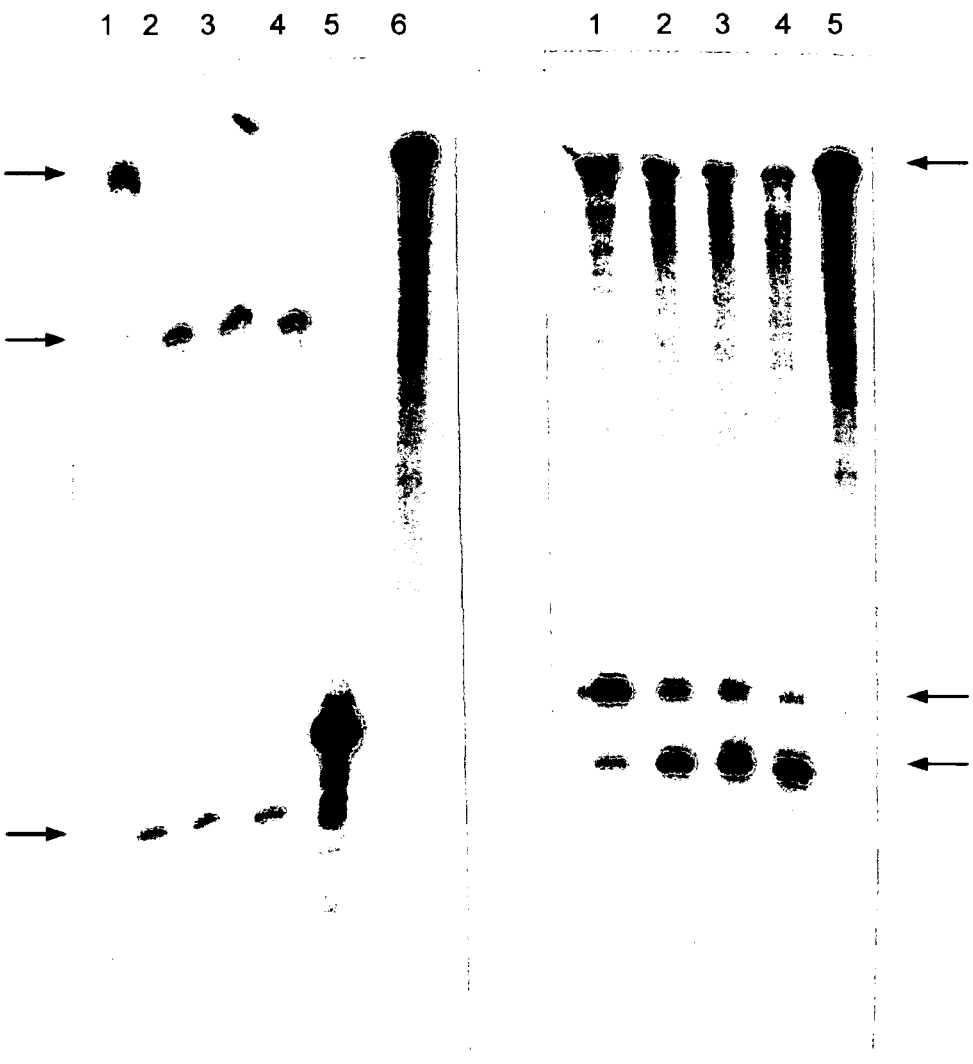
Figures 3A, 3B:
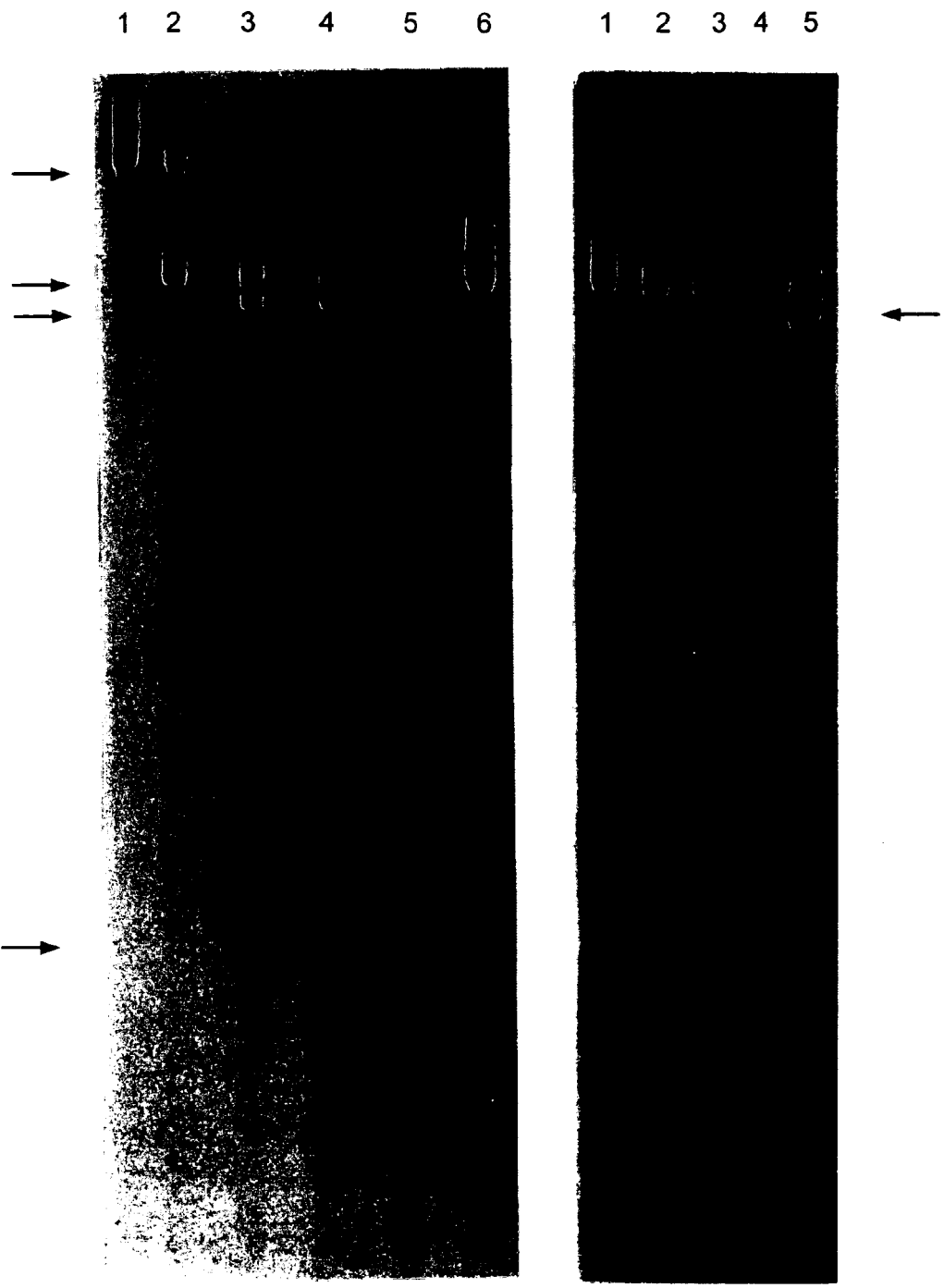
Figure 3C:
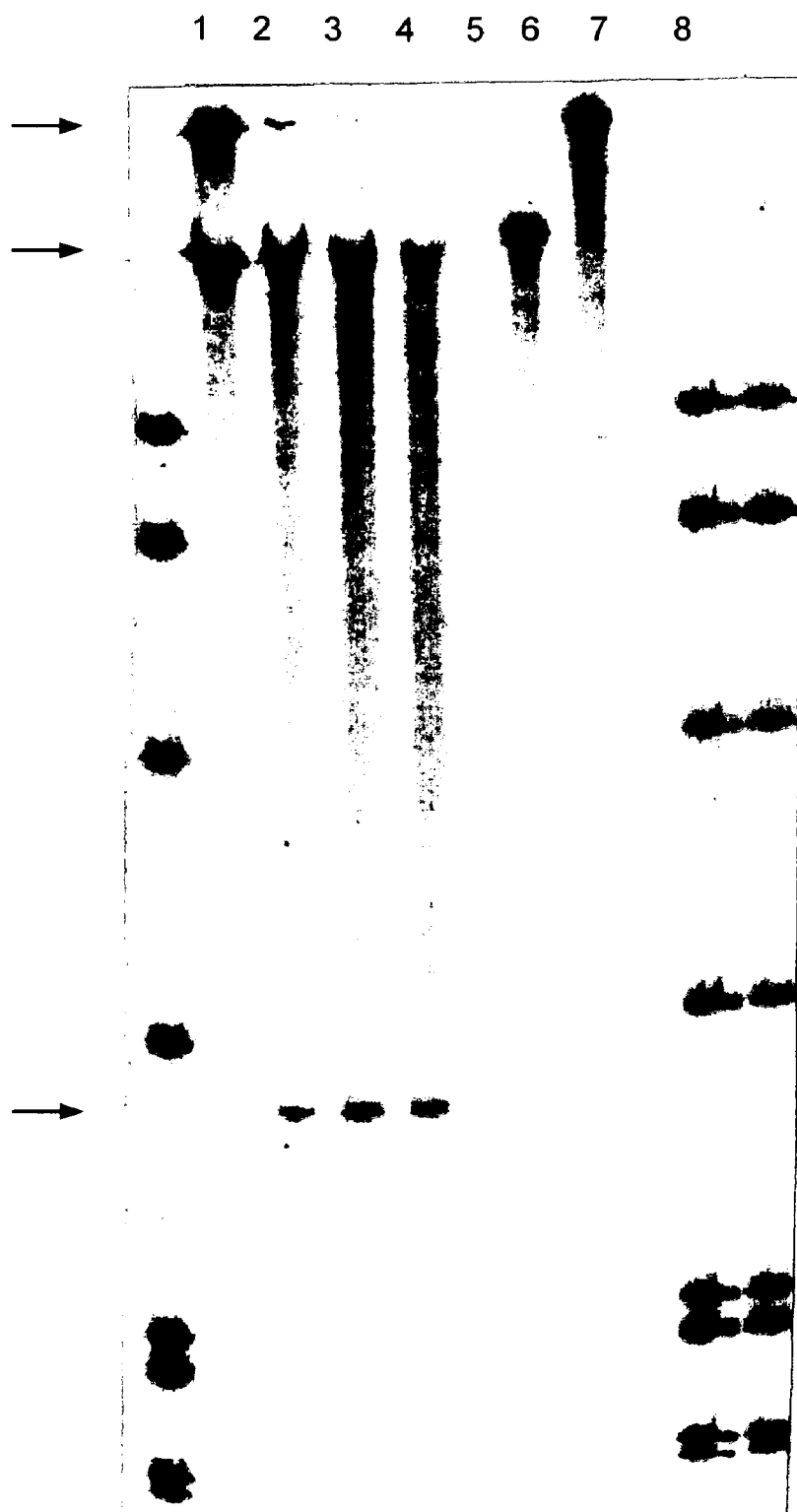

2A. The MgCl$_2$ curve profile used to test if adapted human rhodopsin transcripts could be cleaved by Rz10 is given in FIG. 3B. Unadapted and adapted human rhodopsin cDNAs were cut with FspI and BstEII respectively, expressed and mixed together with Rz10 RNA to test for cleavage (FIG. 2B) over time. Likewise, unadapted and adapted human rhodopsin cDNAs were cut with AcyI and BstEII respectively, both were expressed in vitro and resulting transcripts mixed with Rz10 RNA at varying MgCl$_2$ concentrations to test for cleavage (FIG. 3A, 3C). In all cases expressed RNAs were the predicted size. Similarly in all cases unadapted transcripts were cleaved into products of the predicted size. Cleavage of unadapted human rhodopsin RNA was almost complete—little residual uncleaved RNA remained. In all cases adapted human rhodopsin RNAs with a single base change at a silent site remained intact, that is, they were not cleaved by Rz10. Clearly, transcripts from the unadapted human rhodopsin cDNA are cleaved by Rz10 while transcripts from the adapted replacement gene which has been modified in a manner which exploits the degeneracy of the genetic code are protected from cleavage. It is worth noting that AcyI enzyme cuts after the stop codon and therefore the resulting RNA includes the complete coding sequence of the gene.

B: Human Rhodopsin

Rz20 was cut with XbaI and expressed in vitro. Similarly the rhodopsin cDNA containing a Pro23Leu mutation was cut with BstEII and expressed in vitro.

Figure 4:
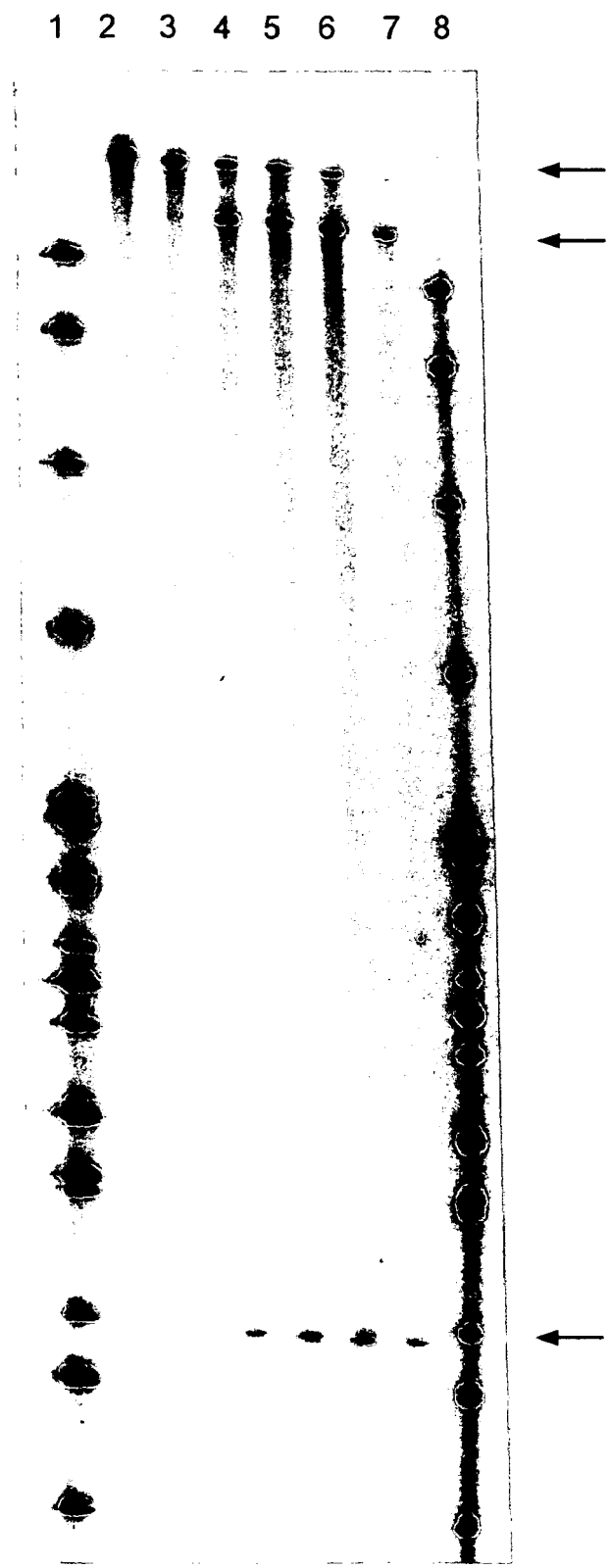
Figure 5:
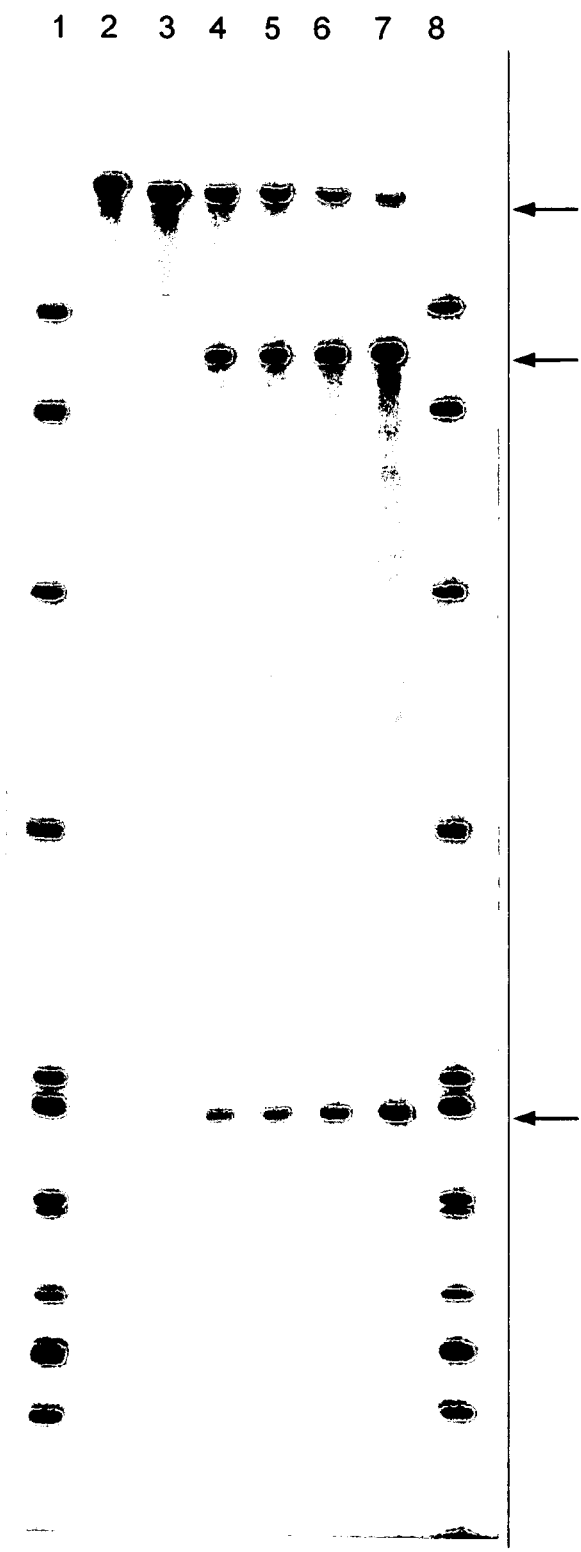

Resulting RNAs were mixed and incubated at 37° C. with 10 mM MgCl$_2$ for varying times. Rz20 was designed to elicit mutation specific cleavage of transcripts containing a Pro23Leu rhodopsin mutation. All expressed products and cleavage products were the correct size. FIG. 4 demonstrates mutation specific cleavage of the mutant RNA over time incubated at 37° C. with 10 mM MgCl$_2$. Cleavage of mutant rhodopsin transcripts by Rz10 which targets a ribozyme cleavage site 3' of the site of the Pro23Leu mutation in rhodopsin coding sequence was explored. The mutant rhodopsin cDNA and Rz10 clones were cut with BstEII and XbaI respectively and expressed in vitro. Resulting RNAs were mixed and incubated with 10 mM MgCl$_2$ for varying times (FIG. 5). All expressed products and cleavage products were the correct size. Rz10 cleaved mutant rhodopsin transcripts. Using a replacement gene with a sequence change around the Rz10 cleavage site which is at a wobble position we demonstrated in Example 1A that transcripts from the replacement gene remain intact due to absence of the Rz10 target site (FIGS. 2B, 3A and 3B). Hence Rz10 could be used to cleave mutant transcripts in a manner independent of the disease mutation itself (that is, using this site) while transcripts from the replacement gene which code for the correct protein would remain intact and therefore could supply the wild type protein.

EXAMPLE 2

Mouse Rhodopsin

Figure 6A:
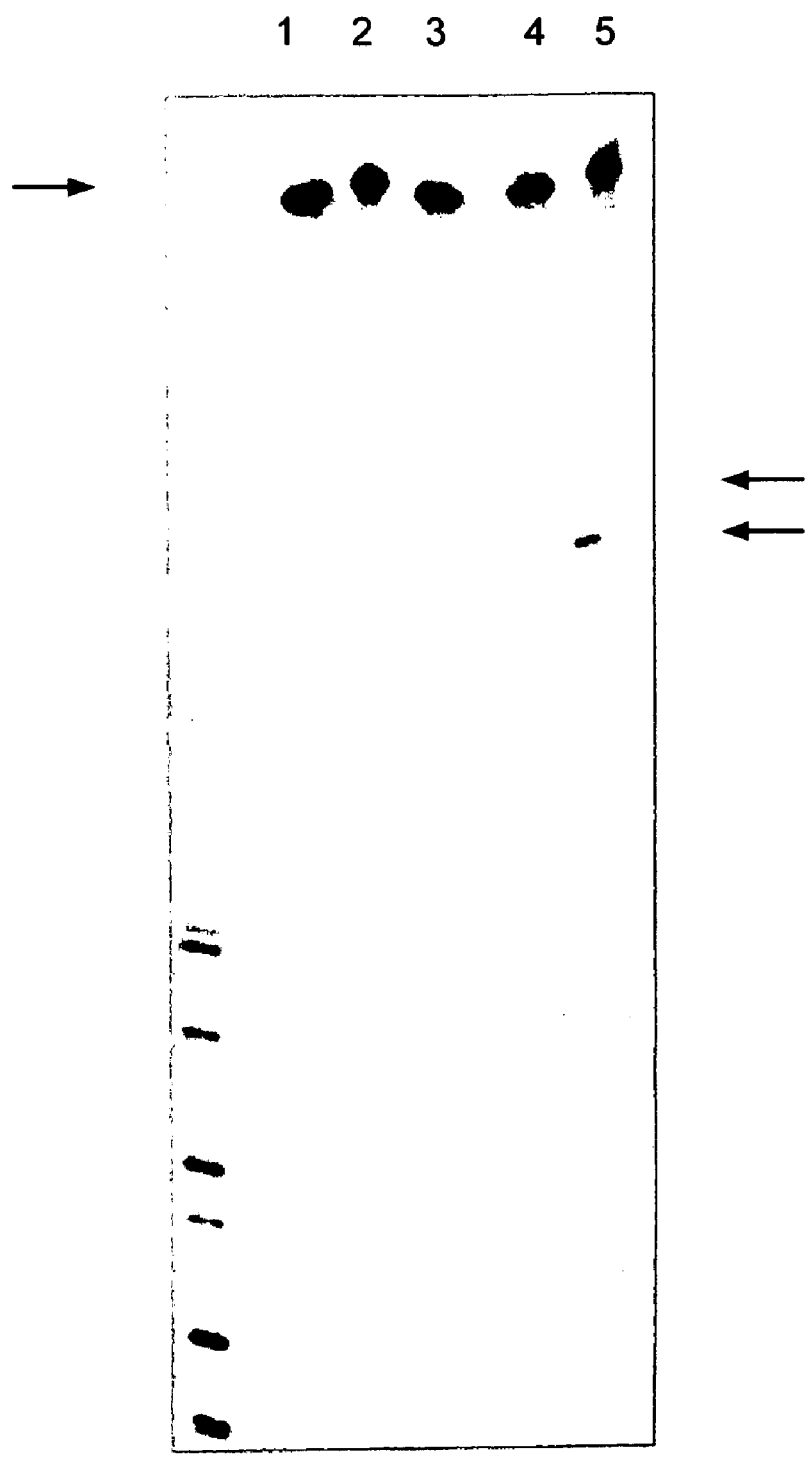
Figure 6B:
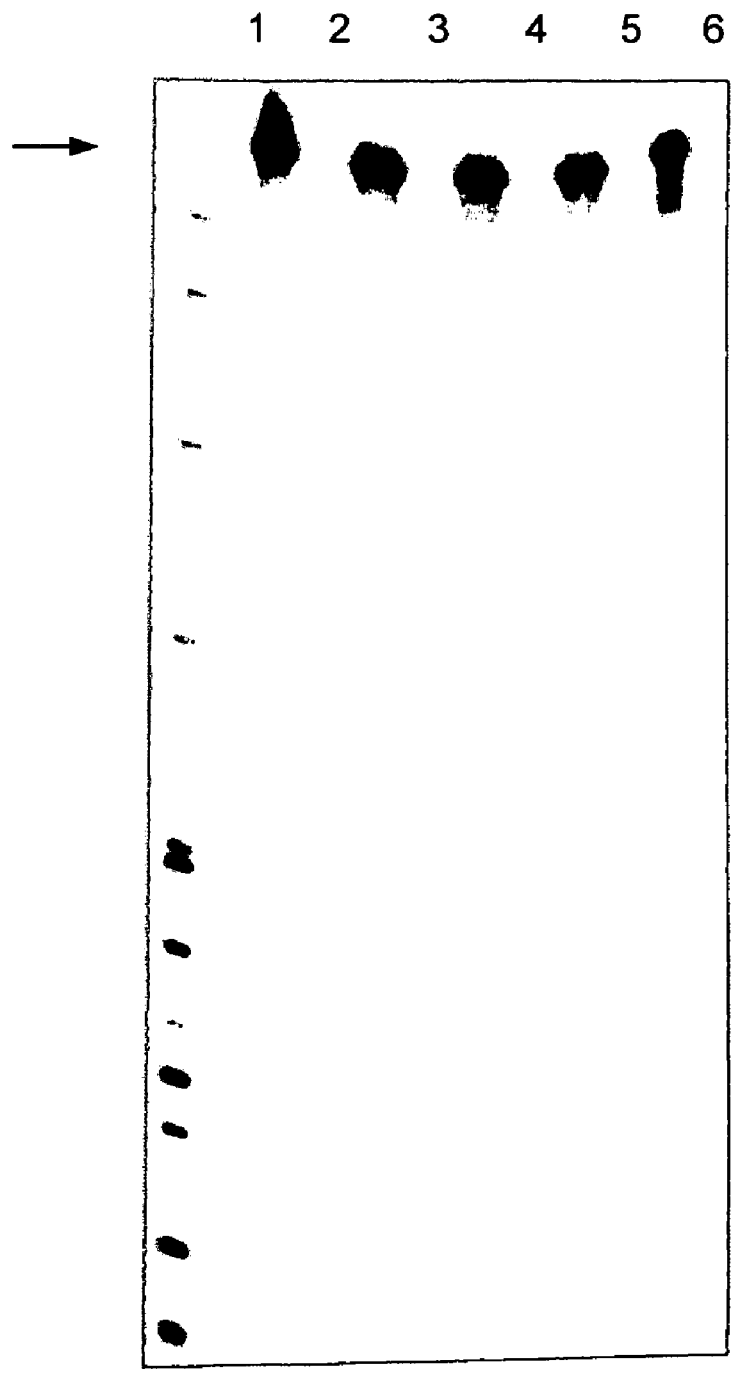

Rz33 was cut with XbaI and expressed in vitro. Similarly the mouse rhodopsin cDNA was cut with Eco47III and expressed in vitro. Resulting RNAs were mixed and incubated with varying concentrations of MgCl$_2$. All expressed products and cleavage products were the correct size. FIG. 6A demonstrates specific cleavage of the mouse rhodopsin RNA over various MgCl$_2$ concentrations incubated at 37° C. for 3 hours. Using a replacement gene with a sequence change around the Rz33 cleavage site (TTT-->TCT) (nucleotides 189–191 of SEQ ID NO:7) which is at a wobble position we demonstrated that transcripts from the replacement gene remain intact due to absence of the Rz33 target site (FIG. 6B). Hence Rz33 could be used to cleave mutant transcripts in a manner independent of the disease mutation itself (that is, using this site) while transcripts from the replacement gene which code for the correct protein would remain intact and therefore could supply the wild type protein.

EXAMPLE 3

Human Peripherin

Figures 7A, 7B:
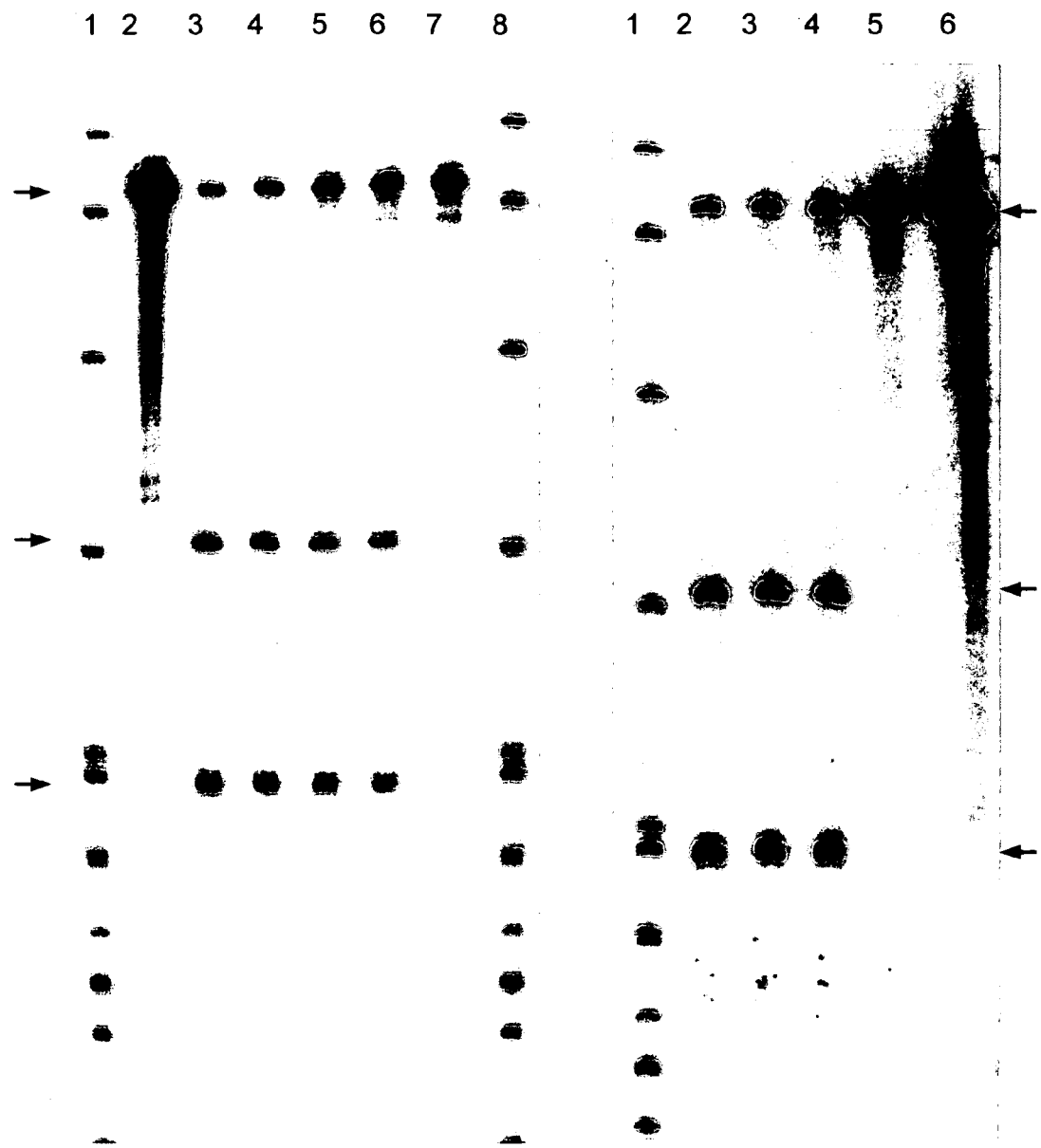
Figure 7C:
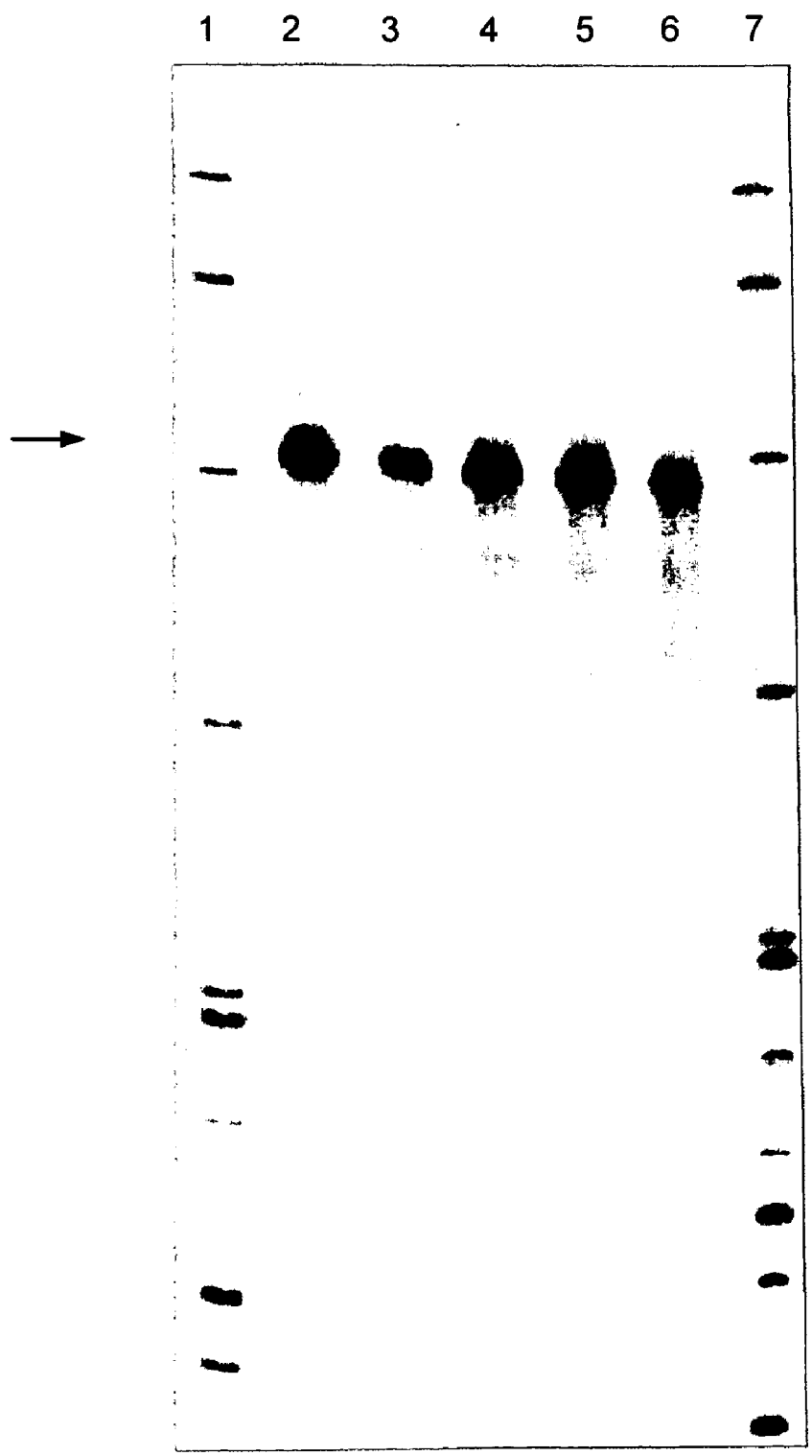
Figure 7D:
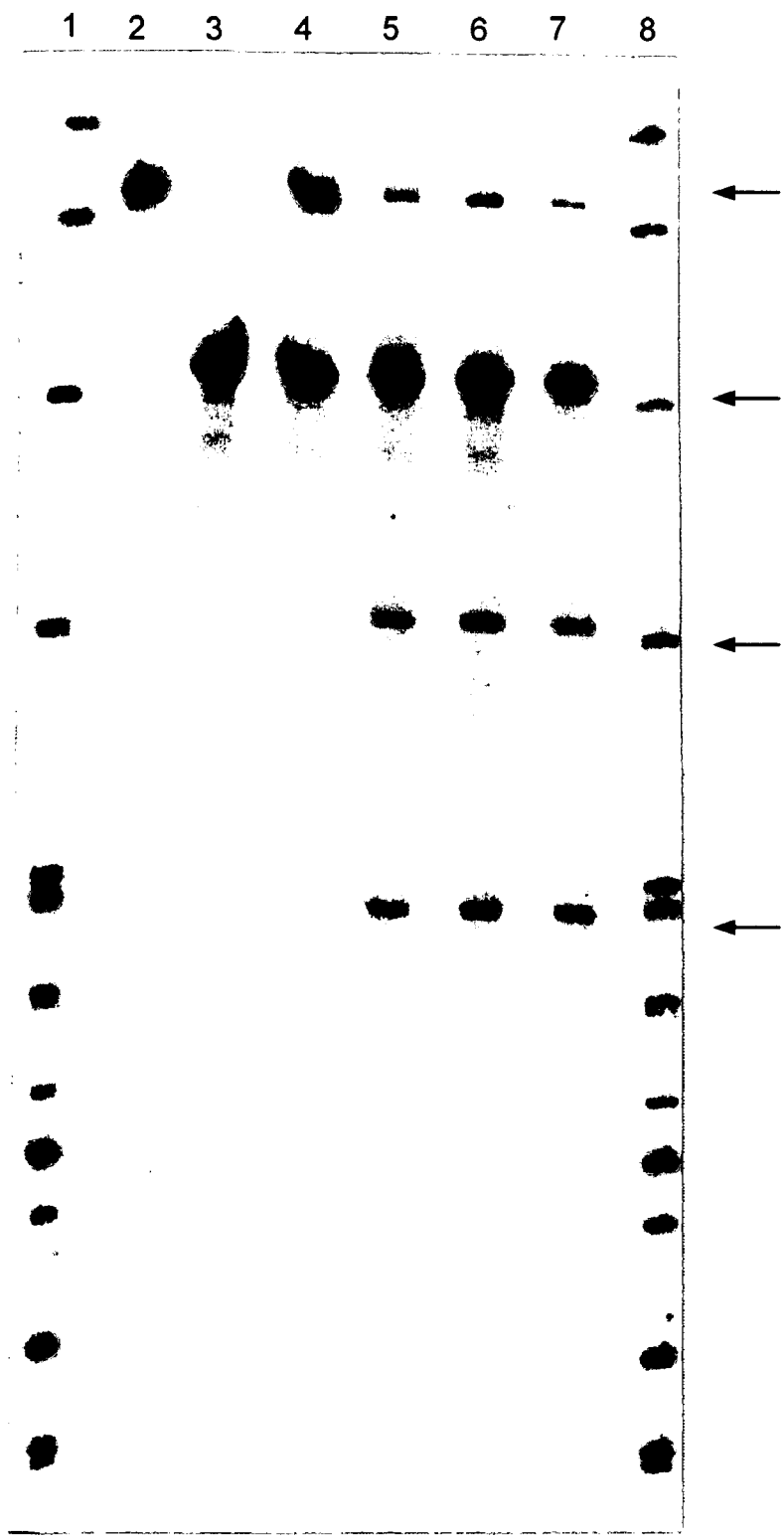
Figure 8A:
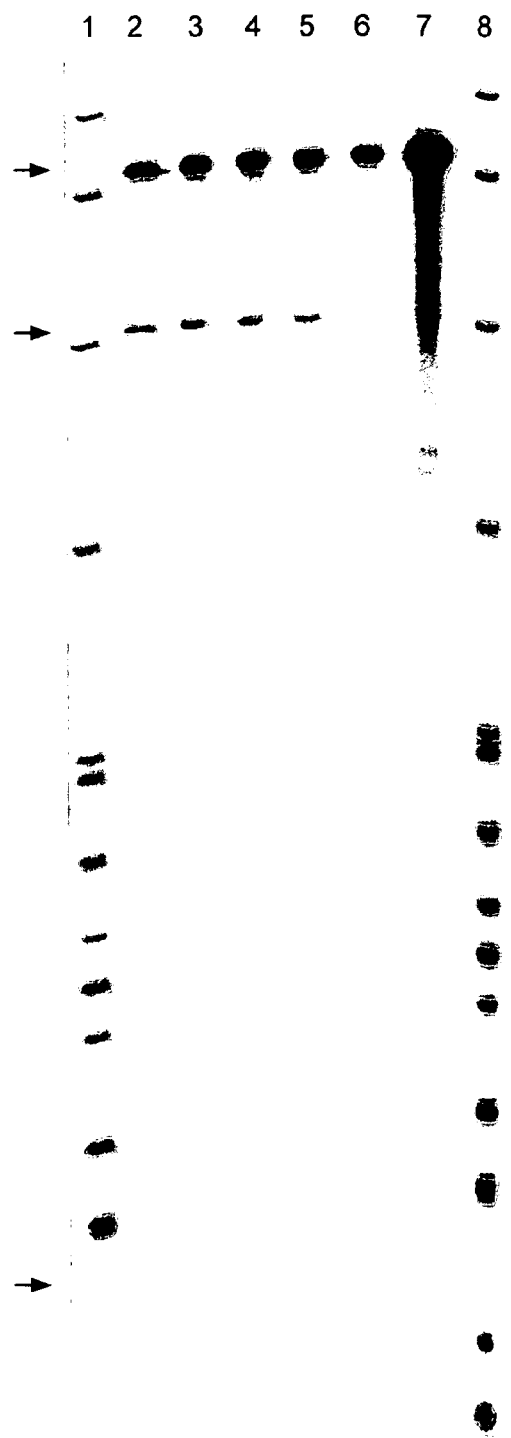
Figure 8B:
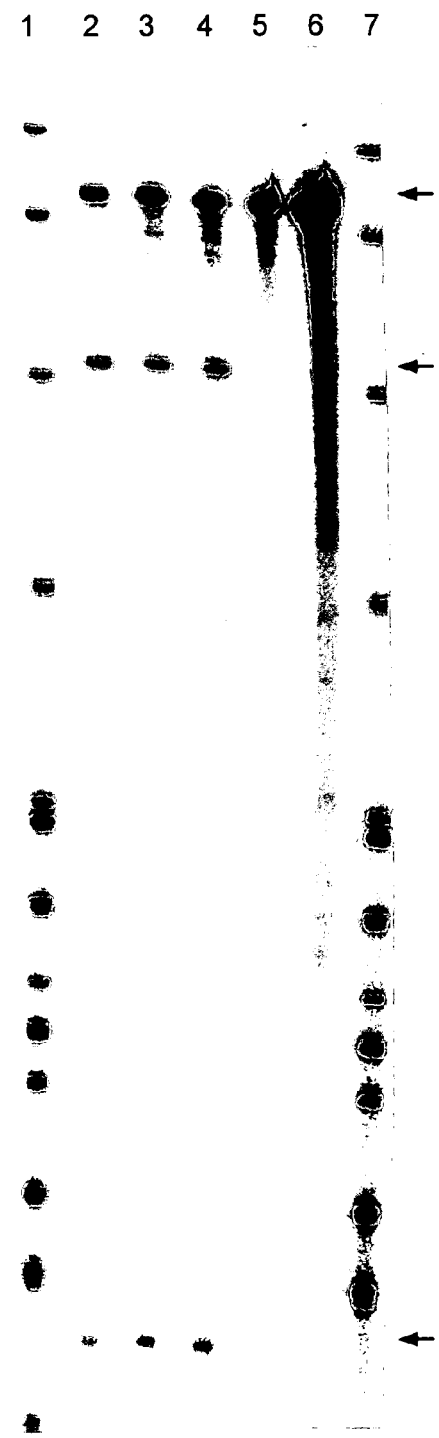
Figure 8C:
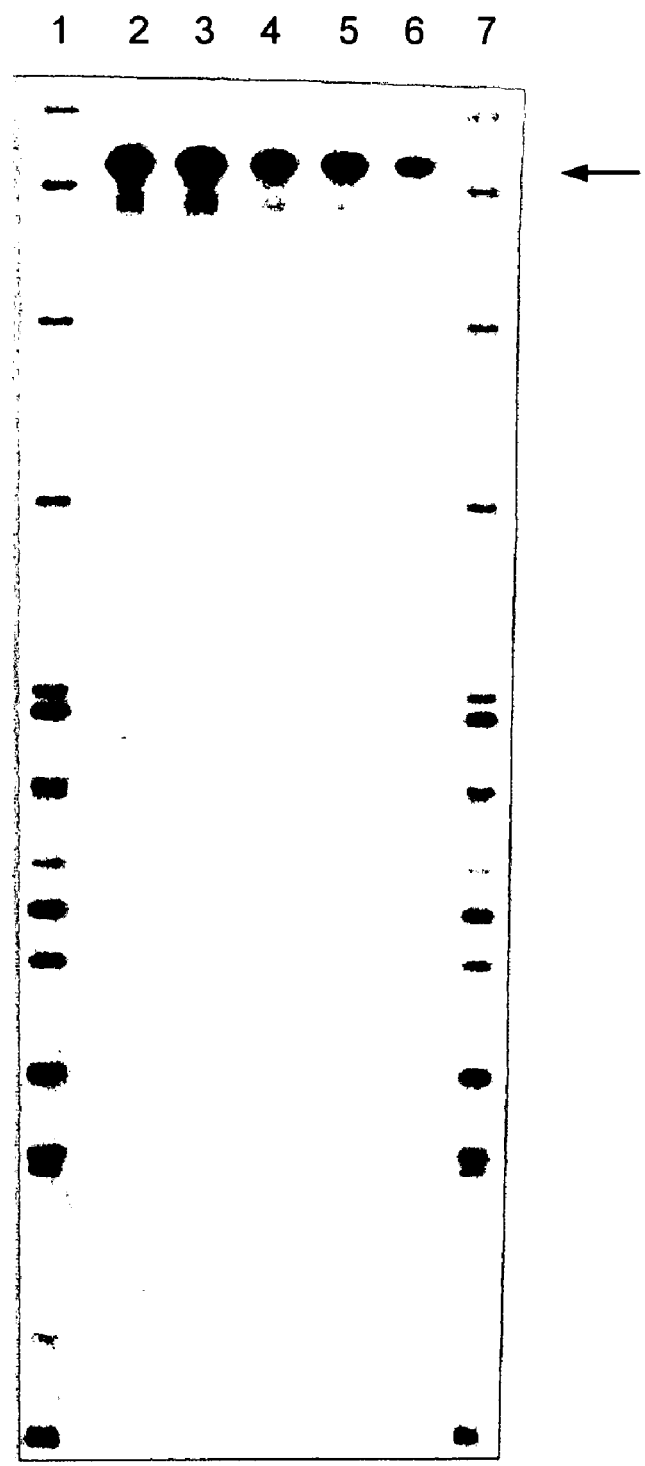

The unadapted human peripherin cDNA and two human peripherin DNA fragments generated by PCR mutagenesis with a single nucleotide substitution in the coding sequence were cut with BglII and AvrII respectively and expressed in vitro. The single base changes in the adapted DNAs occur at third base positions or wobble positions of the codon (at position 257 and 359) (nucleotide 468 of SEQ ID NO:13 and nucleotide 332 of SEQ ID NO:10, respectively) and therefore do not alter the amino acid coded by these triplets. The Rz30 and Rz31 clones were cut with XbaI and expressed in vitro. Resulting ribozymes and unadapted human rhodopsin RNAs were mixed with varying concentrations of MgCl$_2$ to optimise cleavage of template RNA by Rz30 and Rz31. Profiles of human peripherin RNA cleavage by Rz30 over various MgCl$_2$ concentrations and over time are given in FIG. 7. Similarly profiles of human peripherin RNA cleavage by Rz31 over various MgCl$_2$ concentrations and over time are given in FIG. 8. In all cases expressed RNAs were the predicted size. Similarly in all cases unadapted transcripts were cleaved into products of the predicted size. Adapted human rhodopsin RNAs were mixed together with Rz30 and Rz31 RNA over various MgCl$_2$ concentrations to test if adapted human peripherin transcripts could be cleaved by Rz30 and Rz31 (FIGS. 7 and 8). Expressed RNAs were the predicted size. In all cases adapted human peripherin RNAs with single base changes at silent sites remained intact, that is, they were not cleaved by Rz30 or Rz31. Clearly, transcripts from the unadapted human peripherin cDNA are cleaved by Rz30 and Rz31 while transcripts from the adapted replacement DNAs which have been modified in a manner which exploits the degeneracy of the genetic code are protected from cleavage.

EXAMPLE 4

Human Collagen 1A2

Figures 9A, 9B:
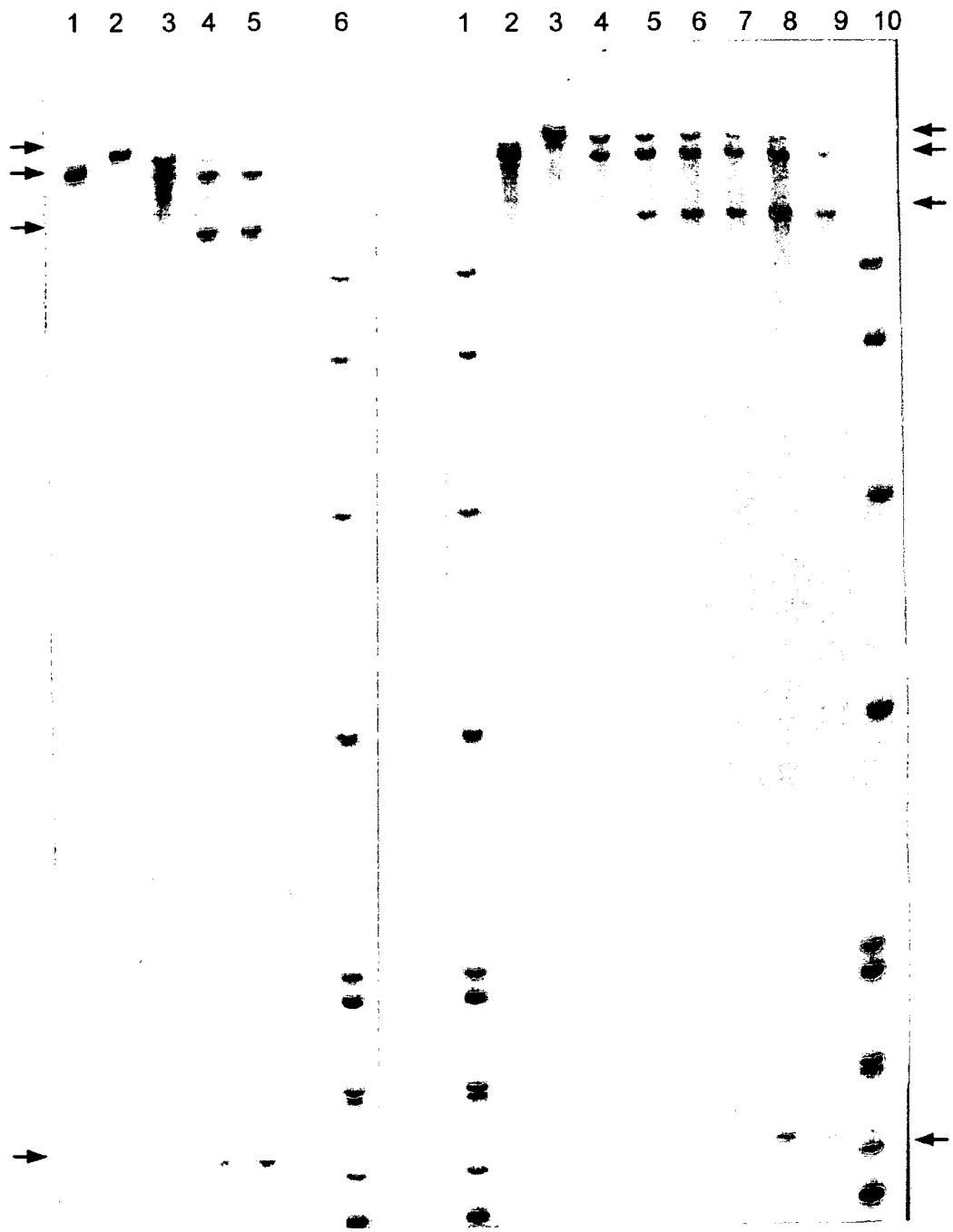

Rz907 clones targeting a polymorphic site in human collagen 1A2 sequence was cut with XbaI and expressed in vitro. The human collagen 1A2 cDNA clones (A and B) containing two allelic forms of a polymorphism in the coding sequence of the gene at positions 907 were cut with MvnI and XbaI respectively, expressed in vitro and RNAs mixed together with Rz907 RNA to test for cleavage of transcripts by this ribozyme. All expressed transcripts were of the predicted sizes. RNAs were mixed with varying concentrations of MgCl$_2$ to optimise cleavage of RNAs by Rz907 (FIG. 9). Notably the majority of the RNA transcripts from human collagen 1A2 (A) which has a T nucleotide at position 907 (A nucleotide 176 of SEQ ID NO:17, reverse strand) is cleaved by Rz907 (FIG. 9). This allelic form of the gene has a ribozyme cleavage site at 906–908. Notably the situation is reversed with transcripts from human collagen 1A2 (B) where in this allelic form of the gene due to the nature of the polymorphism present at position 907 the ribozyme cleavage site has been lost.

In contrast to transcripts from human collagen (A), transcripts from human collagen (B) were protected from cleavage by Rz907 due to the alteration in the sequence around the ribozyme cleavage site (FIG. 9). Cleavage of collagen 1A2 (A) by Rz907 was efficient which is consistent with 2-D predictions of RNA open loop structures for the polymorphism—in the allele containing the Rz907 ribozyme cleavage site, the target site is found quite consistently in an open loop structure. This polymorphism found in an open loop structure of the transcript clearly demonstrates the feasibility and utility of using the degeneracy of the genetic code in the suppression of an endogenous gene (either suppressing both alleles or a single allele at a polymorphic site) and restoration of gene expression using a gene which codes for the same protein but has sequence modifications at third base wobble positions which protect the replacement gene from suppression.

TABLE 1

|  | Restriction Enzyme | RNA Size | Cleavage Products |
|---|---|---|---|
| Example 1 |  |  |  |
| Human rhodopsin | BstEII | 851 bases | 287 + 564 bases |
|  | AcyI | 1183 bases | 287 + 896 bases |
|  | FspI | 309 bases | 287 + 22 |
| Adapted Human rhodopsin | BstEII | 851 bases |  |

TABLE 1-continued

|  | Restriction Enzyme | RNA Size | Cleavage Products |
|---|---|---|---|
| Human rhodopsin Pro-Leu | BstEII | 851 bases | 170 + 681 (Rz20) |
| Human rhodopsin Pro-Leu | BstEII | 851 bases | 287 + 564 (Rz10) |
| Rz10 | XbaI | 52 bases |  |
| Rz20 | XbaI | 52 bases |  |
| (Table 1; SEQ ID NOS:1–5; FIGS. 1–5 |  |  |  |
| Example 2 |  |  |  |
| Mouse rhodopsin | Eco47III | 774 bases | 400 + 374 |
| Adapted mouse rhodopsin | Eco47III | 774 bases |  |
| Rz33 | XbaI | 52 bases |  |
| (Table 1; SEQ ID NOS:6–9; FIG. 6) |  |  |  |
| Example 3 |  |  |  |
| Human peripherin | BglII | 545 bases | 315 + 230 (Rz30) |
| Human peripherin | BglII | 545 bases | 417 + 128 (Rz31) |
| Adapted human peripherin | AvrII | 414 bases |  |
| Adapted human peripherin | BglII | 545 bases |  |
| Rz30 | XbaI | 52 bases |  |
| Rz31 | XbaI | 52 bases |  |
| (Table 1; SEQ ID NOS:10, 13–16; FIGS. 7 and 8) |  |  |  |
| Example 4 |  |  |  |
| Human Collagen 1A2 (B) -Rz907 | XbaI | 888 bases | 690 + 198 bases |
| Human Collagen 1A2 (A) | MvnI | 837 bases |  |
| Rz907 | XbaI | 52 bases |  |
| (Table 1; SEQ ID NOS:16–18; FIG. 9) |  |  |  |

TABLE 2

A: Rhodopsin mutations tested t5lassess if the predicted open loop RNA structure containing the Rz10 target site (475–477) remains intact in mutant transcripts.

| Rhodopsin mutation | RNA open loop targeted by Rz10 |
|---|---|
| Pro 23 Leu | Intact |
| Gly 51 Val | Intact |
| Thr 94 Ile | Intact |
| Gly 188 Arg | Intact |
| Met 207 Arg | Intact |
| Ile del 255 | Intact |

B: Utilisation of the degeneracy of the genetic code. Ribozyme cleavage sites are underlined Human rhodopsin

```
                              475–477
Unadapted sequence    TAC GTC ACC GTC CAG (SEQ ID NO:19)
                          Val
                              475–477
Adapted sequence      TAC GTG ACC GTC CAG (SEQ ID NO:20)
                          Val
```

Mouse rhodopsin

```
                              1459–1461
Unadapted sequence    AAT TTT TAT GTG CCC (SEQ ID NO:21)
                          Phe
                              1459–1461
Adapted sequence      AAT TTC TAT GTG CCC (SEQ ID NO:22)
                          Phe
```

Human peripherin

```
                              255–257
Unadapted sequence    GCG CTA CTG AAA GTC (SEQ ID NO:23)
                          Leu
                              255–257
```

TABLE 2-continued

| | |
|---|---|
| Adapted sequence | GCG CTG CTG AAA GTC (SEQ ID NO:24)<br>Leu<br>357–359 |
| Unadapted sequence | AGC <u>CTA</u> GGA CTG TTC (SEQ ID NO:25)<br>Leu<br>357–359 |
| Adapted sequence | AGC CTG GGA CTG TTC (SEQ ID NO:26)<br>Leu |
| Human type I collagen 1A2 | |
| | 906–908 |
| Sequence (A) | GCT <u>GGT C</u>CC GCC GGT (SEQ ID NO:27)<br>Gly<br>906–908 |
| Sequence (B) | GCT GGA CCC GCC GGT (SEQ ID NO:28)<br>Gly |

Discussion

In the examples outlined above, RNA was expressed from cDNAs coding for four different proteins: human and mouse rhodopsin, human peripherin and human type I collagen 1A2. Rhodopsin and peripherin have been used to exemplify the invention for retinopathies such as adRP—suppression effectors have been targeted to the coding sequences of these genes. In the case of the human collagen 1A2 gene a naturally occurring polymorphism has been used to demonstrate the invention and the potential use of the invention for disorders such as OI—however non-polymorphic regions of the collagen 1A2 gene could be used to achieve suppression. The suppression effectors of choice in the invention have been hammerhead ribozymes with antisense flanks to define sequence specificity. Hammerhead ribozymes require NUX cleavage sites in open loop structures of RNA. Notably, other suppression effectors could be utilised in the invention and may lead to a more flexible choice of target sequences for suppression. Transcripts expressed from all four genes have been significantly attacked in vitro using suppression effectors directed towards target cleavage sites. In all four examples the ribozymes directed to cleavage sites were successful in cleaving target RNAs in the predicted manner. Antisense complementary to sequences surrounding the cleavage sites was used successfully to elicit binding and cleavage of target RNAs in a sequence specific manner. Additionally, transcripts from replacement genes, modified using the degeneracy of the genetic code so that they code for wild type protein, were protected fully from cleavage by ribozymes.

The utility of an individual ribozyme designed to target an NUX site in an open loop structure of transcripts from a gene will depend in part on the robust nature of the RNA open loop structure when various deleterious mutations are also present in the transcript. To evaluate this, we analysed RNAPlotFold data for six different adRP causing mutations in the rhodopsin gene. For each of these, the large RNA open loop structure which is targeted by Rz10 was predicted to be maintained in the mutant transcripts (Table 2A). This is clearly demonstrated in example 1B (FIG. 4) using a Pro23Leu rhodopsin mutation. Rz10 clearly cleaves the mutant transcript effectively in vitro. The Pro23Leu mutation creates a ribozyme cleavage site and can be cleaved in vitro by Rz20 a ribozyme specifically targeting this site—however this is not the case for many mutations. In contrast we have shown that the Rz10 ribozyme cleavage site is available for different mutant rhodopsins and could potentially be used to suppress multiple mutations using a suppression and replacement approach.

In some cases lowering RNA levels may lead to a parallel lowering of protein levels however this may not always be the case. In some situations mechanisms may prevent a significant decrease in protein levels despite a substantial decrease in levels of RNA. However in many instances suppression at the RNA level has been shown to be effective (see prior art). In some cases it is thought that ribozymes elicit—suppression not only by cleavage of RNA but also by an antisense effect due to the antisense arms of the ribozyme surrounding the catalytic core.

In all examples provided ribozymes were designed to cleave at specific target sites. Target sites for four of the ribozymes utilised were chosen in open loop structures in the coding regions of transcripts from three retinal genes (human and mouse rhodopsin and human peripherin). In all cases sequence specific cleavage was obtained at the target cleavage sites (FIGS. 1–7). Target sites were chosen in open loop structures to optimise cleavage. Additionally target sites were chosen such that they could be obliterated by single nucleotide changes at third base wobble positions and therefore would code for the same amino acid (Table 2B). In turn this enabled the generation of replacement genes with single nucleotide alterations which code for wild type protein. In all cases tested transcripts from replacement genes were protected from cleavage by ribozymes. Further modifications could be made to replacement genes in wobble positions, for example, to limit the binding ability of the antisense arms flanking the ribozyme catalytic core. The examples provided for rhodopsin and peripherin involve suppression of expression of both disease and wild type alleles of a retinal gene and restoration of the wild type protein using a replacement gene. However, there may be situations where single alleles can be targeted specifically or partially specifically (PCT/GB97/00574).

In one example, human collagen 1A2, Rz907 was used to target a naturally occurring polymorphic site at amino acid 187, (GGA (glycine)-->GGT (glycine), located in an open loop structure from the predicted 2-D conformations of the transcript (FIG. 9, Table 2B). The ribozyme Rz907 cleaved transcripts containing the GGT sequence but transcripts with GGA were protected from cleavage. Transcripts from both alleles of individuals homozygous for the GGT polymorphism could be cleaved by Rz907 whereas in the case of heterozygotes cleavage could be directed to single alleles (in particular to alleles containing deleterious mutations PCT/GB97/00574). In both situations replacement genes could have the sequence GGA and therefore would be protected from cleavage by Rz907. The presence of many such naturally occurring silent polymorphisms highlights that replacement genes could be modified in a similar fashion in wobble positions and should produce in most cases functional wild type protein. Multiple modifications could be made to replacement genes at wobble positions which would augment protection from suppression effectors. For example, in situations where antisense nucleic acids were used for suppression, transcripts from replacement genes with multiple modifications at third base positions would be protected partially or completely from antisense binding.

In all four examples provided transcripts from cDNA clones were cleaved in vitro in a sequence specific manner at ribozyme cleavage sites. Additionally one base of the ribozyme cleavage site occurs at a wobble position and moreover can be altered so as to eliminate the cleavage site. Ribozyme cleavage sites in the examples given were destroyed by changing nucleotide sequences so that the consensus sequence for ribozyme cleavage sites was broken. However it may be that in some cases the cleavage site could be destroyed by altering the nucleotide sequence in a manner that alters the 2-D structure of the RNA and destroys the open loop structure targeted by the ribozyme. cDNAs or DNA fragments with altered sequences in the regions targeted by ribozymes were generated. RNAs expressed from these cDNAs or DNA fragments, were protected entirely from cleavage due to the absence of the ribozyme cleavage site for each of the ribozymes tested. Of particular interest is the fact that a single nucleotide alteration can obliterate a ribozyme target site, thereby preventing RNA cleavage. Although ribozymes have been used in the demonstration of the invention, other suppression effectors could be used to achieve gene silencing. Again replacement genes with altered sequences (at third base wobble positions) could be generated so that they are protected partially or completely from gene silencing and provide the wild type (or beneficial) gene product.

As highlighted before in the text, using the invention the same method of suppression (targeting coding sequences of a gene) and where necessary gene replacement (using a replacement gene with a sequence modified in third base positions to restore gene expression) may be used as a therapeutic approach for many different mutations within a given gene. Given the continuing elucidation of the molecular pathogenesis of dominant and polygenic diseases the number of targets for this invention is rapidly increasing.

REFERENCES

Carter G and Lemoine NR. (1993) Cancer Res 67: 869–876.
Cazenave et al. (1989) Nuc Acid Res 17: 4255–4273.
D'Alessio M et al. (1991) Am J Hum Genet 49: 400–406.
Dosaka-Akita H et al. (1995) Cancer Res 55: 1559–1564.
Dryja TP et al. (1990) Nature 343: 364–366.
Duval-Valentin et al. (1992) Proc Natl Acad Sci USA 89: 504–508.
Ellis and Rodgers (1993) Nuc Acid Res 21: 5171–5178.
Farrar G J et al. (1991) Nature 354: 478–480.
Farrar G J et al. (1991) Genomics 14: 805–807.
Farrar G J et al. (1995) Invest Ophthamol Vis Sci (ARVO) 36: (4).
Feng M, Cabrera G, Deshane J, Scanlon K and Curiel D T. (1995) Can Res 55: 2024–2028.
Filie et al. (1993) Hum Mut 2: 380–388.
Gaughan D J, Steel D M, Whitehead S A. (1995) FEBS Letters 374: 241–245.
Hanvey J C et al. (1992) Science 258: 1481–1485.
Hardenbol P and Van Dyke M W. (1996) Proc Natl Acad Sci USA 93: 2811–2816.
Herschlag D, Khosla M, Tsuchihashi Z and Karpel R L. (1994) EMBO 13: (12) 2913–2924.
Herskowitz et al. (1987) Nature 329: 219–222.
Humphries P, Kenna P F and Farrar G J. (1992) Science 256: 804–808.
Humphries M et al. (1997) Nat Genet 15: 216–219.
Jankowsky E and Schwenzer B. (1996) Nuc Acid Res 24: (3) 423–429.
Jones J T, Lee S—W and Sullenger B A. (1996) Nature Medicine 2: 643–648.
Jordan SA et al. (1993) Nature Genetics 4: 54–58.
Quattrone A, Fibbi G, Anichini E, Pucci M et al. (1995) Can Res 55: 90–95.
Kajiwara et al. (1991) Nature 354: 480–483.
Knudsen H and Nielsen P E. (1996) Nuc Acid Res 24: (3) 494–500.
Lange W et al. (1993) Leukemia 7: 1786–1794.
Mansergh F et al. (1995) J Med Genet 32: 855–858.
Mashhour B et al. (1994) Gene Therapy 1: 122–126.
McKay R A, Cummins L L, graham M J, Lesnik E A et al. (1996)
Nuc Acid Res 24: (3) 411–417.
McWilliam P et al. (1989) Genomics 5: 612–619.
Ohkawa J, Yuyama N, Takebe Y, Nishikawa S and Taira K. (1993) Proc Natl Acad Sci 90: 11302–11306.
Ohta Y, Kijima H, Ohkawa T, Kashani-Sabet M and Scanlon K J. (1996) Nuc Acid Res 24: (5) 938–942.
Ott J et al. (1989) Proc Natl Acad Sci 87: 701–704.
Oyama T et al. (1995) Pathol Int 45: 45–50.
Phillips CL et al. (1990) J Clin Invest 86: 1723–1728.
Postel et al. (1991) Proc Natl Acad Sci USA 88: 8227–8231.
Porumb H, Gousset, Letellier R, Salle V, et al. (1996)
Sun J S et al. (1989) Proc Natl Acad Sci USA 86: 9198–9202.
Taylor R W et al. (1997) Nat Genetics 15: 212–215.
Trauger J W, Baird E E and Dervan P B. (1996) Nature 382: 559–561.
Valera A et al. (1994) J Biol Chem 269: 28543–28546.
Van Soest S et al. (1994) Genomics 22: 499–504.
Vasan N S et al. (1991) Amer J Hum Genet 48: 305–317.
Wei Z, Tung C—H, Zhu T, Dickerhof W A et al. (1996) Nuc Acid Res 24: (4) 655–661.
Westerhausen A I, Constantinou C D and Prockop D J. (1990) Nuc Acid Res 18: 4968.
Willing M C et al. (1993) Am J Hum Genet 45: 223–227.
Zhuang J et al. (1996) Hum Mut 7: 89–99.

We claim:

1. A method for preparing a suppression effector and replacement nucleic acid, said method comprising:
   a) preparing a suppression effector that binds to a coding region of a mature RNA encoding a mutant allele, thereby to inhibit the expression of the mutant allele, wherein the suppression effector is a nucleic acid or a peptide nucleic acid; and
   b) preparing a replacement nucleic acid that encodes a wild-type or non-disease causing allele and that comprises at least one degenerate/wobble nucleotide that is altered so that the replacement nucleic acid is not suppressed, or is only partially suppressed, by the suppression effector.

2. A method for preparing a suppression effector and replacement nucleic acid, the method comprising:
   a) preparing a ribozyme that cleaves a mature RNA encoding a mutant allele; and
   b) preparing a replacement nucleic acid that encodes a wild-type or non-disease causing allele and that comprises at least one degenerate/wobble nucleotide that is altered so that the replacement nucleic acid is not suppressed, or is only partially suppressed, by the ribozyme.

3. The method of claim 1, wherein the suppression effector is a nucleic acid that forms a triple helix with the mutant allele.

4. The method of claim 1, wherein the suppression effector is an nucleic acid.

5. The method of claim 1, wherein the suppression effector is a single-stranded RNA.

6. The method of claim 1, wherein the suppression effector is a ribozyme that cleaves an RNA encoded by the mutant allele.

7. The method of claim 6, wherein the ribozyme cleaves the RNA at an NUX ribozyme cleavage site.

8. The method of claim 1 or 2, wherein the suppression effector is operatively linked to an expression vector.

9. The method of claim 1 or 2, wherein the replacement nucleic acid encodes a protein selected from the group consisting of mammalian rhodopsin, collagen 1A1, collagen 1A2, and peripherin.

10. The method of claim 1 or 2, wherein the replacement nucleic acid is operatively linked to an expression vector.

11. The method of claim 8, wherein the expression vector is a viral expression vector.

12. A kit comprising:
a) a suppression effector that binds to the coding region of a mature RNA encoding a mutant allele, wherein the suppression effector is a nucleic acid or a peptide nucleic acid; and
b) a replacement nucleic acid that encodes a wild-type or non-disease causing allele that is altered from the mutant allele in at least one degenerate/wobble nucleotide such that binding and/or cleavage of the replacement nucleic acid by the suppression effector is at least partially inhibited so that the replacement nucleic acid is not suppressed, or is only partially suppressed, by the suppression effector.

13. A kit comprising:
a) at least one ribozyme that binds to and/or cleaves the coding region of a mature RNA encoding a mutant allele; and
b) a replacement nucleic acid that encodes a wild-type or non-disease causing allele and that is altered from the mutant allele in at least one degenerate/wobble nucleotide such that binding and/or cleavage of the replacement nucleic acid by the suppression effector is at least partially inhibited, so that the replacement nucleic acid is not suppressed, or is only partially suppressed, by the ribozyme.

14. The kit of claim 12, wherein the suppression effector is a nucleic acid that forms a triple helix with the mutant allele.

15. The kit of claim 12, wherein the suppression effector is a nucleic acid.

16. The kit of claim 12, wherein the suppression effector is a single-stranded RNA.

17. The kit of claim 12, wherein the suppression effector is a ribozyme that cleaves an RNA encoded by the mutant allele.

18. The kit of claim 17, wherein the ribozyme cleaves the RNA at an NUX ribozyme cleavage site.

19. The kit of claim 12, wherein the suppression effector is operatively linked to an expression vector.

20. The kit of claim 12 or 13, wherein the replacement nucleic acid encodes a protein selected from the group consisting of mammalian rhodopsin, collagen 1A1, collagen 1A2, and peripherin.

21. The kit of claim 12 or 13, wherein the replacement nucleic acid is operatively linked to an expression vector.

22. The kit of claim 21, wherein the expression vector is a viral expression vector.

23. A ribozyme comprising a ribonucleotide sequence encoded by nucleotides 101–137 of SEQ ID NO:4.

24. A ribozyme comprising a ribonucleotide sequence encoded by nucleotides 116–153 of SEQ ID NO:14.

25. A ribozyme comprising a ribonucleotide sequence encoded by nucleotides 112–148 of SEQ ID NO:15.

26. A ribozyme comprising a ribonucleotide sequence encoded by nucleotides 107–141 of SEQ ID NO:18.

27. The method of claim 10, wherein the expression vector is a viral expression vector.

28. A composition, the composition comprising:
a) a suppression effector that binds to the coding region of a mature RNA encoding a mutant allele, thereby inhibiting the expression of the mutant allele, wherein the suppression effector is a nucleic acid or a peptide nucleic acid; and
b) a replacement nucleic acid that encodes a wild-type or non-disease causing allele and that comprises at least one degenerate/wobble nucleotide that is altered so that the replacement nucleic acid is not suppressed, or is only partially suppressed, by the suppression effector.

29. A composition, the composition comprising:
a) a ribozyme that cleaves the coding region of a mature RNA encoding a mutant allele; and
b) a replacement nucleic acid that encodes a wild-type or non-disease causing allele and that comprises at least one degenerate/wobble nucleotide that is altered so that the replacement nucleic acid is not suppressed, or is only partially suppressed, by the ribozyme.

30. The composition of claim 28, wherein the suppression effector is a nucleic acid that forms a triple helix with the mutant allele.

31. The composition of claim 28, wherein the suppression effector is a nucleic acid.

32. The composition of claim 28, wherein the suppression effector is a single-stranded RNA.

33. The composition of claim 28, wherein the suppression effector is a ribozyme that cleaves an RNA encoded by the mutant allele.

34. The composition of claim 33, wherein the ribozyme cleaves the RNA at an NUX ribozyme cleavage site.

35. The composition of claim 28, wherein the suppression effector is operatively linked to an expression vector.

36. The composition of claim 29, wherein the ribozyme is operatively linked to an expression vector.

37. The composition of claim 35 or 36, wherein the expression vector is a viral expression vector.

38. The composition of claim 28 or 29, wherein the replacement nucleic acid encodes a protein selected from the group consisting of mammalian rhodopsin, collagen 1A1, collagen 1A2, and peripherin.

39. The composition of claim 28 or 29, wherein the replacement nucleic acid is operatively linked to an expression vector.

40. The composition of claim 39, wherein the expression vector is a viral expression vector.

41. The composition of claim 29, wherein the ribozyme comprises a ribonucleotide sequence encoded by a sequence selected from the group consisting of nucleotides 101–137 of SEQ ID NO:4, nucleotides 116–153 of SEQ ID NO:14, nucleotides 112–148 of SEQ ID NO:15, and nucleotides 107–141 of SEQ ID NO:18.

42. The method of claim 2, wherein the ribozyme comprises a ribonucleotide sequence encoded by a sequence selected from the group consisting of nucleotides 101–137 of SEQ ID NO:4, nucleotides 116–153 of SEQ ID NO:14, nucleotides 112–148 of SEQ ID NO:15, and nucleotides 107–141 of SEQ ID NO:18.

43. The kit of claim 13, wherein the ribozyme comprises a ribonucleotide sequence encoded by a sequence selected from the group consisting of nucleotides 101–137 of SEQ ID NO:4, nucleotides 116–153 of SEQ ID NO:14, nucleotides 112–148 of SEQ ID NO:15, and nucleotides 107–141 of SEQ ID NO:18.

44. The kit of claim 13, wherein the ribozyme is operatively linked to an expression vector.

45. The kit of claim 19 or 44, wherein the expression vector is a viral expression vector.

46. The method of claim 1 or 2, wherein the suppression effector suppresses both alleles of an endogenous gene.

47. The kit of claim 12, wherein the suppression effector suppresses both alleles of an endogenous gene.

48. The kit of claim 13, wherein the ribozyme suppresses both alleles of an endogenous gene.

49. The composition of claim 28, wherein the suppression effector suppresses both alleles of an endogenous gene.

50. The composition of claim 29, wherein the ribozyme suppresses both alleles of an endogenous gene.

51. The method of claim 1 or 2, wherein the RNA is an mRNA.

52. The kit of claim 12 or 13, wherein the RNA is an mRNA.

53. The composition of claim 28 or 29, wherein the RNA is an mRNA.

54. The method of claim 1, wherein the suppression effector and replacement nucleic acid are operatively linked to the same expression vector.

55. The method of claim 2, wherein the ribozyme and replacement nucleic acid are operatively linked to the same expression vector.

56. The method of claim 12, wherein the suppression effector and replacement nucleic acid are operatively linked to the same expression vector.

57. The method of claim 13, wherein the ribozyme and replacement nucleic acid are operatively linked to the same expression vector.

58. The method of claim 28, wherein the suppression effector and replacement nucleic acid are operatively linked to the same expression vector.

59. The method of claim 29, wherein the ribozyme and replacement nucleic acid are operatively linked to the same expression vector.

* * * * *

SEQUENCE LISTING

```
<160> NUMBER OF SEQ ID NOS: 34

<210> SEQ ID NO 1
<211> LENGTH: 617
```

```
<212> TYPE: DNA
<213> ORGANISM: Artificial Sequence
<220> FEATURE:
<223> OTHER INFORMATION: The human rhodopsin cDNA cloned in pCDNA3
<220> FEATURE:
<221> NAME/KEY: misc_feature
<222> LOCATION: (1)..(617)
<223> OTHER INFORMATION: n is any nucleotide

<400> SEQUENCE: 1
tcccttntgn tagattgcan nncccaataa aanaaggncc cgcttaaagg cttatcgaaa      60
ttaatacgac tcactatang gagacccaag cttagagtca tccagctgga gccctgagtg     120
gctgagctca ggccttcgca gcattcttgg gtgggagcag ccacgggtca gccacaaggg     180
ccacagccat gaatggcaca gaaggcccta acttctacgt gcccttctcc aatgcgacgg     240
gtgtggtacg cagccccttc gagtacccac agtactacct ggctgagcca tggcagttct     300
ccatgctggc cgcctacatg tttctgctga tcgtgctggg cttccccatc aacttcctca     360
cgctctacgt caccgtccag cacaagaagc tgcgcacgcc tctcaactac atcctggctc     420
aacctagccg tggctgaact cttcatggtc ctangtggct tcaccagcac ctctacanct     480
ctctgcatgg atactcgtct tcgggcccac aggatgcaat tgganggctc tttgcacctg     540
gngggaaatt gcctgtggtc ctngtggtcn ggncaccaac gtactggtng tgtntancccc    600 agaacaactc cgctccc                                                   617

<210> SEQ ID NO 2
<211> LENGTH: 639
<212> TYPE: DNA
<213> ORGANISM: Artificial Sequence
<220> FEATURE:
<223> OTHER INFORMATION: The human rhodopsin hybrid cDNA with a C-->G
      change at nucleotide 271
<220> FEATURE:
<221> NAME/KEY: misc_feature
<222> LOCATION: (1)..(639)
<223> OTHER INFORMATION: n is any nucleotide

<400> SEQUENCE: 2
ggnnnnttgg gtcgcgcatt naagaactca nggncccgca gcattcttgg gtgggagcag      60
ctacgggtca gccacaaggg ccacagccat gaatggcaca gaangcccta acttctacgt     120
gcccttctcc aatgcgacgg gtgtggtacg cagccccttc gagtacccac agtactacct     180
ggctgagcca tggcagttct ccatgctggc cgcctacatg tttctgctga tcgtgctggg     240
cttccccatc aacttcctca cgctctacgt gaccgtccag cacaagaagc tgcgcacgcc     300
tctcaactac atcctgctca acctanccgt ggntgaactc ttcatggtcc taggtggctt     360
caccancaac ctctanacct ctctgcatgg anacttcntc ttccggccca caggatgcaa     420
tttggaaggn ttcctttaac acccgggggg ggaaaattgc ctgtggtcct tggtggtccg     480
gncancnaac ggtacttgtg gtntttaanc cataaacaat tccgcttcgg gaaaaacatg     540
ccancntggg gtttccttca ctnggttang ggcnggctgc ccccacccca atcccnggtn     600
gtcaantaat cccaagggcn nantgncntt ttaaacaaa                           639

<210> SEQ ID NO 3
<211> LENGTH: 686
<212> TYPE: DNA
<213> ORGANISM: Artificial Sequence
<220> FEATURE:
<223> OTHER INFORMATION: A human rhodopsin adRP mutation, a C-->T change
      at nucleotide 217
<220> FEATURE:
```

<221> NAME/KEY: misc_feature
<222> LOCATION: (1)..(686)
<223> OTHER INFORMATION: n is any nucleotide

<400> SEQUENCE: 3

| | | |
|---|---|---|
| nnnttagggn cggatgtcna tataagcaga nctctctggg ctaactaana agaaccccact | 60 |
| ggcttactgg cttatcgaaa ttaatacgac tcactatagg gagacccaag cttccggaaa | 120 |
| gcctgagctc agccacaagg gccacagcca tgaatggcac agaaagccct aacttctacg | 180 |
| tgccccttctc caatgcgacg ggtgtggtac gcagcctctt cgagtaccca cagtactacc | 240 |
| tggctgagcc atggcagttc tccatgctgg ccgcctacat gtttctgctg atcgtgctgg | 300 |
| gcttccccat caacttcctc acgctctacg tcaccgtcca gcacaagaag ctgcgcacgc | 360 |
| ctctcaacta catcctgctc aacctanccg tggctgaact cttcatggtc ctangtggct | 420 |
| tcaccancac cctctacacc tctctgcatg gatacttcgt cttccgggcc acaggatgca | 480 |
| atttggaagg cttctttgca ncctgggncg ggaaattgcc tgtngtcctg gtggtcctgg | 540 |
| ccatcaacng tacttgttgt ntnttaccca tnaacaattc cgctccggga aaacatgcac | 600 |
| atgggnttgc ctcactnggt ctggggcngg cnccccaccc caccccggt ggtcanttat | 660 |
| cccanggcgn aatgcctttn annaaa | 686 |

<210> SEQ ID NO 4
<211> LENGTH: 787
<212> TYPE: DNA
<213> ORGANISM: Artificial Sequence
<220> FEATURE:
<223> OTHER INFORMATION: A hammerhead ribozyme (termed Rz10) cloned in pCDNA3
<220> FEATURE:
<221> NAME/KEY: misc_feature
<222> LOCATION: (1)..(787)
<223> OTHER INFORMATION: n is any nucleotide.

<400> SEQUENCE: 4

| | | |
|---|---|---|
| cngcncgttg aaatataagc agaccctctg gntaactana ataaccactg cttactggct | 60 |
| tatcgaaatt aatacgactc actatangga gaccaagctt ggtcggtctg atgagtccgt | 120 |
| gaggacgaaa cgtagagtct anagggccct attctatagt gtcacctaaa tgctaganct | 180 |
| cgctgatcag cctcgactgt gccttctagt tgccagccat ctgttgtttg cccctccccc | 240 |
| gtgccttcct tganccctgga aggtgccact cccactgtcc tttcctaata aaatgagnaa | 300 |
| ttgcntctca ttgtctgagt agtgtcatcc aatctggggg tgggtggggc agnacacnag | 360 |
| gggaagatgg gaaaacatac aggcatgctg gggangccgt ggntctatgn ctcngaggcg | 420 |
| aaaaaacact ggggnctagg ggtaccccac cccctgtacg gccataacnc ngggtttgtg | 480 |
| gtacccacta acgtanntgc accctacccg ncttcnttct cctcttncca tttccggttc | 540 |
| cctcaccnaa cgggccttng tcatatctng gnccaccaaa tanagtagtc tttgccccca | 600 |
| aagtccctna tgacctntaa gaccttcann anccccccctt ntttnaaana nccnnnnnnn | 660 |
| nnnnannnnc cngnaaaaaan aacaactaat tttgggaacc ccccccnana aaccctttcc | 720 |
| ntnttccccc natttaatnt tnnnntnccc ccccccccc cccnntttt tnncncccn | 780 |
| nnannng | 787 |

<210> SEQ ID NO 5
<211> LENGTH: 665
<212> TYPE: DNA
<213> ORGANISM: Artificial Sequence
<220> FEATURE:

```
<223> OTHER INFORMATION: A hammerhead ribozyme (termed Rz20) cloned in
      pCDNA3
<220> FEATURE:
<221> NAME/KEY: misc_feature
<222> LOCATION: (1)..(665)
<223> OTHER INFORMATION: n is any nucleotide.

<400> SEQUENCE: 5
nnccccgccc ntttnaaana anccnagcct ctggcnaact ananaaccac tgcttactgg      60
cttatcnaaa ttaatacgac tcactatagg gagacccaag ctttactcga actgatgagt    120
ccgtgaggac gaaaggctgc tctananggc cctattctat antgtcacct aaatgctaga    180
gctcgctgat cagcctcgac tgtgccttct aattgccagc catctgttgt ttgcccctcc    240
cccgtgcctt ccttgaccct ggaaggtgcc actcccactg tcctttccta ataaaatgaa    300 gatntttncat cncattgtct gagtaagtgt cattctattc tgggggtgg ggtggggcac    360 gacancaaag gggaagattg ggaaaaaata ncaggcntgc tggggatncc gtgggctcta    420
tngcttctga agcggaaaaa acaactgggg ctctangggg tatccccccc ccctgtaac    480 gngcattaaa cncggggtg ttgtggttac cccaacttaa cgctancttg caacgcccna    540 acgcccncc tttccttct cccttccttc ncccactttc cgggttcccn tcaacccnaa    600
tcggggcccc ttaggtccaa ttatgcttcg gccccnccccn aaactaatag gtnggttctt    660 tngcc                                                                665

<210> SEQ ID NO 6
<211> LENGTH: 624
<212> TYPE: DNA
<213> ORGANISM: Artificial Sequence
<220> FEATURE:
<223> OTHER INFORMATION: Mouse rhodopsin cDNA cloned into pCDNA3
<220> FEATURE:
<221> NAME/KEY: misc_feature
<222> LOCATION: (1)..(624)
<223> OTHER INFORMATION: n is any nucleotide.

<400> SEQUENCE: 6
nnnncttnct tanngcttgg taccganctc ggatccacta gtnaacggcc gccagtgtgc      60
tggaaattcc cagaggnact ctggggcaga caagatgaga caccctttcc tttctttacc    120
taagggcctc caccccgatgt caccttggcc cctctgcaag ccaattaggc cccgtggca    180 gcagtgggat tagcgttagt atgatatctc gcggatgctg aatcagcctc tggcttaggg    240
agagaaggtc actttataag ggtctggggg gggtcagtgc ctggagttgc gctgtgggag    300
ccgtcagtgg ctgagctcgc caagcagcct tggtctctgt ctacgaaaan cccgtggggc    360
agcctcnana accgcagcca tgaacggcac agaaggcccc aatttttatg tgcccttctc    420
caacgtcaca ngcgtggtgc ggaaccccctt cnancanccg cagtactacc tggcggaacc    480
atggcagttc tccatgctgg cancgtacat gtcctgctca tcgtgctggg nttcccatca    540
actcctcacg ctctagttca ccgtaaanna naaaaactg cgcaacccct caactaaatc    600
ctgctcaatt gggcgtgggt gaac                                           624

<210> SEQ ID NO 7
<211> LENGTH: 630
<212> TYPE: DNA
<213> ORGANISM: Artificial Sequence
<220> FEATURE:
<223> OTHER INFORMATION: Mouse rhodopsin hybrid cDNA with a T-->C change
      at nucleotide 190
<220> FEATURE:
<221> NAME/KEY: misc_feature
```

<222> LOCATION: (1)..(630)
<223> OTHER INFORMATION: n is any nucleotide.

<400> SEQUENCE: 7

| | | | | | |
|---|---|---|---|---|---|
| nnnntcttcc | nctttcgttt | gttgnanant | cannaaanan | aggcgncccg | gaaggtgtca | 60 |
| gtgcctggag | ttgcgctgtg | ggacccgtca | ntggctgagc | tcgccaagca | gccttggtct | 120 |
| ctgtctacga | agagcccgtg | gggcagcctc | gagagccgca | gccatgaacg | gcacagaggg | 180 |
| ccccaatttc | tatgtgccct | tctccaacgt | cacaggcgtg | gtgcggagcc | ccttcgancn | 240 |
| tccgcagtac | tacctggcgg | aaccatggca | gttctccatg | ctggcagcgt | acatgttcct | 300 |
| gctcatcgtg | ctgggcttcc | ccatcaactt | cctcacgctc | tacgtcaccg | tacagcacaa | 360 |
| gaagctgcgc | acacccctc | aactacatcc | tggctcaact | tgggccgntg | ggnttggaac | 420 |
| ctccttccca | ttgggtcntt | cccggaangg | antncaccaa | ccaccctct | aacacatcaa | 480 |
| ctcccatggg | ctacttcgtt | cttttggggc | ccncaggctg | ttaatctcga | agggcttctt | 540 |
| tgccacacct | tggaagtgaa | atcncccctg | ggttccctgg | tggtcntggc | cattaacgct | 600 |
| acttgtggtc | ctgcaaccca | ataacaattc | | | | 630 |

<210> SEQ ID NO 8
<211> LENGTH: 649
<212> TYPE: DNA
<213> ORGANISM: Artificial Sequence
<220> FEATURE:
<223> OTHER INFORMATION: A hammerhead ribozyme (termed Rz33) cloned in pCDNA3
<220> FEATURE:
<221> NAME/KEY: misc_feature
<222> LOCATION: (1)..(649)
<223> OTHER INFORMATION: n is any nucleotide.

<400> SEQUENCE: 8

| | | | | | |
|---|---|---|---|---|---|
| tcccctnntt | tttgtagcnc | tgccaanaaa | aaaggccagc | tcacaggana | antananaac | 60 |
| ccactgctta | ctggcttanc | naaattaata | cgactcacta | tagggagacc | caagcttggc | 120 |
| acatctgatg | agtccgtgag | gacgaaaaaa | ttggtctaca | gggccctatt | ctataatgtc | 180 |
| acctaaatgc | tanagctcgc | tgatcatcct | cnactgtgcc | ttctacttgc | cagccntctn | 240 |
| ttgtttgccc | ctccccgtg | ccttccttga | ccctggaagg | tgccactccc | actgtcctt | 300 |
| cctaataaaa | tgaggaaatt | gcatcgcatt | gtctgagtaa | gtgtcattct | attctggggg | 360 |
| gtggggtggg | gcaggacnnc | aaagggaag | attgggaaat | acaatancca | aggancnctc | 420 |
| ccccngggta | attgcggatt | nggctctntc | gcttccttaa | ggcngaaana | aacaactngg | 480 |
| gcgctncggg | gttccccn | cccncccctnt | tagcngcgca | ttantcgccg | cgggtgttgt | 540 |
| tgttactccc | cacctnaacg | ctacanttgc | cagcgcctaa | cgcccccct | tnctnttctt | 600 |
| ccctcctttc | tcncacttcc | ccggctttcc | ccnccaancc | naaatcngg | | 649 |

<210> SEQ ID NO 9
<211> LENGTH: 681
<212> TYPE: DNA
<213> ORGANISM: Artificial Sequence
<220> FEATURE:
<223> OTHER INFORMATION: Human peripherin cDNA cloned in pCDNA3
<220> FEATURE:
<221> NAME/KEY: misc_feature
<222> LOCATION: (1)..(681)
<223> OTHER INFORMATION: n is any nucleotide.

<400> SEQUENCE: 9

| | | | | | |
|---|---|---|---|---|---|
| nnttgttggt | ncagtnggat | gtctatataa | gcagagnctc | tggctaacta | gnagaaccca | 60 |

```
ctgcttactg gcttatcgaa attaatacga ctcactatag ggagacccaa gcttggtacc    120
gagctcngat ccactagtaa cggccgccag tgtgctggaa ttcttcagcg cccacgacca    180
gtgactatcc cctgctcaag ctgtgattcc gagacccctg ccaccactac tgcattcacg    240
ggggatccca ngctaatggg actcgacatg ggttgccccc acggcanctc cctacanctt    300
gggccanctn cacttttccc aaagnccaa atctccgcct ctcggctcnt taangttngg     360
ggtgggganc tgtgctgtgg gaaacaaccc agaananact tgggcagcat ggngctactg    420
aaagtncatt ttgaacagaa naaacggtcc antttggccc aaggnncnng ntcctaaant    480
ggttctccnt ntttggtngn ntccncnctt tccncctngg aatgttcctg aaaaattnaa    540
cnccaaaaaa gaacaaattg aaaaatantt ctnaaaaccc ttttgttncc cccccccna    600 aaagggaagg ggnnggnncc tttttnttcc ccccccgggg ggggaaaatt ttnnnnaanc    660
cccccccccc ccnttttttn a                                              681

<210> SEQ ID NO 10
<211> LENGTH: 612
<212> TYPE: DNA
<213> ORGANISM: Artificial Sequence
<220> FEATURE:
<223> OTHER INFORMATION: Human peripherin hybrid DNA with a A--->G change
      at nucleotide 332
<220> FEATURE:
<221> NAME/KEY: misc_feature
<222> LOCATION: (1)..(612)
<223> OTHER INFORMATION: n is any nucleotide.

<400> SEQUENCE: 10
ttatacnaca cactatangg agaccaagct tggtaccgag ctcggatcca ctagtaacgg     60
ccgccagtgt gctggaattc ttcancgccc aggaccagga ctatcccctg ctcaagctgt    120
gattccgaga cccctgccac cactactgca ttcacggggg atcccaggct agtgggacnc    180
gacatgggta tcccccaggg cagctcccta cagcttgggc catctgcact tttcccaagg    240
ccctaagtct ccgcctctgg gctcgttaan gtntggggtg ggagctgtgc tgtgggaaac    300
aacccggact acacttggca agcatggcgc tgctgaaagt caagtttgaa cagaaaaaan    360
gggtcaagtt ggcccaaggg ctctggctca gggaaactgg gttncccncc nngttttngg    420
tttggntgca tcanctncca aaaanannnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nn                                                        612

<210> SEQ ID NO 11
<211> LENGTH: 20
<212> TYPE: DNA
<213> ORGANISM: Artificial Sequence
<220> FEATURE:
<223> OTHER INFORMATION: Forward 257 mutation primer

<400> SEQUENCE: 11
catggcgctg ctgaaagtca                                                20

<210> SEQ ID NO 12
<211> LENGTH: 20
<212> TYPE: DNA
<213> ORGANISM: Artificial Sequence
<220> FEATURE:
<223> OTHER INFORMATION: Forward 359 mutation primer
```

-continued

```
<400> SEQUENCE: 12
catcttcagc ctgggactgt                                                    20

<210> SEQ ID NO 13
<211> LENGTH: 610
<212> TYPE: DNA
<213> ORGANISM: Artificial Sequence
<220> FEATURE:
<223> OTHER INFORMATION: A second human peripherin hybrid DNA with a
      A-->G change at nucleotide 468
<220> FEATURE:
<221> NAME/KEY: misc_feature
<222> LOCATION: (1)..(610)
<223> OTHER INFORMATION: n is any nucleotide.

<400> SEQUENCE: 13
tttttntggn tntcnaatta atacgactca ctagggag acccaagctt ggtaccgagc          60
tcggatccac tagtaacggc cgccagtgtg ctggaattct tcancgccca ggaccaggac       120
tatcccctgc tcaagctgtg attccgagac ccctgccacc actactgcat tcacggggat      180
cccaggctag tgggactcga catgggtagc cccagggca gctccctaca gcttgggcca       240
tctgcacttt tcccaaggcc ctaagtctcc gcctctgggc tcgttaaggt ttggggtggg      300
agctgtgctg tgggaagcaa cccggactac acttggcaag catggcgcta ctgaaagtca     360
agtttgacca gaaaaancgg gtcaagttgg gcccaagggc tctgggctcn atgnaaacct     420 nggtttccccc ccccctnttt gggctgggca tcatcatctt tcagcctggg antgttcctg    480
aanattgaac tcccaaagag ancgatgtga tgaataattc tgaaanccat tttgtgcccc     540
actcattgan aagganggg tgnatcctgt ttcttcactc cctgntggaa aatgctacaa      600 ncccctgaacc                                                            610

<210> SEQ ID NO 14
<211> LENGTH: 679
<212> TYPE: DNA
<213> ORGANISM: Artificial Sequence
<220> FEATURE:
<223> OTHER INFORMATION: Hammerhead ribozyme (termed Rz30) cloned in
      pCDNA3
<220> FEATURE:
<221> NAME/KEY: misc_feature
<222> LOCATION: (1)..(679)
<223> OTHER INFORMATION: n is any nucleotide.

<400> SEQUENCE: 14
cnttggtggt nctgtcggnt gtctatataa gcagagctct ctggctaact agaagaaccc     60
actgcttact ggcttatcga aattaatacg actcactata gggagaccca agcttacttt    120
cagctgatga gtccgtgagg acgaaagcgc catctagagg gccctattct atagtgtcac    180
ctaaatgcta gagctcgctg atcagcctcg actgtgcctt ctagttgcca gccatctgtt    240
gtttgcccct ccccgtgcc ttccttgacc ctggaaggtg ccactccac tgtcctttcc      300 taataaaatg atgaaattgc atcgcattgt ctgagtaggt gtcattctat tctgggggt     360 gggtggggca ngacancaag ggggaagatt gggaaaacaa tncccgcctg ctgggatgc     420 ggtgggctct atggcttctg aggcgaaana acnnctgggg tctngggggt tcccnccccc    480
ctgtnncggc cttnanncgg gggttttgtg ntccccccnc ttancnnton ttnnnnnncc    540 nnccccccnnc nntncnnttn ntccnnnnnn tncncnnntt nnnngnntc cnnnnnnnnt    600 nnnnngggc ncnnnngntc cnntnnnncc ncnnnnnncn nncnnnnnnn nntntgnngg     660
```

```
cccnnnncnn nnnnncncn                                              679
```

<210> SEQ ID NO 15
<211> LENGTH: 691
<212> TYPE: DNA
<213> ORGANISM: Artificial Sequence
<220> FEATURE:
<223> OTHER INFORMATION: Hammerhead ribozyme (termed Rz31) cloned in
      pCDNA3
<220> FEATURE:
<221> NAME/KEY: misc_feature
<222> LOCATION: (1)..(691)
<223> OTHER INFORMATION: n is any nucleotide.

<400> SEQUENCE: 15

```
nntttntcct acgnccgttt taaananaac cagaccctct gganaattan atnnccactg    60
cttactggct tatcgaaatc aatacgactc actatangga gacccaagct tacagtccct   120
gatgagtccg tgaggacgaa aggctgaatc tanagggccc tattctatag tgtcacctaa   180
atgctagagc tcgctgatca gcctcgactg tgccttctaa ttgccagcca tctgttgttt   240
gcccctcccc cgtgccttcc ttgaccctgg aaggtgccac tcccactgtc ctntcctaat   300
aaaatgatga nnttgcatcg cattgtctga gtaagtgtca ntctattctg gggggtgggg   360
tggggcanga cancaagggg gaagattggg aaaaacattn cacgcatgcc ggggatgcg    420 gtgggctctn ttngcntcng aaggcngaaa aaaacnactg gggccctang ggtnnccnn    480 tccccntgt aacngnccctt naacngggg gtttgtggtt nnccnanctt ancnctnaac    540
ttccnncccc nnnccccnc tcttcccttt ttcctccatc tccncntttn cccgntctcc    600
cttncactna aatggggcc cctacngggn ctntntntct cttnnnnccn ccnccnana     660 natatnctng ntnnttcncc tctcggcccc t                                  691
```

<210> SEQ ID NO 16
<211> LENGTH: 805
<212> TYPE: DNA
<213> ORGANISM: mammalian
<220> FEATURE:
<221> NAME/KEY: misc_feature
<222> LOCATION: (1)..(805)
<223> OTHER INFORMATION: n is any nucleotide
<220> FEATURE:
<221> NAME/KEY: misc_feature
<223> OTHER INFORMATION: Human collagen 1A2 (B)

<400> SEQUENCE: 16

```
ntcncgncat ttaancaggc caggnctacc gcnnggtcca ngtaggccgg gagccccagc    60
aacgccggga aggccagcag caccccttggc accagtaagg ccgtttgctc caggattacc   120
angaggtcca acggggccgg agaggcctgg aanaccactt caccacgggg aaccggcggg   180
tccagtagga ccagcgttac caacagctcc aatttcaccc ttggggccag gggcacctgg   240
gaagcctgga nggccagcag accaatggga ccagcaggac cacggaccac acttccatca   300
ctgctttngc ncagctgggc aagggcacaa cacttctctc tcacangaac ccacggctcc   360
tgtttnactg aattccattt cacagggcac agttcacctt cacacaagaa cacggntgtc   420
cttcatcatc agacatgttt ccctaatgct tgagcagant cagattcagg aaacacacac   480
ctttgtccac atctctncac agtctcggtt tcaggtacac tcccacctgc agaggcactg   540
accaacctga gacattgaca ttncagncca cagtctgaac tgagcgggca cgccatggcn   600
agtcatacct gtcagnatca tcttctctta ncattcccaa ngggcagaat gaaagctgac   660
tccccaatgt cttatttta annanggttt naaanaannn nnnnnnnnn nnnnnnnnc     720
```

```
cccccccctt tngggtttat tatctatncn ncccntngga tatcttcc ccnttncccc    780 ctnaaanttt tnttntttt tnnnn                                        805
```

<210> SEQ ID NO 17
<211> LENGTH: 797
<212> TYPE: DNA
<213> ORGANISM: mammalian
<220> FEATURE:
<221> NAME/KEY: misc_feature
<222> LOCATION: (1)..(797)
<223> OTHER INFORMATION: n is any nucleotide
<220> FEATURE:
<221> NAME/KEY: misc_feature
<223> OTHER INFORMATION: Human collagen 1A2 (A)

<400> SEQUENCE: 17

```
ccctttaaaa canggccagg aataccgcgg ggtccaggga ggccgggacc ccancaacgc    60
cgggaangcc cagcagcacc cttggcacca gtaangccgt ttgctccagg attaccagga   120
ggtccaacgg ggccggagan gcctggaaga ccacttcacc acggggaacg gcgggaccag   180
cangaccagc gttaccaaca gctccaattt caccccttggg gccaggggca cctgggaagc   240 ctggangcc agcagaccaa tgggancagc aggaccacgg gaccacactt ccatcnctgc   300
cnctggcacc agctgggcaa gggcacaaca cttctctctc acnaagaacc cacggntcct   360
gtttaactga attccatttc acagggcaca gttcaccttc anacagaaca cgggtgtcct   420
tcatcatcaa acatntttcc tatnccttga gcagaatcag attcaggaac acacactttg   480
tcacatctcc tcacagtctc ggtttcaggt aacactcnca cctgcagagg cactgacnaa   540
nctcaganat ttanattccn ctccncagtt tgaacttagg cgggcccnn catttggntt   600 gtcctaacct ntnggggggtt ttncttnnnn nnnnnntt nacnantccc aangggggana   660 ananagntga ctcctatgtc ttntntnaa aaggtttttn aaaaattaac ccccccctn   720 ttgggttatt tatttttttt nncccccctt ttgngaancn tnncccntt ttcccnnna   780 aanttttttn ttttttt                                                  797
```

<210> SEQ ID NO 18
<211> LENGTH: 697
<212> TYPE: DNA
<213> ORGANISM: Artificial Sequence
<220> FEATURE:
<223> OTHER INFORMATION: A hammerhead ribozyme (termed Rz907) cloned in pCDNA3
<220> FEATURE:
<221> NAME/KEY: misc_feature
<222> LOCATION: (1)..(697)
<223> OTHER INFORMATION: n is any nucleotide

<400> SEQUENCE: 18

```
nctttcnntc tnatncatan aagcaggccc tctnnaaaaa ctananttc cactgcttac    60 tggcttatcg aaancaatac gactcactat agggagaccc aagcttcggc ggctgatgag   120
tccgtgagga cgaaaccagc atctagaggg ccctattcta tagtgtcacc taaatgctag   180
agctcgctga tcagcctcga ctgtgccttc tagttgccag ccatctgttg tttgcccctc   240
ccccgtgcct tccttgaccc tggaaggtgc cactcccact gtcctttcct aataaaatga   300
ngaaattgca tcgcattgtc tgagtangtg tcattctatt ctgggggggtg gggtggggca   360 ngacancaag ggggaagatt gggaanacaa taacaggcat gctggggatg cgtgggctc   420 tatggcttct gaggcggaaa gaaccaactg gggctctang gggtatcccc acncccctgt   480
```

-continued

```
taccggcgca ttaancgcgg gggtgttgtg gttaccnca acttaacgct acacttgcca      540
cgcctaacgc ccctcctttc gcttcttcct tccttctccc acttccccgn tttcccttca      600
actctaatcg gggcnccta ggtccaatta atcttacggn cncacccaaa actnataggt      660
aagtccttnt ggcccccaa aaaggttccc ctaaatg                                697
```

<210> SEQ ID NO 19
<211> LENGTH: 15
<212> TYPE: DNA
<213> ORGANISM: Artificial Sequence
<220> FEATURE:
<223> OTHER INFORMATION: Human rhodopsin unadapted sequence with
      ribozyme cleavage site

<400> SEQUENCE: 19
tacgtcaccg tccag                                                       15

<210> SEQ ID NO 20
<211> LENGTH: 15
<212> TYPE: DNA
<213> ORGANISM: Artificial Sequence
<220> FEATURE:
<223> OTHER INFORMATION: Human rhodopsin adapted sequence

<400> SEQUENCE: 20
tacgtgaccg tccag                                                       15

<210> SEQ ID NO 21
<211> LENGTH: 15
<212> TYPE: DNA
<213> ORGANISM: Artificial Sequence
<220> FEATURE:
<223> OTHER INFORMATION: Mouse rhodopsin unadapted sequence with
      ribozyme cleavage site

<400> SEQUENCE: 21 aattttatg tgccc                                                        15

<210> SEQ ID NO 22
<211> LENGTH: 15
<212> TYPE: DNA
<213> ORGANISM: Artificial Sequence
<220> FEATURE:
<223> OTHER INFORMATION: Mouse rhodopsin adapted sequence

<400> SEQUENCE: 22
aatttctatg tgccc                                                       15

<210> SEQ ID NO 23
<211> LENGTH: 15
<212> TYPE: DNA
<213> ORGANISM: Artificial Sequence
<220> FEATURE:
<223> OTHER INFORMATION: Human peripherin unadapted sequence with
      ribozyme cleavage site

<400> SEQUENCE: 23
gcgctactga aagtc                                                       15

<210> SEQ ID NO 24
<211> LENGTH: 15
<212> TYPE: DNA
<213> ORGANISM: Artificial Sequence
<220> FEATURE:
<223> OTHER INFORMATION: Human peripherin adapted sequence

```
<400> SEQUENCE: 24
gcgctgctga aagtc                                                    15

<210> SEQ ID NO 25
<211> LENGTH: 15
<212> TYPE: DNA
<213> ORGANISM: Artificial Sequence
<220> FEATURE:
<223> OTHER INFORMATION: Human peripherin unadapted sequence with
      ribozyme cleavage site

<400> SEQUENCE: 25
agcctaggac tgttc                                                    15

<210> SEQ ID NO 26
<211> LENGTH: 15
<212> TYPE: DNA
<213> ORGANISM: Artificial Sequence
<220> FEATURE:
<223> OTHER INFORMATION: Human peripherin adapted sequence

<400> SEQUENCE: 26
agcctgggac tgttc                                                    15

<210> SEQ ID NO 27
<211> LENGTH: 15
<212> TYPE: DNA
<213> ORGANISM: Artificial Sequence
<220> FEATURE:
<223> OTHER INFORMATION: Human type I collagen 1A2 (A) sequence with
      ribozyme cleavage site

<400> SEQUENCE: 27
gctggtcccg ccggt                                                    15

<210> SEQ ID NO 28
<211> LENGTH: 15
<212> TYPE: DNA
<213> ORGANISM: Artificial Sequence
<220> FEATURE:
<223> OTHER INFORMATION: Human type I collagen 1A2 (B) sequence

<400> SEQUENCE: 28
gctggacccg ccggt                                                    15

<210> SEQ ID NO 29
<211> LENGTH: 37
<212> TYPE: DNA
<213> ORGANISM: Artificial Sequence
<220> FEATURE:
<223> OTHER INFORMATION: A hammerhead ribozyme Rz10

<400> SEQUENCE: 29
ggtcggtctg atgagtccgt gaggacgaaa cgtagag                             37

<210> SEQ ID NO 30
<211> LENGTH: 37
<212> TYPE: DNA
<213> ORGANISM: Artificial Sequence
<220> FEATURE:
<223> OTHER INFORMATION: A hammerhead ribozyme Rz20

<400> SEQUENCE: 30
tactcgaact gatgagtccg tgaggacgaa aggctgc                             37
```

-continued

```
<210> SEQ ID NO 31
<211> LENGTH: 37
<212> TYPE: DNA
<213> ORGANISM: Artificial Sequence
<220> FEATURE:
<223> OTHER INFORMATION: A hammerhead ribozyme Rz33

<400> SEQUENCE: 31
ggcacatctg atgagtccgt gaggacgaaa aaattgg                              37

<210> SEQ ID NO 32
<211> LENGTH: 37
<212> TYPE: DNA
<213> ORGANISM: Artificial Sequence
<220> FEATURE:
<223> OTHER INFORMATION: A hammerhead ribozyme Rz30

<400> SEQUENCE: 32
actttcagct gatgagtccg tgaggacgaa agcgcca                              37

<210> SEQ ID NO 33
<211> LENGTH: 37
<212> TYPE: DNA
<213> ORGANISM: Artificial Sequence
<220> FEATURE:
<223> OTHER INFORMATION: A hammerhead ribozyme Rz31

<400> SEQUENCE: 33
acagtccctg atgagtccgt gaggacgaaa ggctgaa                              37

<210> SEQ ID NO 34
<211> LENGTH: 35
<212> TYPE: DNA
<213> ORGANISM: Artificial Sequence
<220> FEATURE:
<223> OTHER INFORMATION: A hammerhead ribozyme Rz907

<400> SEQUENCE: 34
cggcggctga tgagtccgtg aggacgaaac cagca                                35
```